(12) United States Patent
LaChappelle

(10) Patent No.: US 10,940,026 B2
(45) Date of Patent: Mar. 9, 2021

(54) PROSTHETIC ARM WITH ADAPTIVE GRIP

(71) Applicant: Unlimited Tomorrow, Inc., Rhinebeck, NY (US)

(72) Inventor: Easton J. LaChappelle, Rhinebeck, NY (US)

(73) Assignee: Unlimited Tomorrow, Inc., Rhinebeck, NY (US)

( * ) Notice: Subject to any disclaimer, the term of this patent is extended or adjusted under 35 U.S.C. 154(b) by 90 days.

(21) Appl. No.: 16/242,057

(22) Filed: Jan. 8, 2019

(65) Prior Publication Data

US 2019/0209345 A1    Jul. 11, 2019

Related U.S. Application Data

(60) Provisional application No. 62/615,137, filed on Jan. 9, 2018.

(51) Int. Cl.
*A61F 2/54* (2006.01)
*A61F 2/58* (2006.01)
(Continued)

(52) U.S. Cl.
CPC ............ *A61F 2/586* (2013.01); *A61F 2/5046* (2013.01); *A61F 2/54* (2013.01); *A61F 2/583* (2013.01); *A61F 2/68* (2013.01); *A61F 2/70* (2013.01); *A61F 2/72* (2013.01); *A61F 2/80* (2013.01); *B33Y 80/00* (2014.12); *A61F 2002/5001* (2013.01); *A61F 2002/505* (2013.01); *A61F 2002/5066* (2013.01);
(Continued)

(58) Field of Classification Search
CPC ...... A61F 2/50; A61F 2/54; A61F 2/58; A61F 2/586; A61F 2/68; A61F 2002/6827; A61F 2002/587; B25J 13/082; B25J 13/00
See application file for complete search history.

(56) References Cited

U.S. PATENT DOCUMENTS 2,853,711 A    9/1958  Becker
2005/0043822 A1  2/2005  Didrick
(Continued)

FOREIGN PATENT DOCUMENTS

WO    2008030419 A2    3/2008
WO    2015060793 A1    4/2015

OTHER PUBLICATIONS

International Search Report and Written Opinion for PCT/US19/12603, dated Apr. 9, 2019.

*Primary Examiner* — Bruce E Snow
(74) *Attorney, Agent, or Firm* — Lerner, David, Littenberg, Krumholz & Mentlik, LLP

(57) ABSTRACT

An upper extremity prosthesis may include a prosthetic hand including a prosthetic thumb having a base and a tip, and a prosthetic index finger having a base and a tip. Actuators may be coupled to the upper extremity prosthesis. Prosthetic flexion tendons may have first ends operably coupled to the actuators and second ends coupled to the tips of the thumb and the index finger. Biasing systems may be operably coupled to the prosthetic thumb and the index finger. Upon actuation of the actuators in a first direction, the prosthetic flexion tendons cause the thumb and index finger to flex. Upon actuation of the linear actuators in a second direction opposite the first direction, the biasing systems cause the thumb and index finger to extend.

16 Claims, 62 Drawing Sheets

(51) Int. Cl.
  *A61F 2/80*  (2006.01)
  *A61F 2/68*  (2006.01)
  *B33Y 80/00*  (2015.01)
  *A61F 2/70*  (2006.01)
  *A61F 2/50*  (2006.01)
  *A61F 2/72*  (2006.01)
  *A61F 2/76*  (2006.01)

(52) U.S. Cl.
  CPC ............ *A61F 2002/5072* (2013.01); *A61F 2002/5093* (2013.01); *A61F 2002/543* (2013.01); *A61F 2002/546* (2013.01); *A61F 2002/587* (2013.01); *A61F 2002/6827* (2013.01); *A61F 2002/6854* (2013.01); *A61F 2002/6863* (2013.01); *A61F 2002/701* (2013.01); *A61F 2002/704* (2013.01); *A61F 2002/762* (2013.01); *A61F 2002/764* (2013.01); *A61F 2002/7635* (2013.01)

(56) References Cited

U.S. PATENT DOCUMENTS

| | | |
|---|---|---|
| 2006/0129248 A1 | 6/2006 | Stark |
| 2012/0150322 A1* | 6/2012 | Goldfarb ............... A61F 2/68 623/63 |
| 2013/0053984 A1 | 2/2013 | Hunter et al. |
| 2014/0277589 A1 | 9/2014 | Veatch |
| 2015/0351935 A1* | 12/2015 | Donati ............... A61F 2/72 623/25 |
| 2017/0049583 A1 | 2/2017 | Belter et al. |
| 2017/0266020 A1 | 9/2017 | Glasgow |

\* cited by examiner

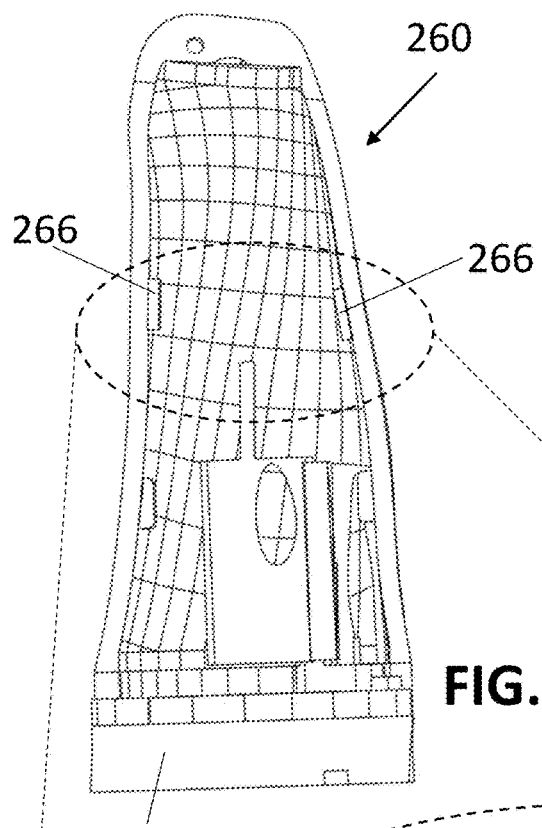
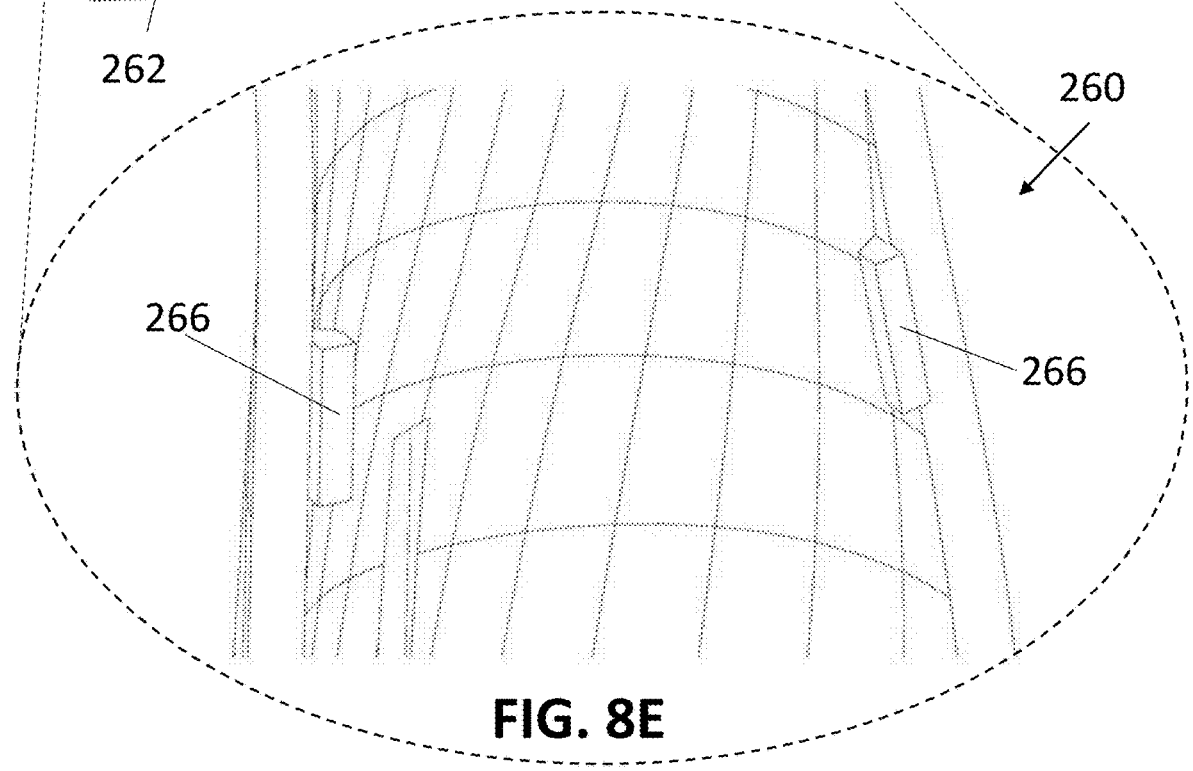
FIG. 8D
FIG. 8E

PROSTHETIC ARM WITH ADAPTIVE GRIP

CROSS-REFERENCE TO RELATED APPLICATIONS

This application claims the benefit of the filing date of U.S. Provisional Patent Application No. 62/615,137 filed Jan. 9, 2018, the disclosure of which is hereby incorporated by reference herein.

BACKGROUND OF THE DISCLOSURE

The present disclosure is directed to robotic prosthetic arms, and particularly to patient-specific prosthetic arms with adaptive grips.

Prosthetic arms have been available for use, for example by amputees, for many years. More recently, mechanical and robotic components have been introduced into prosthetic arms to provide a wide range of functionality to the prosthetic arm, for example, with individual finger joints with various mechanisms of control, including based on the user's muscle control.

Conventional upper extremity prosthetic devices can be expensive and can take a long time to produce, which may make them unsuitable or undesirable for many uses. Some advanced electric hands on the market use a linkage mechanism to move the fingers to grab objects and perform tasks. This generally means that the fingers have a predetermined motion path and are unable to conform to objects. These hands may cost between $10,000 and $30,000, not including the cost to create the socket which couples to the residual limb of the user. The socket creation may result in even more time and even more cost to the prosthesis. As a result, many child amputees do not use these existing market devices. The conventional socket system is generally created by hand and is manual labor intensive. This may include making a plaster negative mold of the user's residual limb, then casting a positive, and molding a thermal plastic around this positive. From there, the socket may be tested and the process repeated until the socket fits properly and is comfortable. Muscle sensors may be molded into the socket to sense specific muscles that are used to control the hand. These sensors may use surface electrodes to sense the electrical activity of the user's muscle. The result of all of this is a generic and heavy robotic-looking device. In order to provide a more natural appearance of the prosthesis, custom silicon gloves have been created to match the user's skin tone, but this can dramatically increase costs and the glove often wears and breaks down rapidly. Thus, there is much room for improvement in robotic upper extremity prosthetic devices.

BRIEF SUMMARY

According to a first aspect of the disclosure, an upper extremity prosthesis includes a prosthetic hand including a prosthetic thumb having a base and a tip and a prosthetic index finger having a base and a tip. The prosthesis may include first and second linear actuators fixedly coupled to the upper extremity prosthesis and first and second springs fixedly coupled to the upper extremity prosthesis. A first prosthetic flexion tendon may have a first end coupled to the first linear actuator and a second end coupled to the tip of the prosthetic thumb. A first prosthetic extension tendon may have a first end coupled to the first spring and a second end coupled to the tip of the prosthetic thumb. A second prosthetic flexion tendon may have a first end coupled to the second linear actuator and a second end coupled to the tip of the prosthetic index finger. A second prosthetic extension tendon may have a first end coupled to the second spring and a second end coupled to the tip of the prosthetic index finger. Upon actuation of the first linear actuator in a first direction, the first prosthetic flexion tendon causes the prosthetic thumb to flex and upon actuation of the first linear actuator in a second direction opposite the first direction, tension on the first prosthetic extension tendon provided by the first spring causes the thumb to extend. Upon actuation of the second linear actuator in the first direction, the second prosthetic flexion tendon causes the prosthetic index finger to flex, and upon actuation of the second linear actuator in the second direction, tension on the second prosthetic extension tendon provided by the second spring causes the prosthetic index finger to extend.

The prosthetic hand may include a prosthetic middle finger having a base and a tip, a prosthetic ring finger having a base and a tip, and a prosthetic pinky having a base and a tip. A third linear actuator may be fixedly coupled to the upper extremity prosthesis. Third, fourth, and fifth springs may be fixedly coupled to the upper extremity prosthesis. A third prosthetic flexion tendon may have a first end coupled to the third linear actuator and a second end coupled to the tip of the prosthetic middle finger. A fourth prosthetic flexion tendon may have a first end coupled to the third linear actuator and a second end coupled to the tip of the prosthetic ring finger. A fifth prosthetic flexion tendon may have a first end coupled to the third linear actuator and a second end coupled to the tip of the prosthetic pinky finger. Third, fourth, and fifth prosthetic extension tendons may each have a first end coupled to the third, fourth, and fifth springs, respectively, and a second end coupled to the tip of the prosthetic middle finger, prosthetic ring finger, and prosthetic pinky finger, respectively. Upon actuation of the third linear actuator in the first direction, the first, second, and third prosthetic flexion tendons may cause the prosthetic middle finger, prosthetic ring finger, and prosthetic pinky finger to flex, respectively, and upon actuation of the third linear actuator in the second direction, tension on the third, fourth, and fifth prosthetic extension tendons provided by the third, fourth, and fifth springs, respectively, causes the prosthetic middle finger, prosthetic ring finger, and prosthetic pinky finger to extend, respectively.

The prosthesis may also include a prosthetic forearm coupled to the prosthetic hand. The prosthetic forearm may include a main forearm portion and a forearm cover, the prosthetic forearm defining a substantially hollow interior volume when the main forearm portion is coupled to the forearm cover. The first and second linear actuators may be mounted to an interior of the main forearm portion. The first and second springs may be mounted to the interior of the main forearm portion. The prosthetic hand may include first and second prosthetic flexion tendon tunnels having outlets in the tip of the prosthetic thumb and prosthetic index finger, respectively, and first and second prosthetic extension tendon tunnels having outlets in the tip of the prosthetic thumb and prosthetic index finger, respectively, the first and second prosthetic flexion tendons passing through the first and second prosthetic flexion tendon tunnels, respectively, and the first and second prosthetic extension tendons passing through the first and second prosthetic extension tendon tunnels, respectively.

The prosthesis may include a socket coupled to the prosthetic forearm, the socket adapted to interface with a residual limb of a user of the upper extremity prosthesis. A force may be sensor coupled to the socket and adapted to provide information to a processor within the upper extremity prosthesis in response to a muscle contraction of the user, the processor adapted to actuate the first and second linear actuators based on the information. An electromyography sensor may be coupled to the socket and adapted to provide information to a processor within the upper extremity prosthesis in response to a muscle contraction by the user, the processor adapted to actuate the first and second linear actuators based on the information. A combined sensor may be coupled to the socket, the combined sensor including a force sensor and an electromyography sensor, the combined sensor adapted to provide information to a processor within the upper extremity prosthesis in response to a muscle contraction of the user, the processor adapted to actuate the first and second linear actuators based on the information.

The prosthetic index finger may include a middle portion positioned between the base and the tip of the prosthetic index finger. The tip of the prosthetic index finger may be rotatable relative to the middle portion of the prosthetic index finger, the middle portion of the prosthetic index finger may be rotatable relative to the base of the prosthetic index finger, and the base of the prosthetic index finger may be rotatable relative to a palm of the prosthetic hand. Upon actuation of the first linear actuator in the first direction, during a first flexion action the base of the prosthetic index finger may rotate relative to the palm, during a second flexion action the middle portion of the prosthetic index finger may rotate relative to the base of the prosthetic index finger, and during a third flexion action the tip of the prosthetic index finger may rotate relative to the middle portion of the prosthetic index finger. Upon actuation of the first linear actuator in the first direction, the first flexion action may occur prior to the second flexion action, and the second flexion action may occur prior to the third flexion action.

A prosthetic index fingernail may be adapted to couple to the tip of the prosthetic index finger. In an assembled condition, the prosthetic index fingernail and the tip of the prosthetic index finger may form a substantially closed outer boundary, and in an unassembled condition, the tip of the prosthetic index finger may present an opening to access an interior volume of the tip of the prosthetic index finger. In the assembled condition, the prosthetic index fingernail may be magnetically coupled to the tip of the prosthetic index finger. Similar or identical prosthetic fingernails may also be provided for any or all of the remaining prosthetic fingers and/or prosthetic thumb.

The base of the prosthetic thumb may be coupled to the prosthetic hand via a pin, and the prosthetic thumb may be rotatable about the pin between a first rotational position and a second rotational position. A locking pin may lock the prosthetic thumb in the first rotational position and in the second rotational position in the absence of rotational force being applied to the prosthetic thumb.

According to a second aspect of the disclosure, an upper extremity prosthesis may include a prosthetic hand including a prosthetic thumb having a base and a tip, and a prosthetic index finger having a base and a tip. First and second actuators may be operably coupled to the upper extremity prosthesis. A first prosthetic flexion tendon may have a first end operably coupled to the first actuator and a second end coupled to the tip of the prosthetic thumb. A first biasing system may be operably coupled to the prosthetic thumb. A second prosthetic flexion tendon may have a first end operably coupled to the second actuator and a second end coupled to the tip of the prosthetic index finger. A second biasing system may be operably coupled to the prosthetic index finger. Upon actuation of the first actuator in a first direction, the first prosthetic flexion tendon may cause the prosthetic thumb to flex, and upon actuation of the first actuator in a second direction opposite the first direction, the first biasing system may cause the prosthetic thumb to extend. Upon actuation of the second actuator in the first direction, the second prosthetic flexion tendon may cause the prosthetic index finger to flex, and upon actuation of the second actuator in the second direction, the second biasing system may cause the prosthetic index finger to extend.

The prosthetic hand may include a prosthetic middle finger having a base and a tip, a prosthetic ring finger having a base and a tip, and a prosthetic pinky finger having a base and a tip. A third actuator may be operably coupled to the upper extremity prosthesis. A third biasing system may be operably coupled to the prosthetic middle finger. A fourth biasing system may be operably coupled to the prosthetic ring finger. A fifth biasing system may be operably coupled to the prosthetic pinky finger. A third prosthetic flexion tendon may have a first end operably coupled to the third actuator and a second end coupled to the tip of the prosthetic middle finger. A fourth prosthetic flexion tendon may have a first end operably coupled to the third actuator and a second end coupled to the tip of the prosthetic ring finger. A fifth prosthetic flexion tendon may have a first end operably coupled to the third actuator and a second end coupled to the tip of the prosthetic pinky finger. Upon actuation of the third actuator in the first direction, the first, second, and third prosthetic flexion tendons may cause the prosthetic middle finger, prosthetic ring finger, and prosthetic pinky finger to flex, respectively, and upon actuation of the third actuator in the second direction, the third, fourth, and fifth biasing systems may cause the prosthetic middle finger, prosthetic ring finger, and prosthetic pinky finger to extend, respectively. A coupling tendon may have a first end operably coupled to the third actuator and a second end coupled to coupling bar at a coupling location, and the third, fourth, and fifth prosthetic flexion tendons may each have the respective first ends coupled to the coupling bar, the coupling bar being rotatable about the coupling location. The coupling tendon and the third, fourth, and fifth prosthetic flexion tendons together may suspend the coupling bar, so that forces applied on the coupling bar by the coupling tendon may be unevenly applied to the third, fourth, and fifth prosthetic flexion tendons.

A prosthetic forearm may be coupled to the prosthetic hand. The prosthetic hand may include an internal volume accessible via an access cover. The first and second actuators may be positioned within the interior volume of the prosthetic hand. A socket may be coupled to the prosthetic forearm, the socket adapted to interface with a residual limb of a user of the upper extremity prosthesis. A force sensor may be coupled to the socket and adapted to provide information to a processor within the upper extremity prosthesis in response to a muscle contraction of the user, the processor adapted to actuate the first and second actuators based on the information. An electromyography sensor may be coupled to the socket and adapted to provide information to a processor within the upper extremity prosthesis in response to a muscle contraction of the user, the processor adapted to actuate the first and second actuators based on the information. A combined sensor may be coupled to the socket, the combined sensor including a force sensor and an electromyography sensor, the combined sensor adapted to provide information to a processor within the upper extremity prosthesis in response to a muscle contraction of the user, the processor adapted to actuate the first and second actuators based on the information.

The prosthetic index finger may include a middle portion positioned between the base and the tip of the prosthetic index finger. The tip of the prosthetic index finger may be rotatable relative to the middle portion of the prosthetic index finger, the middle portion of the prosthetic index finger may be rotatable relative to the base of the prosthetic index finger, and the base of the prosthetic index finger may be rotatable relative to a palm of the prosthetic hand. Upon actuation of the first actuator in the first direction, during a first flexion action the base of the prosthetic index finger may rotate relative to the palm, during a second flexion action the middle portion of the prosthetic index finger may rotate relative to the base of the prosthetic index finger, and during a third flexion action the tip of the prosthetic index finger may rotate relative to the middle portion of the prosthetic index finger. Upon actuation of the first actuator in the first direction, the first flexion action may occur prior to the second flexion action, and the second flexion action may occur prior to the third flexion action.

A prosthetic index fingernail may be adapted to couple to the tip of the prosthetic index finger. In an assembled condition, the prosthetic index fingernail and the tip of the prosthetic index finger may form a substantially closed outer boundary, and in an unassembled condition, the tip of the prosthetic index finger may present an opening to access an interior volume of the tip of the prosthetic index finger. In the assembled condition, the prosthetic index fingernail may be magnetically coupled to the tip of the prosthetic index finger.

The base of the prosthetic thumb may be coupled to the prosthetic hand via a pin, and the prosthetic thumb may be rotatable about the pin between a first rotational position and a second rotational position. A locking pin may lock the prosthetic thumb in the first rotational position and in the second rotational position in the absence of rotational force being applied to the prosthetic thumb.

BRIEF DESCRIPTION OF THE DRAWINGS

FIGS. 8A-E are views of a forearm cover component of the prosthetic forearm of FIGS. 6A-E.

DETAILED DESCRIPTION

Figure 1A:
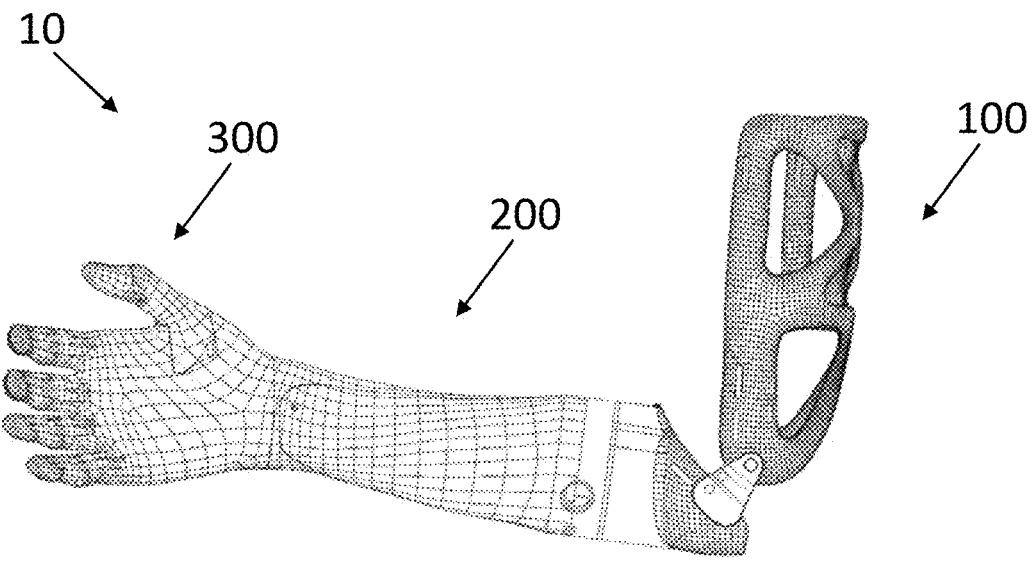
FIGS. 1A-C are views of a prosthetic upper extremity according to an aspect of the disclosure.
Figure 1B:
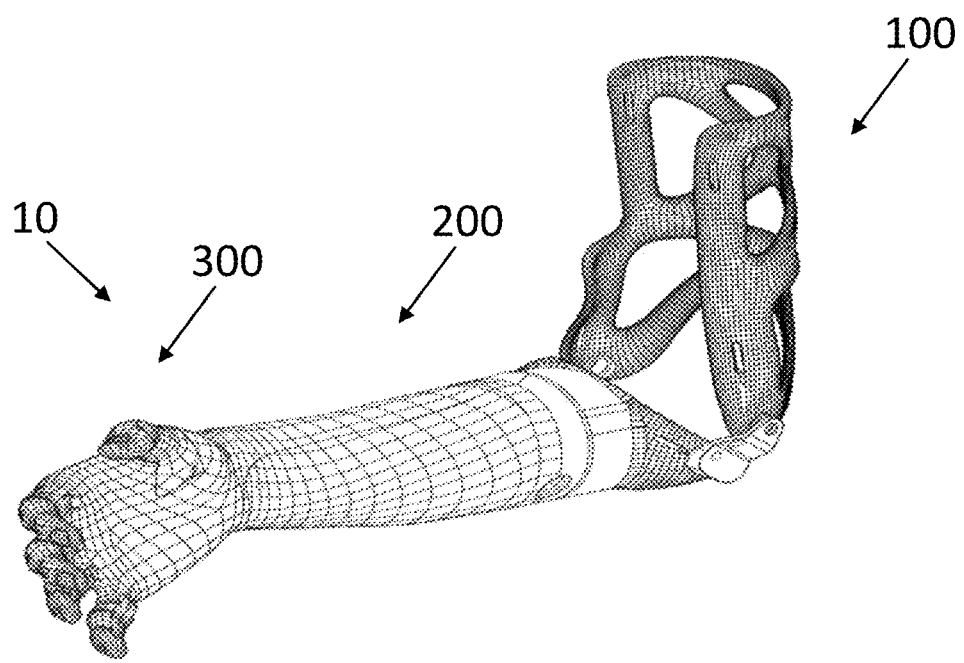
Figure 1C:
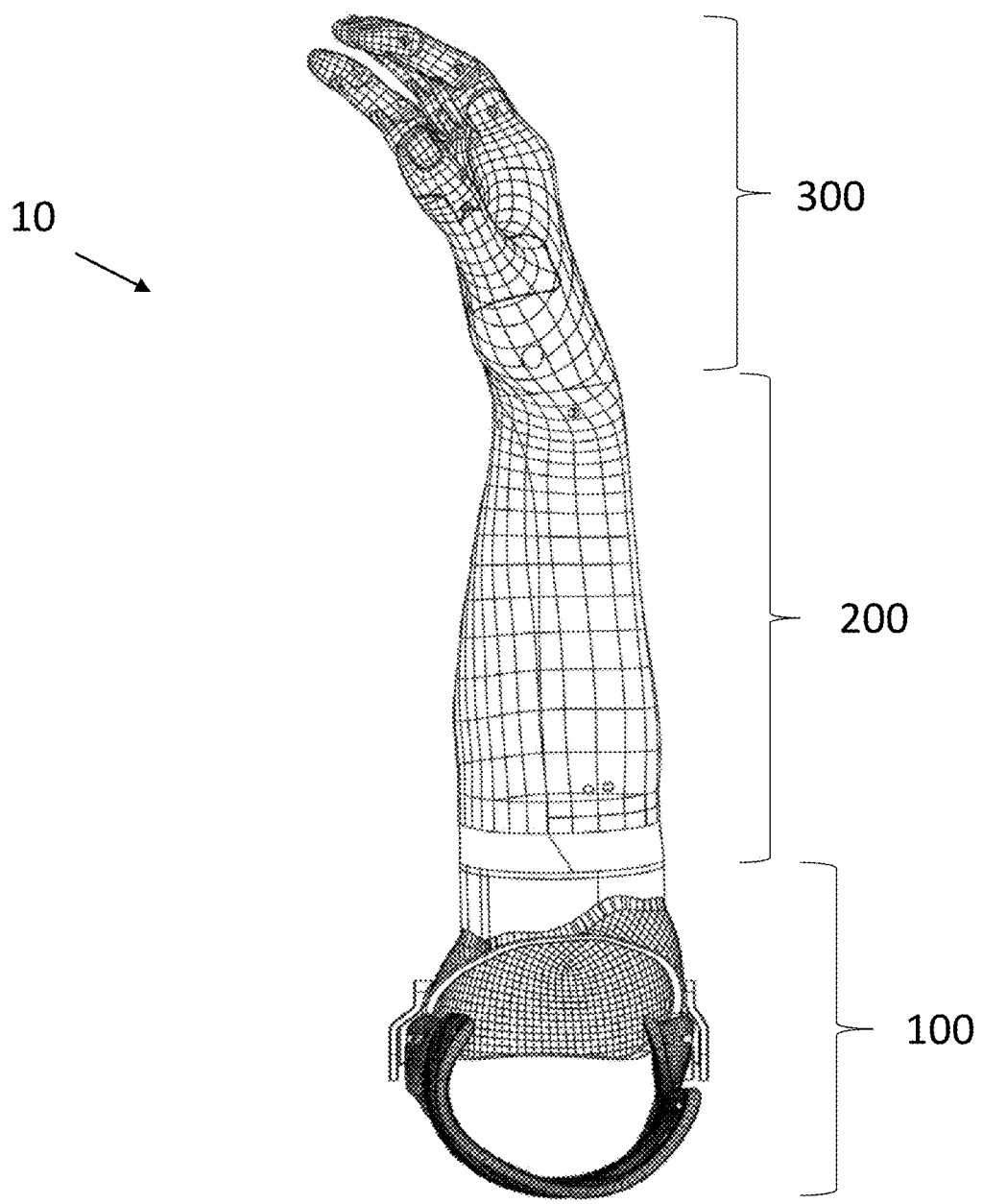

FIGS. 1A-C show an embodiment of a prosthetic upper extremity 10 for use in humans. Generally, prosthetic upper extremity 10 may include a socket 100, a prosthetic forearm 200, and a prosthetic hand 300, each of which is described in greater detail below. It should be understood that the illustrated prosthetic upper extremity 10 is for a right side of a user, but a substantially identical prosthetic upper extremity could be used for the left side of a user, with the features of the left side prosthetic extremity being substantially a mirror image of the illustrated right side prosthetic upper extremity 10.

Figure 2A:
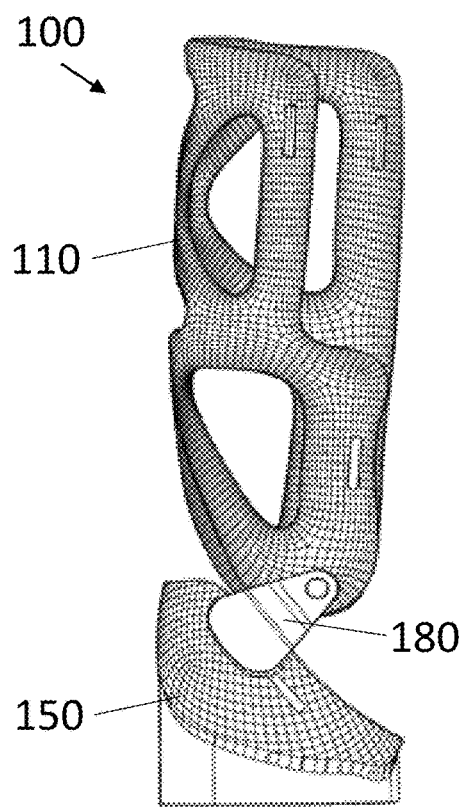
FIGS. 2A-C are views of a socket of the prosthetic of FIGS. 1A-C.
Figure 2B:
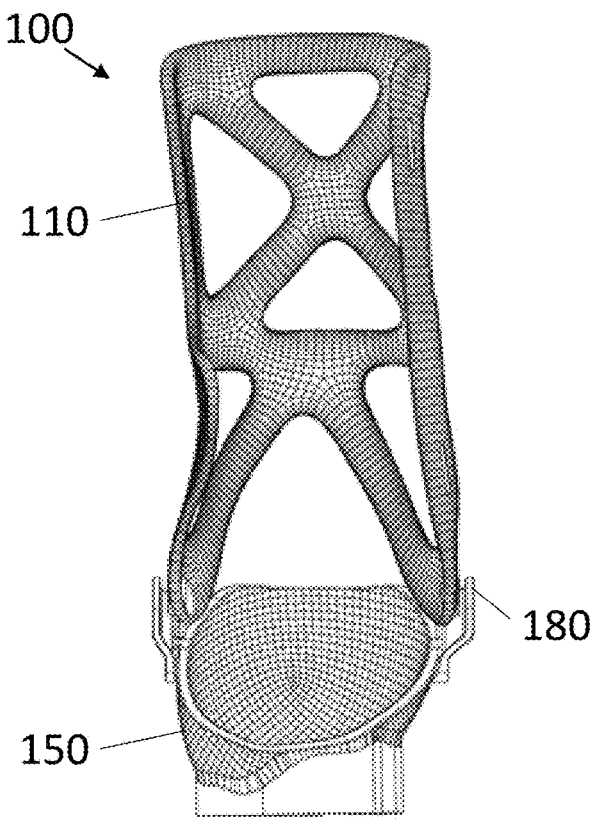
Figure 2C:
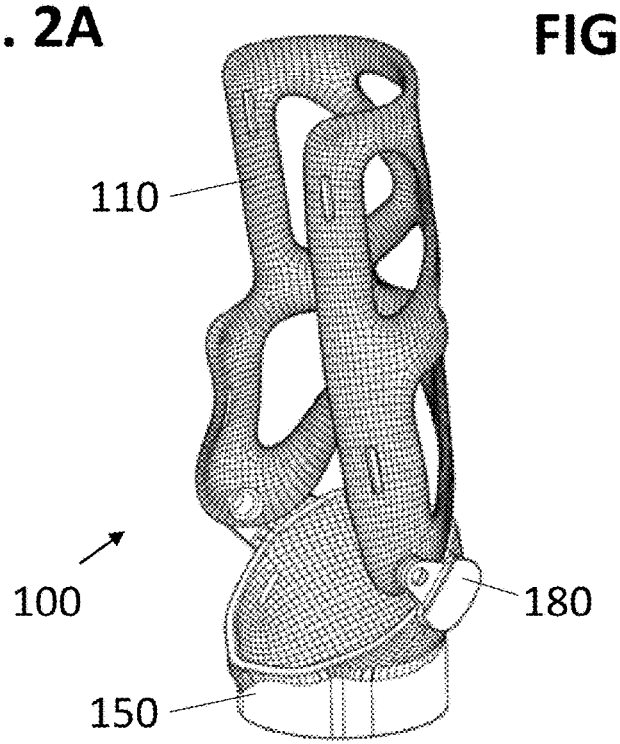

FIGS. 2A-C show an embodiment of socket 100, which may generally function to couple the user's residual limb to the prosthetic forearm 200. Generally, socket 100 is a rigid member that matches the shape and contours of the user's residual limb, and may be attached to the residual by a compression fit or other suitable mechanism. In the illustrated embodiment, socket 100 includes a proximal socket 110 and a distal socket 150, the proximal socket 110 and distal socket 150 being coupled by a joint 180. As used herein, the term "proximal" refers to a portion of the prosthetic upper extremity 10 that is relatively close to the user's heart when being used as intended, while the term "distal" refers to a portion of the prosthetic upper extremity 10 that is relatively far from the user's heart when being used as intended.

Figure 3A:
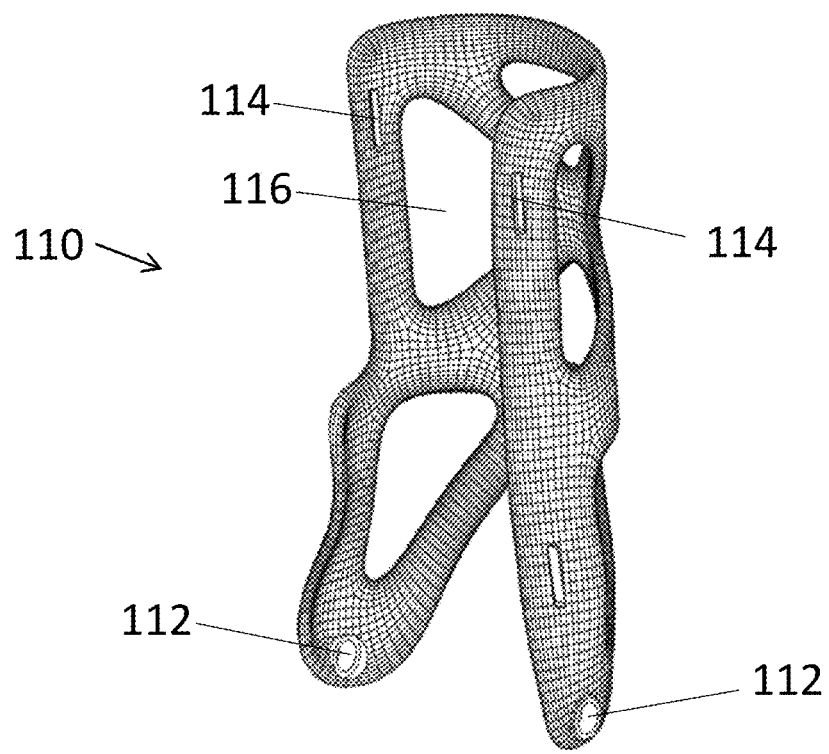
FIGS. 3A-B are views of a proximal socket of the socket of FIGS. 2A-C.
Figure 3B:
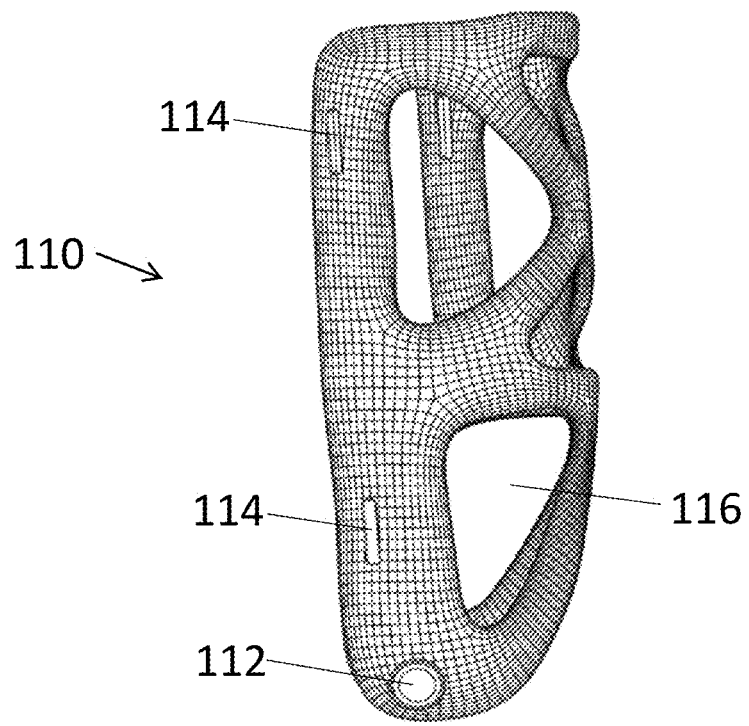

FIGS. 3A-B show two views of one embodiment of the proximal socket 110. Proximal socket 110 is preferably formed of a single integral member. Proximal socket 110 may be intended to fit over or otherwise couple to a user's upper arm, such as the bicep area proximal to the user's elbow joint. A proximal portion of proximal socket 110 is preferably generally "C"- or "U"-shaped in transverse cross-section. A distal portion of proximal socket 110 may also be generally "C"- or "U"-shaped in transverse cross-section, and may include one or more apertures 112. The distal end of proximal socket 110 preferably includes two apertures 112 that function to couple the proximal socket 110 to the distal socket 150 via joint 180. A plurality of slots 114 may also be provided on proximal socket 110. As illustrated, the proximal portion of proximal socket 110 includes a pair of slots 114 oriented substantially longitudinally near the ends of the "C"- or "U"-shape. The distal portion of proximal socket 110 is also illustrated as including a second pair of slots 114 with similar positioning. Slots 114 may be shaped and positioned to receive a strap or other coupling member. For example, a strap with a hook-and-loop fastener such as VELCRO® brand straps may be used with each pair of slots 114, with the straps helping attach and secure the proximal socket 110 to the bicep area of the user's residual limb. One or more voids 116 may be provided in proximal socket 110, regardless of whether proximal socket 110 is formed as a single integral member. Voids 116 may be areas where material has been actively removed during a stage of manufacture, or the voids 116 may be formed passively by forming proximal socket 110 to define voids 116. Regardless, voids 116 may provide one or more benefits, including reducing the weight of proximal socket 110, increasing air flow to the user and/or increasing comfort of the proximal socket 110, and/or increasing the duration of use of proximal socket 110. It should be understood that, although voids 116 are illustrated as having certain positions and shapes and being provided in certain numbers, other numbers and/or positions and/or shapes of voids 116 may be suitable.

Proximal socket 110 includes an interior surface adapted to directly or indirectly couple to the user's upper arm. Preferably, the interior surface is user-specific in the sense that it is shaped and contoured to match the shape of the portions of the user's upper arm that will contact the interior surface of the proximal socket 110. A pre-determined offset may be introduced into proximal socket 110. In other words, rather than produce proximal socket 110 to include an interior surface that exactly matches the contours of the user's upper arm, the surface may be offset a fixed distance to allow for foam or other compressible or moldable material to be positioned as an interface between the user's upper arm and the interior surface of the proximal socket 110. The thickness of the foam or other interference material may be equal or substantially equal to the amount of fixed distance offset.

FIGS. 4A-D show various views of one embodiment of the distal socket 150.

Distal socket 150 may generally include a coupling portion 160 for directly or indirectly attaching to the residual limb of a user, and a linking portion 170 for coupling to prosthetic forearm 200. Coupling portion 160 preferably has user-specific shape and/or contours so that the coupling portion closely matches the portion of the user's residual limb that it will contact. Similar to above, an offset may be introduced into the contact surface of the coupling portion 160 in order to account for one or more additional interface layers, such as foam or another compressible or moldable material, which will be positioned between the user's residual limb and the interior surface of coupling portion 160. Coupling portion 160 may include one or more slots 164. Preferably, a pair of slots 164 are included on substantially opposite sides of the coupling portion 160 to receive a strap or other device to help better secure distal socket 150 to the user's residual limb.

Figure 5:
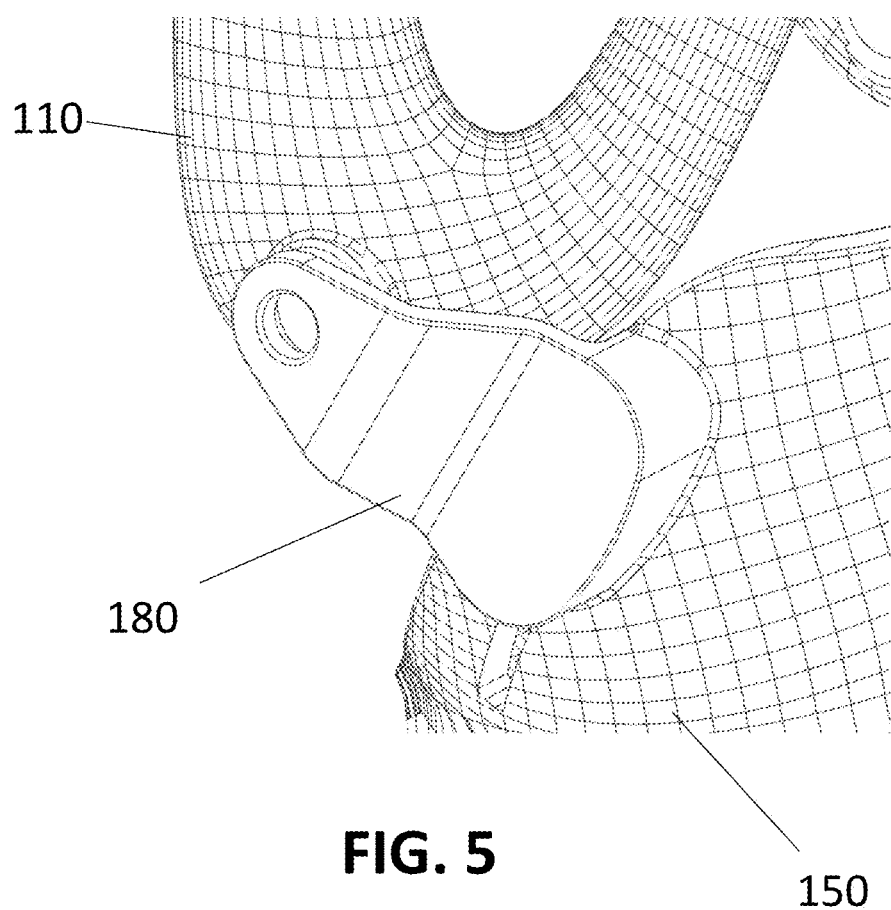
FIG. 5 is an enlarged view of a hinge of the socket of FIGS. 2A-C.

A joint 180 may be coupled to distal socket 150, preferably to coupling portion 160. Joint 180 may include two bracket members on substantially opposite sides of the coupling portion. The bracket members of joint 180 may include apertures or other structures to couple the brackets to the apertures 112 in proximal socket 110, for example via pins so that joint 180 may rotate about an axis extending through apertures 112 of proximal socket 110. FIG. 5 illustrates proximal 110 coupled to distal socket 150 via joint 180. The joint 180 preferably substantially aligns with the elbow joint of the user so that, as the user rotates his or her residual forearm relative to the upper arm via the elbow, the proximal socket 110 correspondingly rotates relative to the distal socket 150.

Figure 4A:
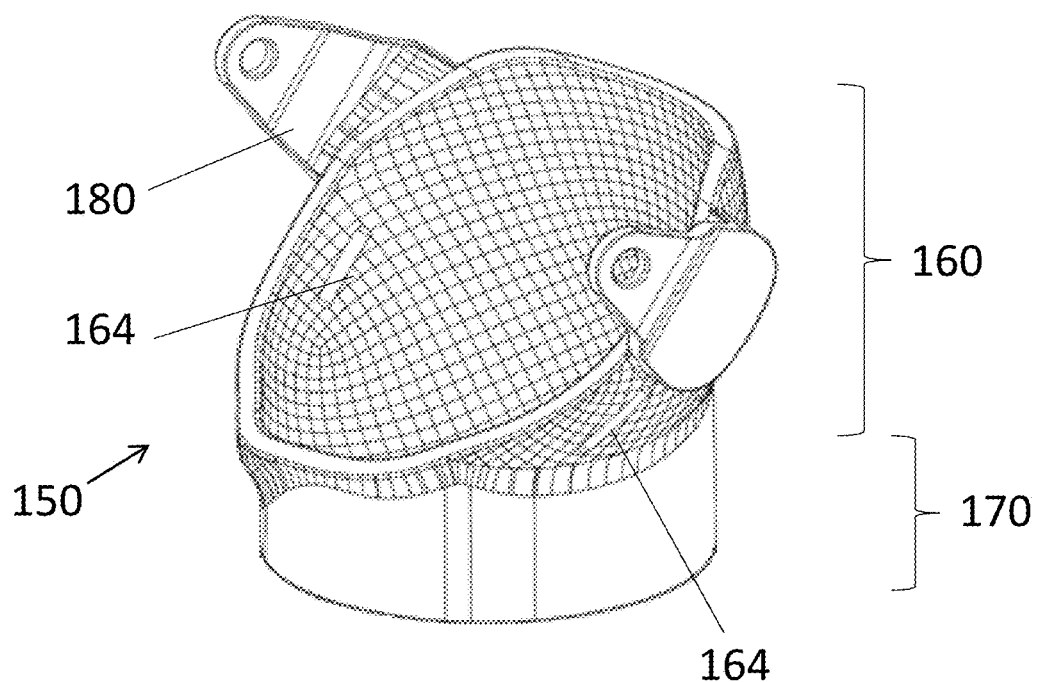
FIGS. 4A-D are views of a distal socket of the socket of FIGS. 2A-C.
Figure 4B:
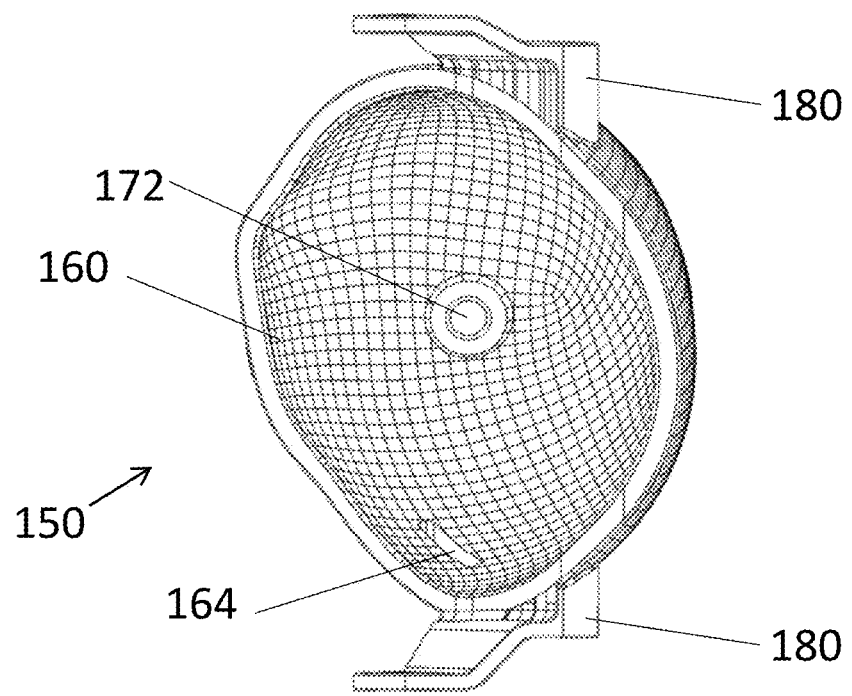
Figure 4C:
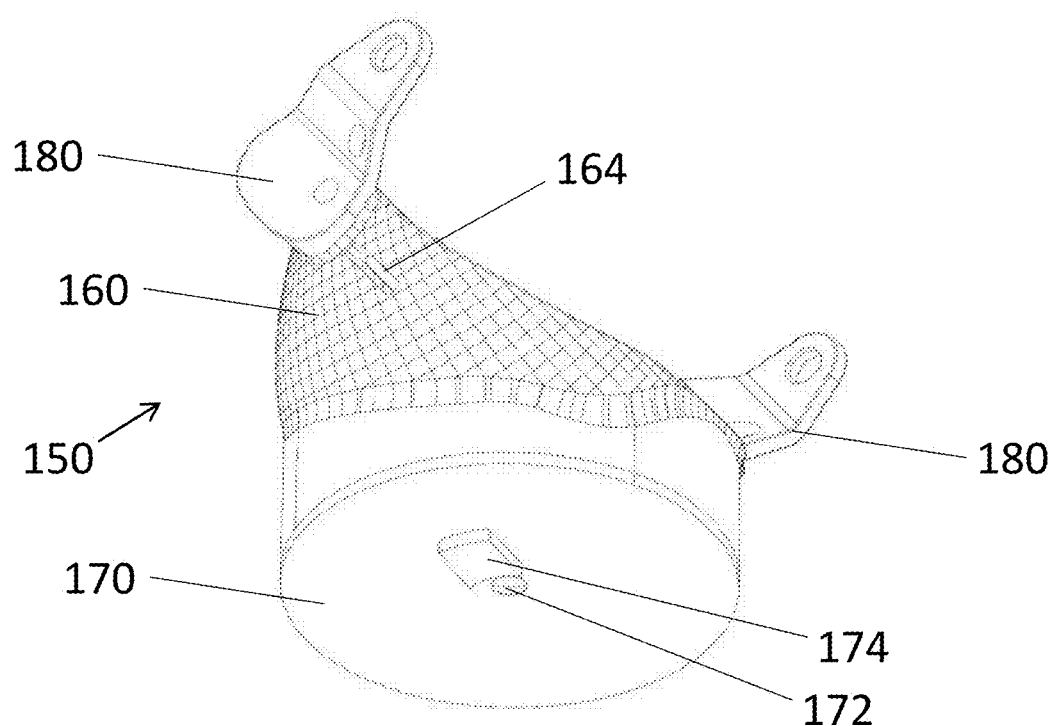
Figure 4D:
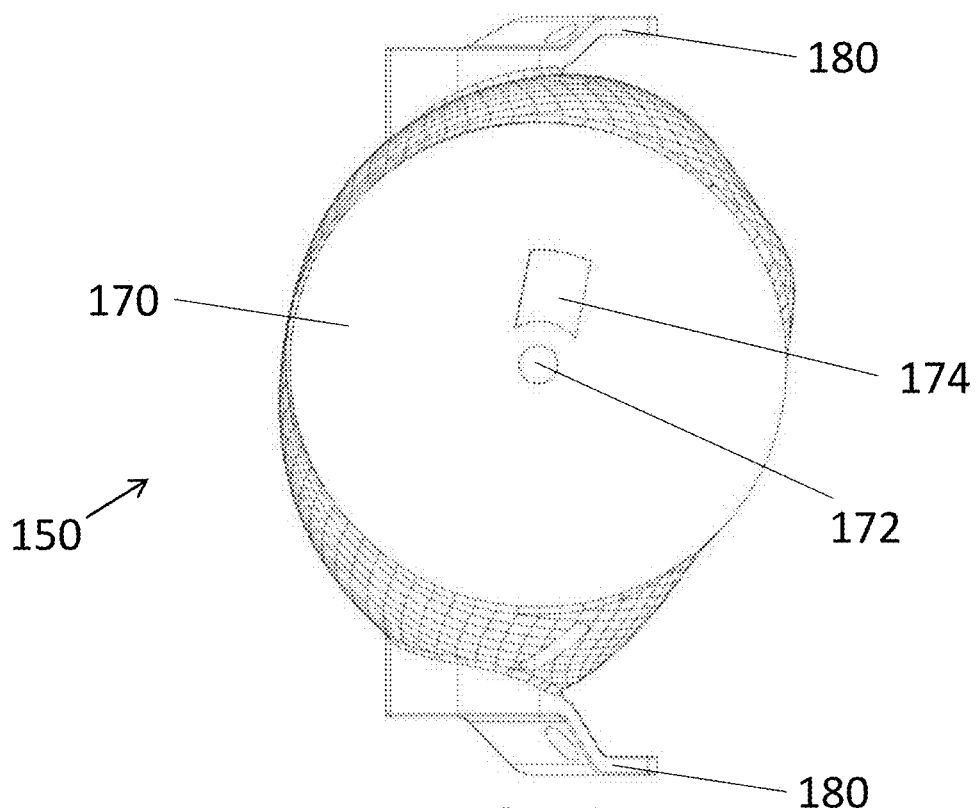

Linking portion 170 may extend distally from coupling portion 160, the linking portion being substantially cylindrical. As best shown in FIGS. 4C-D, a distal surface of linking portion 170 may include an aperture 172, preferably at a longitudinal center of the cylinder, and a protrusion 174 extending from the distal surface. Aperture 172 and protrusion 174 may help link distal socket 150 to prosthetic forearm 200, as described in greater detail below.

FIGS. 6A-E show various views of prosthetic forearm 200 in an assembled condition. Generally, prosthetic forearm may include a main forearm 210 and a forearm cover 260. In the assembled condition, prosthetic forearm 200 may have a shape, size, contour, color, and/or texture that substantially is a mirror image of the user's remaining forearm, if such a forearm exists. Methods for creating prosthetic forearm 200 are described in greater detail below after the remaining structures and functions of upper prosthetic extremity 10 are described. In the illustrated embodiment, main forearm 210 houses most or all of the mechanical components that cause movement of the prosthetic hand 300, while cover 260 houses most or all of the electronic components that control the mechanical components, as described in greater detail below. However, in other embodiments, prosthetic forearm 200 may serve mostly or solely as a structural member that couples the prosthetic hand 300 to the socket 100, with most or all of the electronic and/or mechanical components being housed within prosthetic hand 300.

Figure 7A:
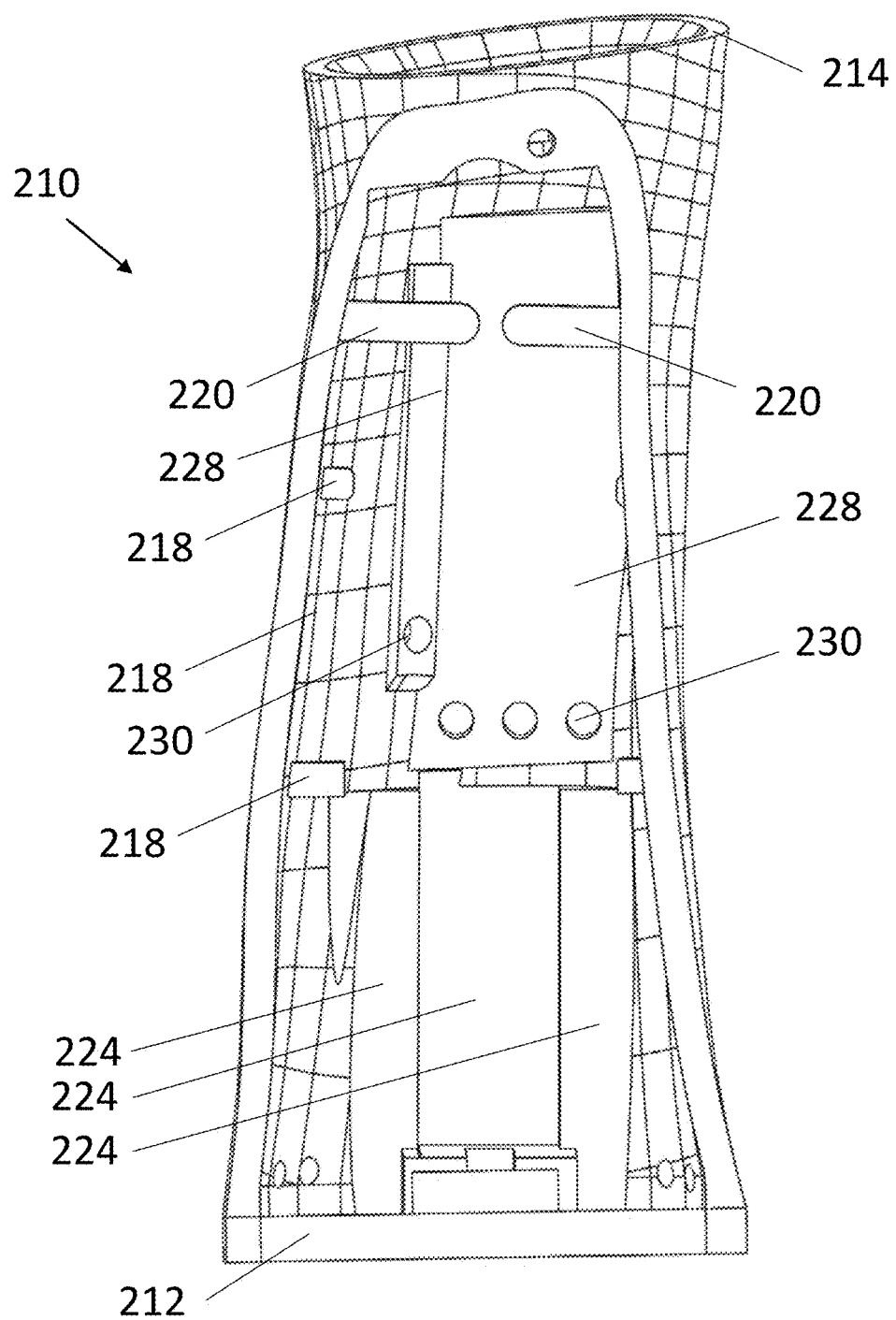
FIGS. 7A-E are views of a main forearm component of the prosthetic forearm of FIGS. 6A-E.
Figure 7B:
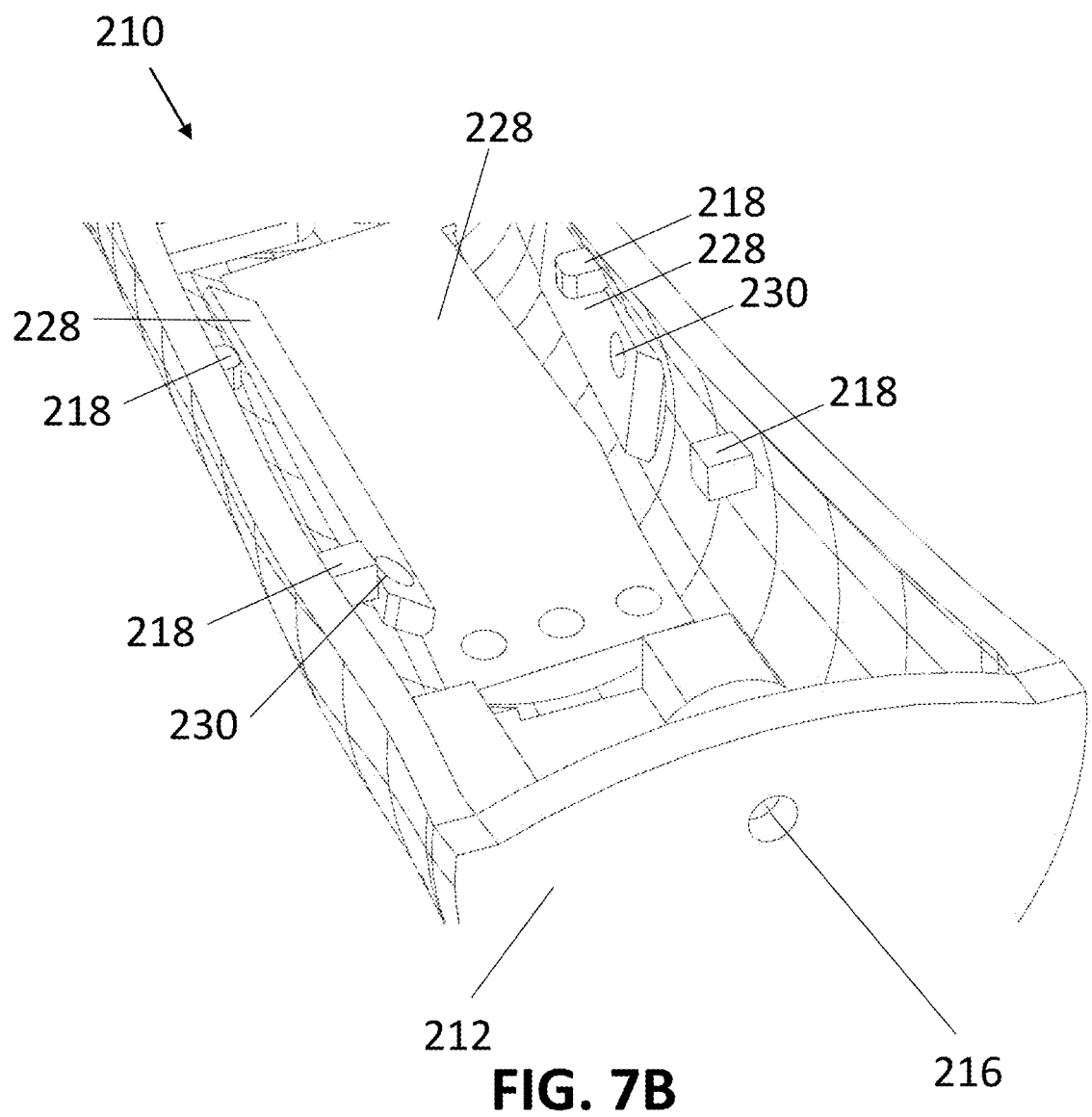
Figure 7C:
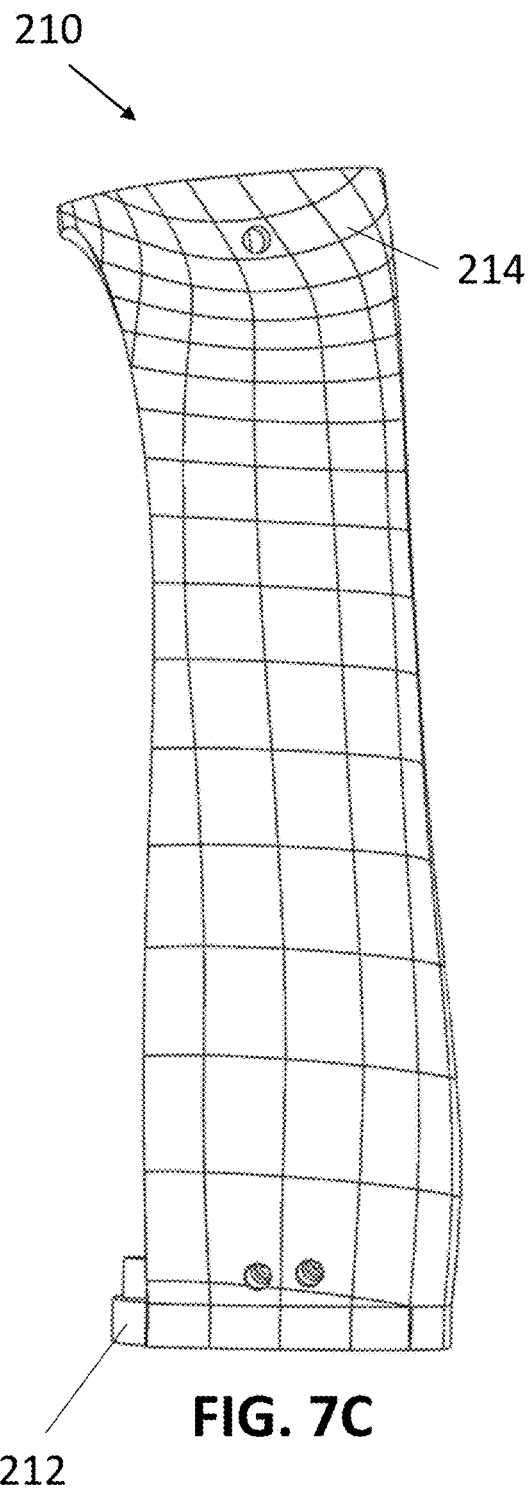
Figure 7D:
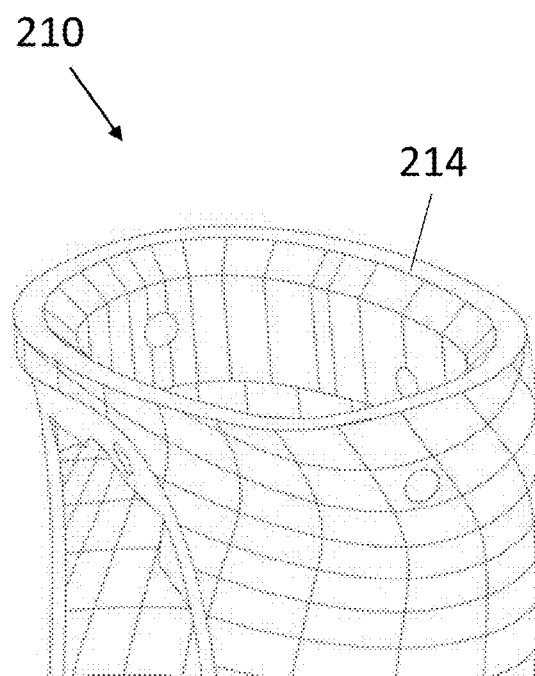

FIGS. 7A-E illustrate various views of the main forearm 210 of prosthetic forearm 200. Main forearm 210 may extend from a proximal base 212 to a distal wrist 214. As noted above and explained in greater detail below, main forearm 210 may include a substantially closed outer portion that preferably is substantially a mirror image of the user's remaining forearm. Main forearm 210 may be substantially hollow with an interior compartment to receive components, such as mechanical components to allow for movement of the prosthetic hand 300. Distal wrist 214, an illustrative shape of which is illustrated in FIGS. 7C-D, may include apertures or other features to facilitate coupling the prosthetic hand 300, described in greater detail below, to the main forearm 210. However, in other embodiments, the palm of the prosthetic hand 300 may be integral with the main forearm 210.

Figure 7E:
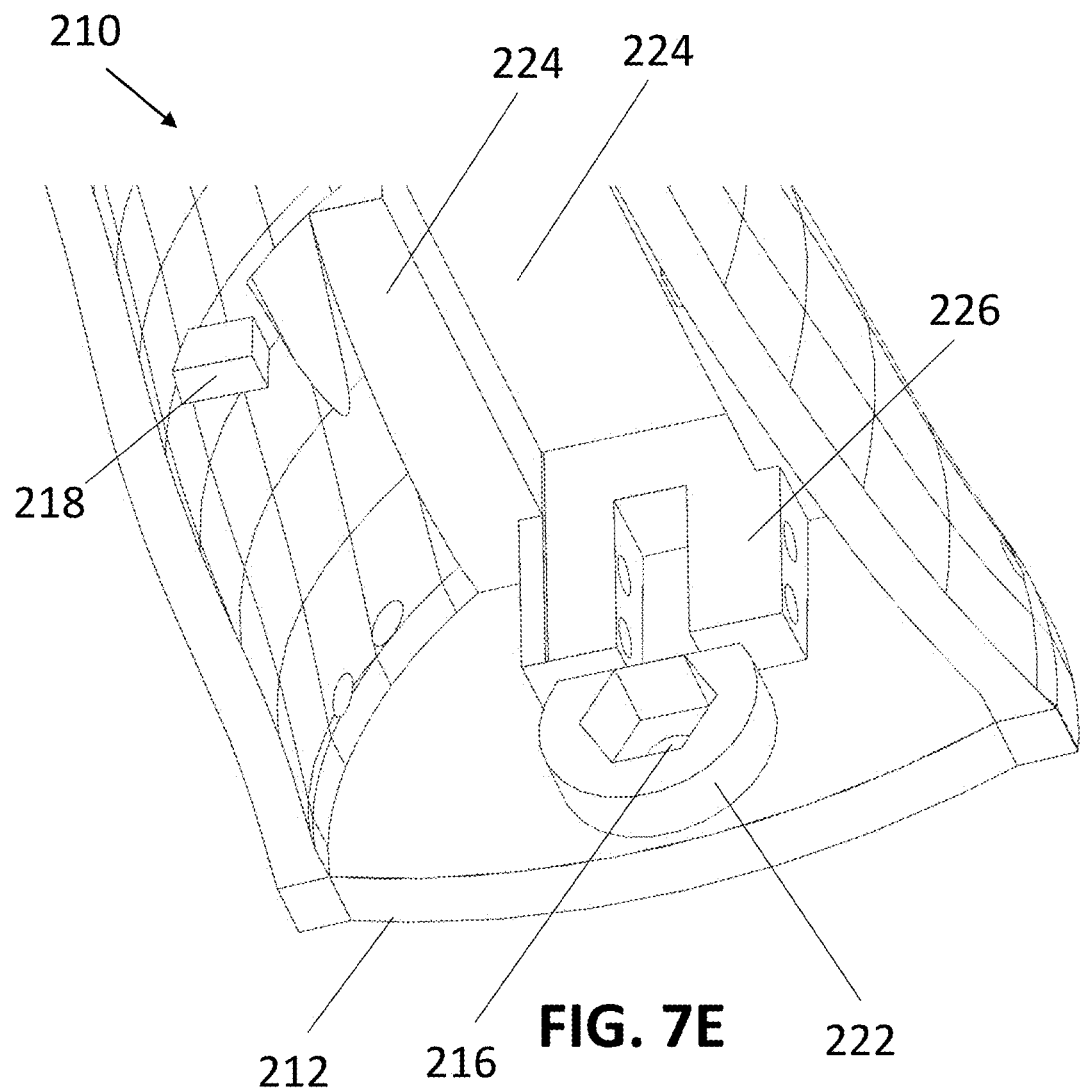

The proximal base 212 of main forearm 210, which is best shown in FIGS. 7A-B and 7E, may help couple the main forearm 210 to the cover 260 and the distal socket 150, for example via an aperture 216. Base 212 may form a portion of a cylinder, with aperture 216 preferably positioned near the center of that cylinder. In the illustrated embodiment, a nut housing 222 may be positioned around aperture 216 to receive a nut therein, so that a bolt passing through aperture 216 passes through the nut in in nut housing 222, with the nut housing 222 preventing the nut from rotating. A plurality of tabs 218 may project from an interior surface of main forearm 210 and may assist in keeping electronic components within cover 260 separated from mechanical components within main forearm 210. In some embodiments, a plate or other cover may sit on or attach to tabs 218 to cover the springs and prosthetic tendons (described in greater detail below) to help ensure the prosthetic tendons do not become ensnared on other components of the system. As shown in FIG. 7A, a pair of tabs 220 may extend toward one another substantially the entire distance of the opening near distal wrist portion 214. As will become evident in the description below, tabs 220 may help guide and retain prosthetic tendons extending toward and through distal wrist portion 214, as well as help separate electronic components within cover 260 from the mechanical components of main forearm 210.

The interior surface of main forearm 210 may include a number of structures to facilitate positioning and fixation of mechanical components therein. For example, as best shown in FIG. 7A, a plurality of flat surfaces 224 may be provided on the interior surface of main forearm 210 to provide a surface for positioning a flat surface of an actuator. In one example, three flat surfaces 224 may be provided for contacting the flat surfaces of three corresponding linear actuators. As best shown in FIG. 7E, a support member 226 may be provided to help secure the actuators to the main forearm 210. In the illustrated embodiment, the support member may include two prongs with apertures, and one actuator may be positioned between the two prongs, and an actuator may be positioned on the outside of each prong. In this embodiment, the actuators may include apertures so that one or more pins may pass through the bodies of the actuators and the apertures of the support member 226 to fix the actuators to the support member 226 of the main forearm 210. Additional apertures or other structures may be included in the wall of the main forearm 210 in order to further secure the actuators to the main forearm 210. As is described in greater detail below, each actuator may be a linear actuator coupled to a prosthetic tendon routed to one or more of the prosthetic fingers, the linear actuators adapted to cause flexion of the prosthetic fingers.

Referring to FIGS. 7A-B, additional flat surfaces 228 may be provided distal to surface 224, with a plurality of apertures 230 provided therein. In the illustrated embodiment, five total apertures 230 are provided on three flat surfaces 228. Each aperture 230 may facilitate coupling a spring or other tension member to the main forearm 210, for example by screwing the tension member into the aperture 230. As is described in greater detail below, prosthetic tendons may be coupled to each tension member, with one prosthetic tendon extending from each tension member to a corresponding finger or thumb in order to cause the fingers to extend in the absence of applied forces other than the tension member. It should be understood that the tension members may be coupled to main forearm 210 with structures and configurations other than the three flat surface 228 and five corresponding apertures 230.

Figure 8A:
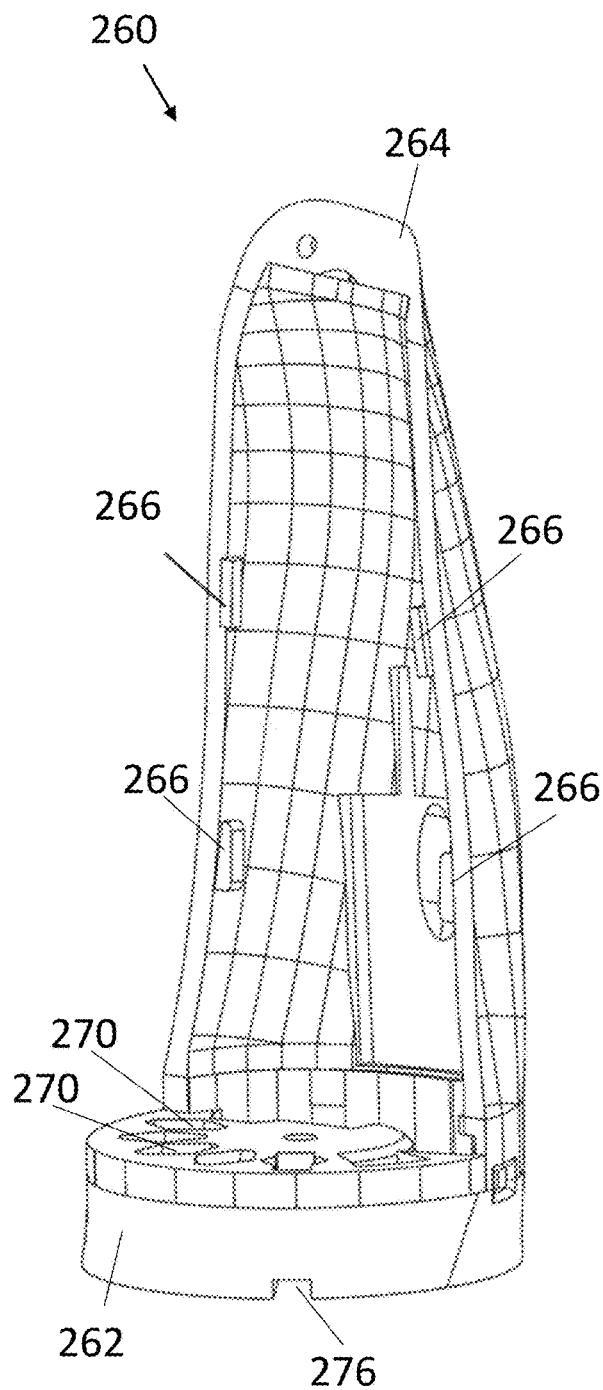

FIGS. 8A-E illustrate various views of cover 260. Cover 260 may extend from a proximal base 262 to a distal end 264. Cover 260 may include an exterior surface that, when coupled to main forearm 210, substantially replicates a mirror image of the user's remaining forearm. Cover 260 may be shaped and contoured so that it can only interface with main forearm 210 in one or substantially one orientation. One or more tabs 266 may protrude from an interior surface of cover 260. Tabs 266 are best illustrated in FIG. 8E. In the assembled condition of prosthetic forearm 200, each tab 266 of cover 260 may be in contact with a corresponding tab 218 of main forearm 210. Tabs 266 may also help separate mechanical components within main forearm 210 from electronic components within cover 260. Distal end 264 of cover 260 may include an aperture that aligns with a corresponding aperture near distal wrist 214 (best seen in FIG. 7A) in the assembled condition of the prosthetic forearm 200, the apertures adapted to receive a fastener therethrough to further secure the cover 260 to the main forearm 210.

The base 262 of cover 260 may function to couple prosthetic forearm 200 to distal socket 150, and the help secure main forearm 210 to both cover 260 and distal socket 150. In the illustrated embodiment, base 262 is substantially cylindrical and includes a central aperture 268 that substantially aligns with central aperture 216 of the base 212 of main forearm 210, as well as aperture 172 of the linking portion 170 if distal socket 150. Prior to describing the coupling of prosthetic forearm 200 to distal socket 150, additional structures of cover 260 are described.

Figure 8B:
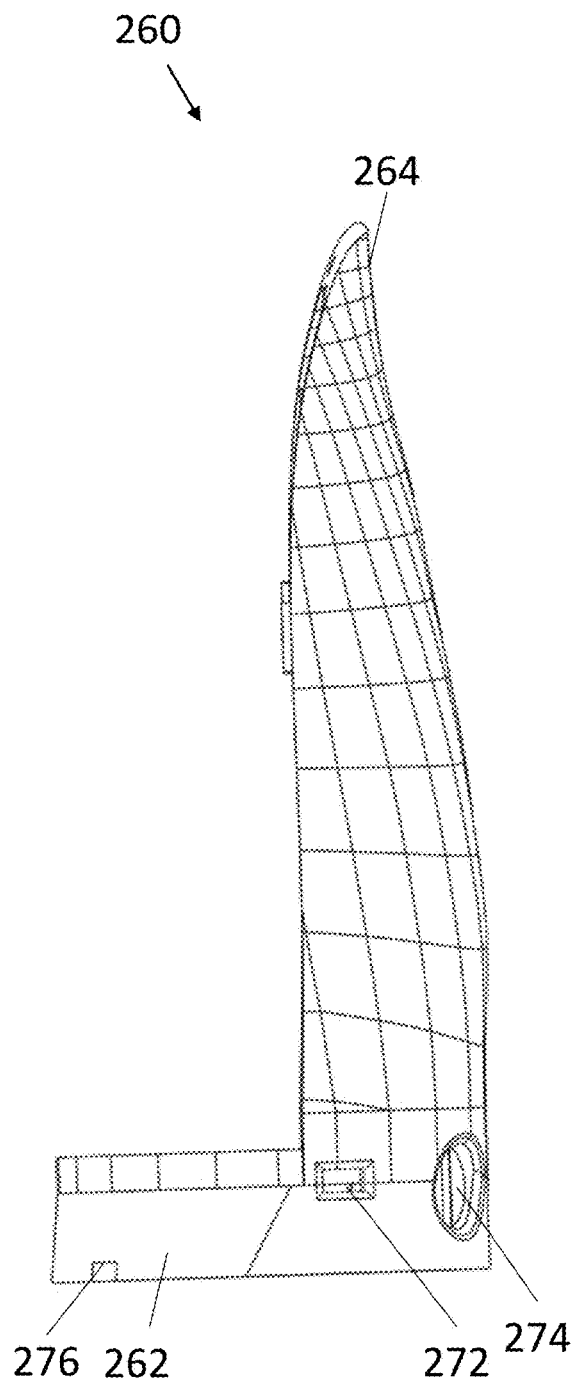
Figure 8C:
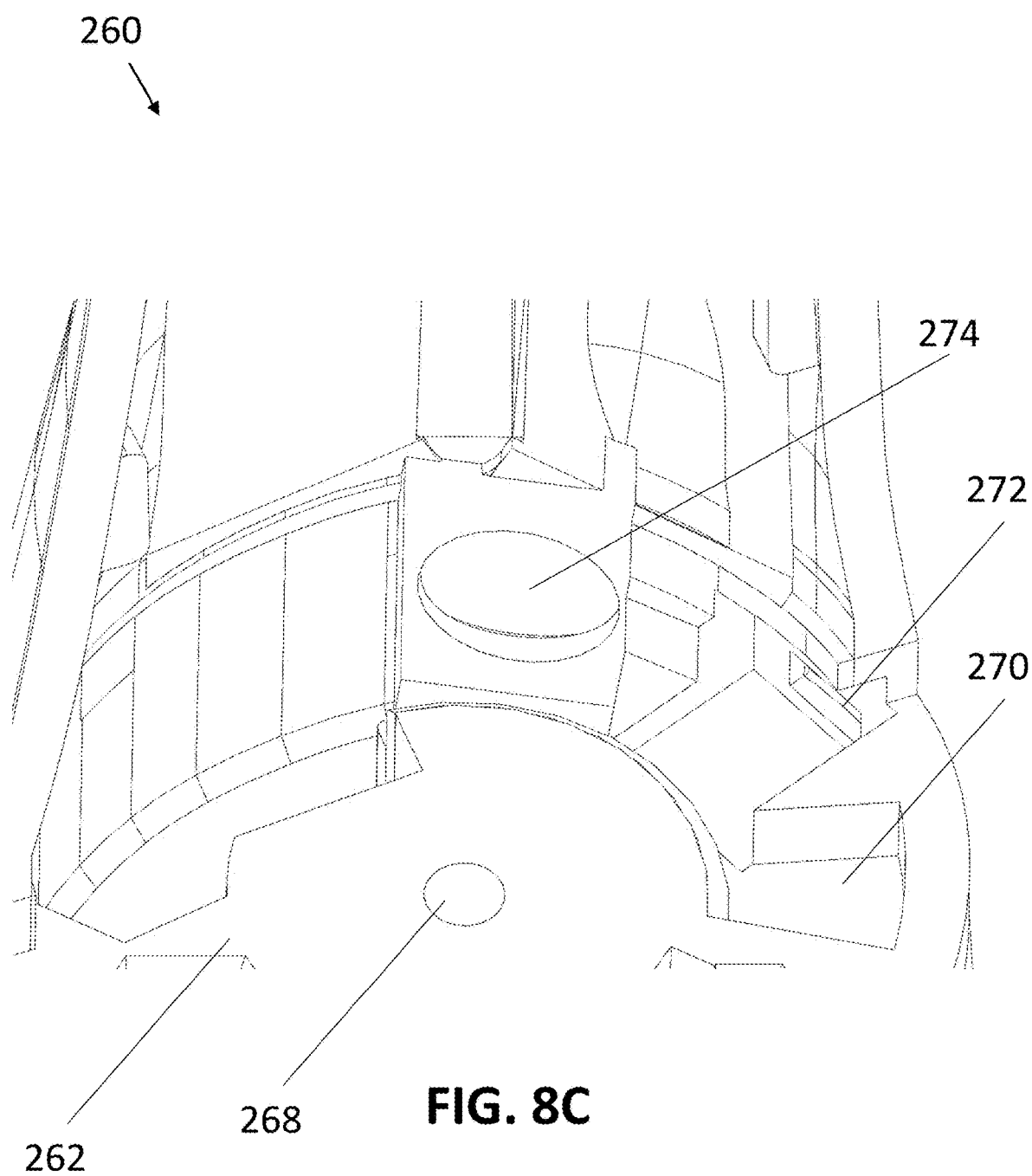

As best shown in FIGS. 8A and 8C, base 262 of cover 260 may include a plurality of cut-outs or other recesses 270 in order to reduce the material used in creating cover 260. As best shown in FIG. 8B, a first recess 272 may be provided in an exterior surface of cover 260. Recess 272 may be sized to receive a button that connects to electronic components housed in cover 260. The button in recess 272 may act as a power button or switch to turn the power to the prosthetic upper extremity on or off. A second recess 274 may be provided in an exterior surface of cover 260. Recess 274 may be sized to receive another button that connects to electronic components housed in cover 260. The button in recess 274 may provide any one or more of various functions described in greater detail below. Additional ports may be provided as desired, including for example ports to charge one or more batteries within prosthetic forearm 200.

Referring to FIGS. 8A-B, base 262 may include an indentation 276 in a bottom surface thereof. When base 262 is coupled to distal socket 150, indentation 276 may provide an area through which one or more cables may extend in order to couple electronic components within cover 260 to sensors within socket 100 or any other components as desired. Indentation 276 may provide a continuous pathway to the interior of prosthetic forearm 200 in the assembled condition, for example via one of the recesses 270 in base 262. In the assembled condition of prosthetic forearm 200, as described in greater detail below, base 262 of cover 260 may be positioned proximal to base 212 of main forearm 210, so that the base 262 of the cover 260 serve as the base for the assembled prosthetic forearm 200. This is shown best in FIG. 6D which illustrates a bottom view of assembled prosthetic forearm 200. In this view, indentation 262 is shown leading to recess 270 to allow for cables or other wires to pass from within prosthetic forearm 200 to a position external to the prosthetic forearm.

Figure 6A:
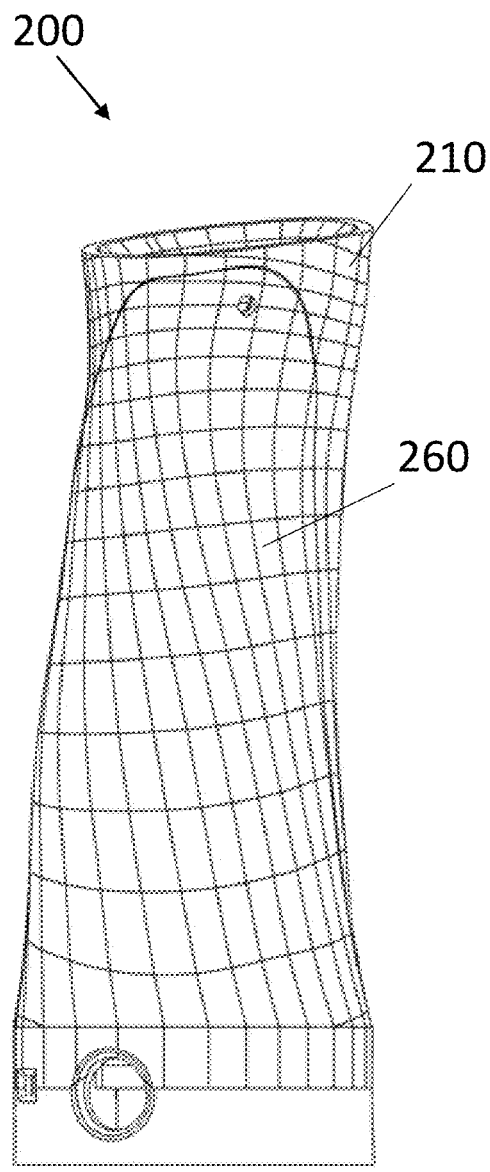
FIGS. 6A-E are views of a prosthetic forearm of the prosthetic extremity of FIGS. 1A-C in an assembled condition.
Figure 6B:
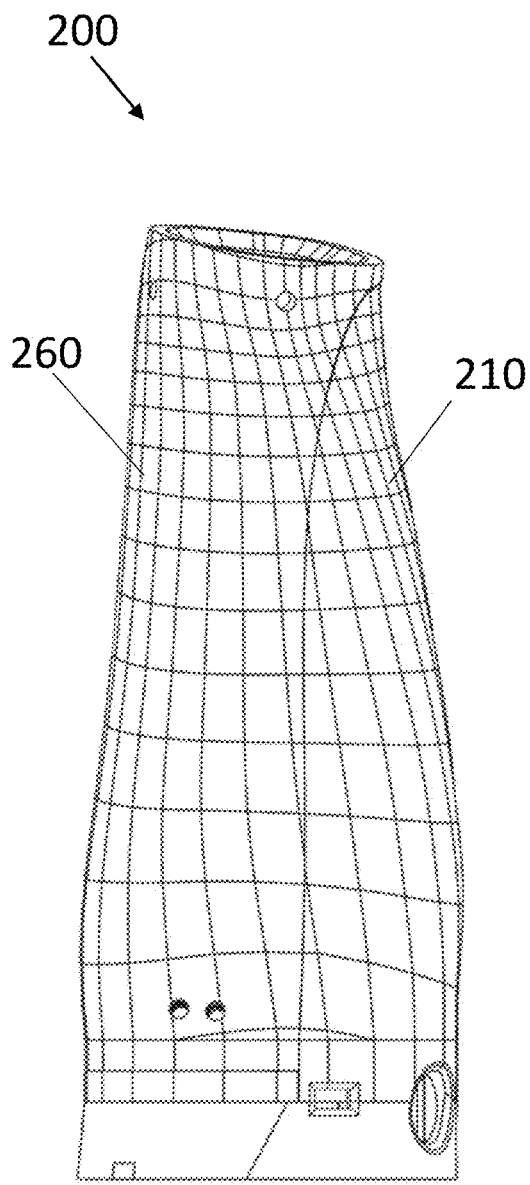
Figure 6C:
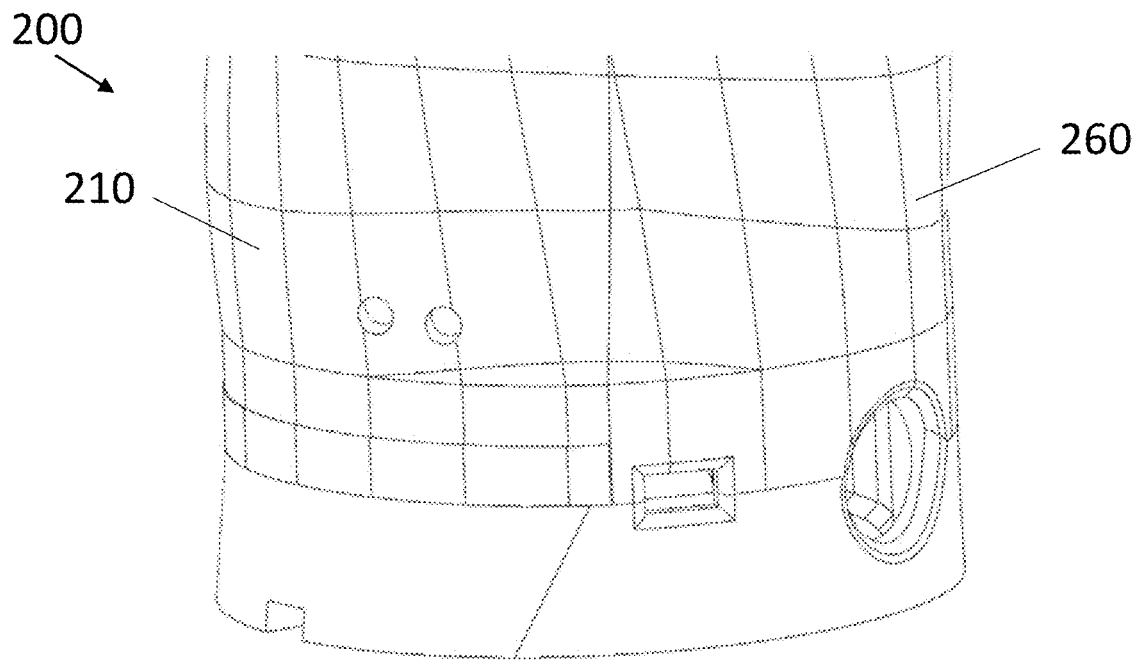
Figure 6D:
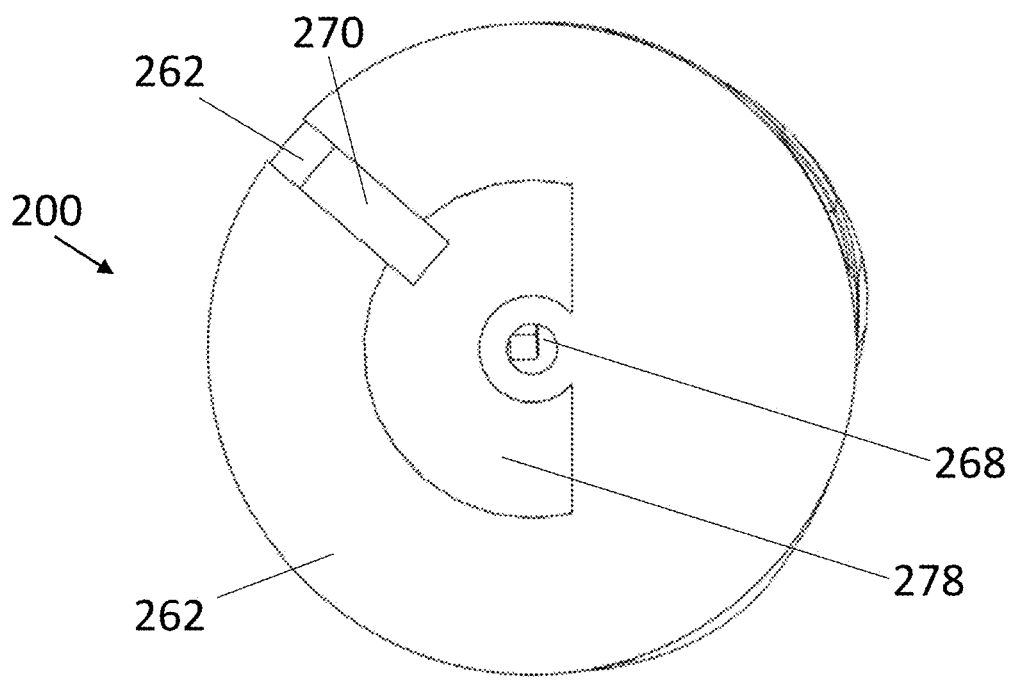
Figure 6E:
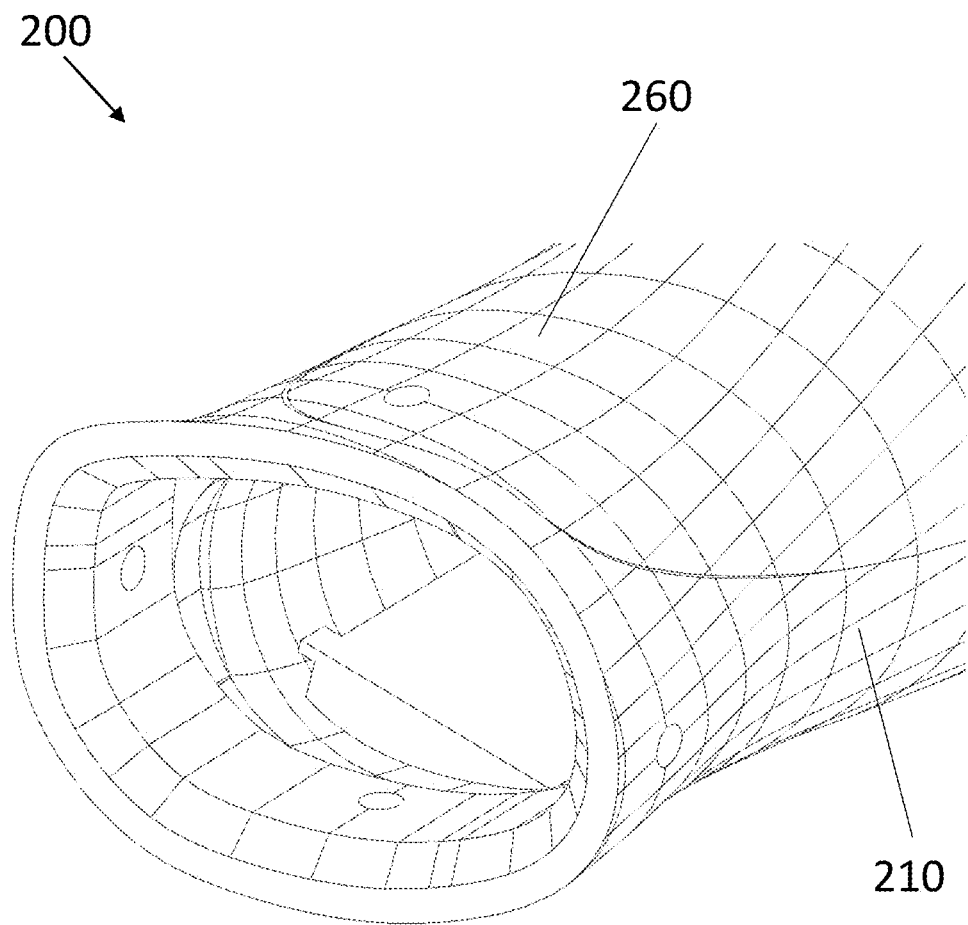

Still referring to FIG. 6D, a bottom surface of base 262 of cover 260 may include an semi-circular or semi-annular recess 278 shaped and positioned to receive the protrusion 174 of linking portion 170 therein. Thus, when the prosthetic forearm 200 is coupled to the socket 100, prosthetic forearm 200 may rotate with respect to distal socket 150. In the illustrated embodiment, semi-annular recess 278 may provide for about 180 degrees of rotation, although it should be understood that the recess 278 may be shaped to provide a greater or smaller amount of rotation. In some embodiments, the recess 278 and/or protrusion 174 may be omitted. In the illustrated embodiment, rotation between prosthetic forearm 200 and distal socket 150 may be performed manually, although in other embodiments automated or semi-automated rotation may be provided.

Figure 9:
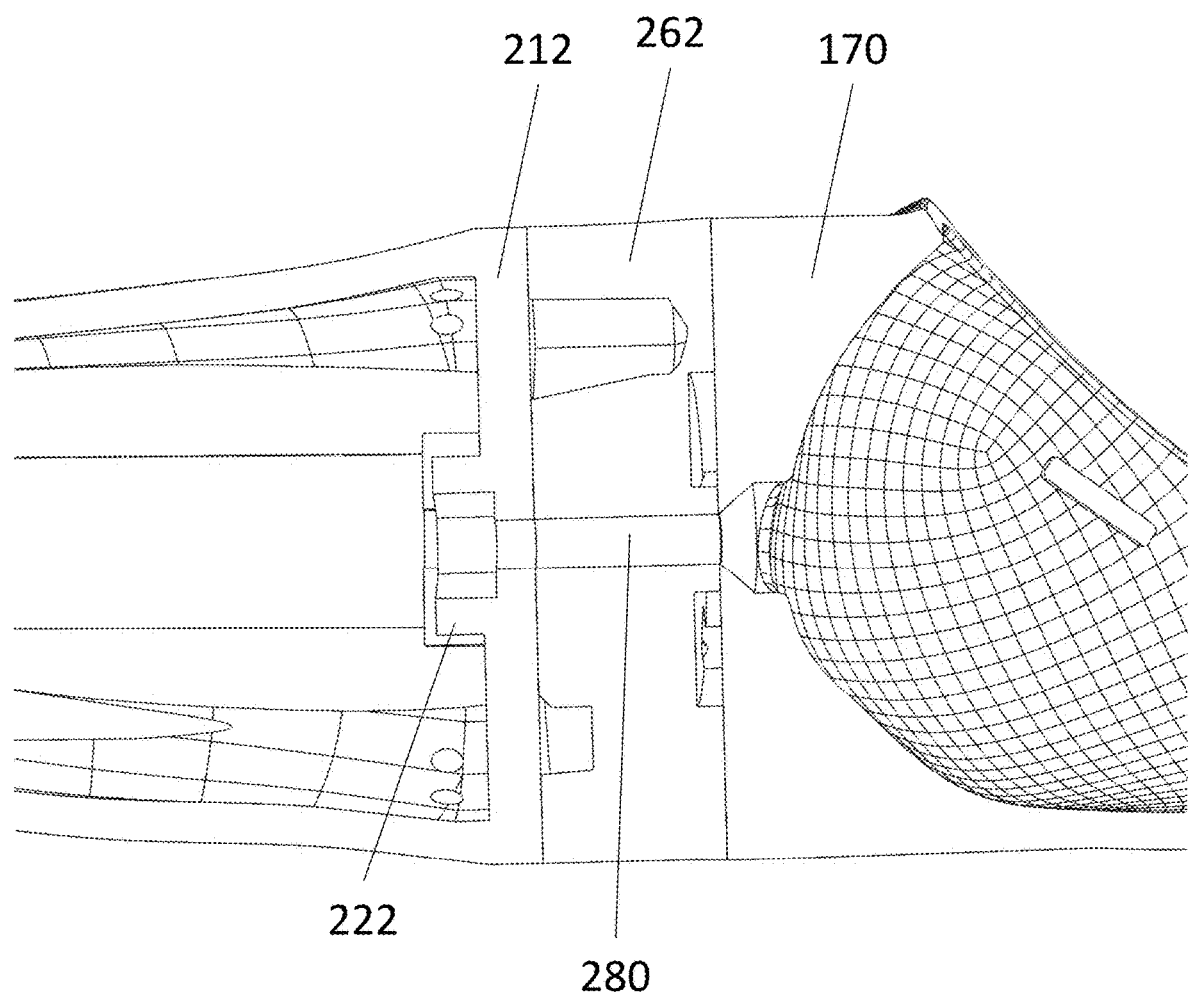
FIG. 9 is a cross-section showing the connection between the socket of FIGS. 2A-C and the prosthetic forearm of FIGS. 6A-E.

The coupling of distal socket 150, cover 260, and main forearm 210 is illustrated in FIG. 9. In the illustrated embodiment the components may be coupled by inserting a threaded bolt through the aperture 172 in the linking portion 170 of the distal socket 150, further through the aperture 268 in the base 262 of the cover 260, and finally through the aperture 216 in the base 212 of the main forearm 210. As described above, a threaded nut may be positioned within nut housing 222. The bolt 280 may be rotated to draw the nut and secure the distal socket 150 to the assembled prosthetic forearm 200. The bolt 280 may be tightened to secure the components together, while also allowing for manual rotation of the prosthetic forearm 200 with respect to the distal socket 150 as described above.

Figure 10A:
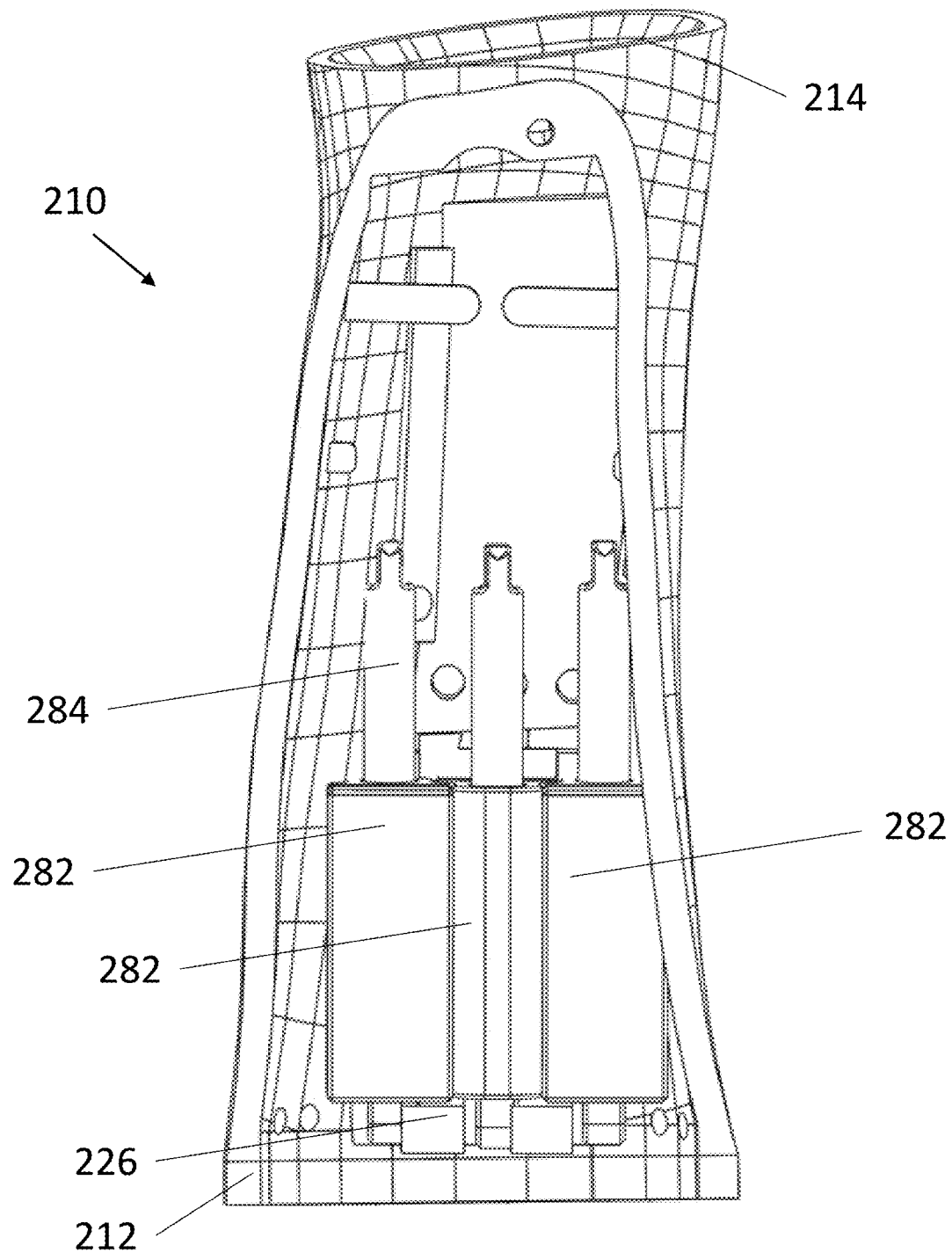
FIG. 10A is a view of the main forearm component of FIGS. 7A-E with actuator components positioned therein.
Figure 10B:
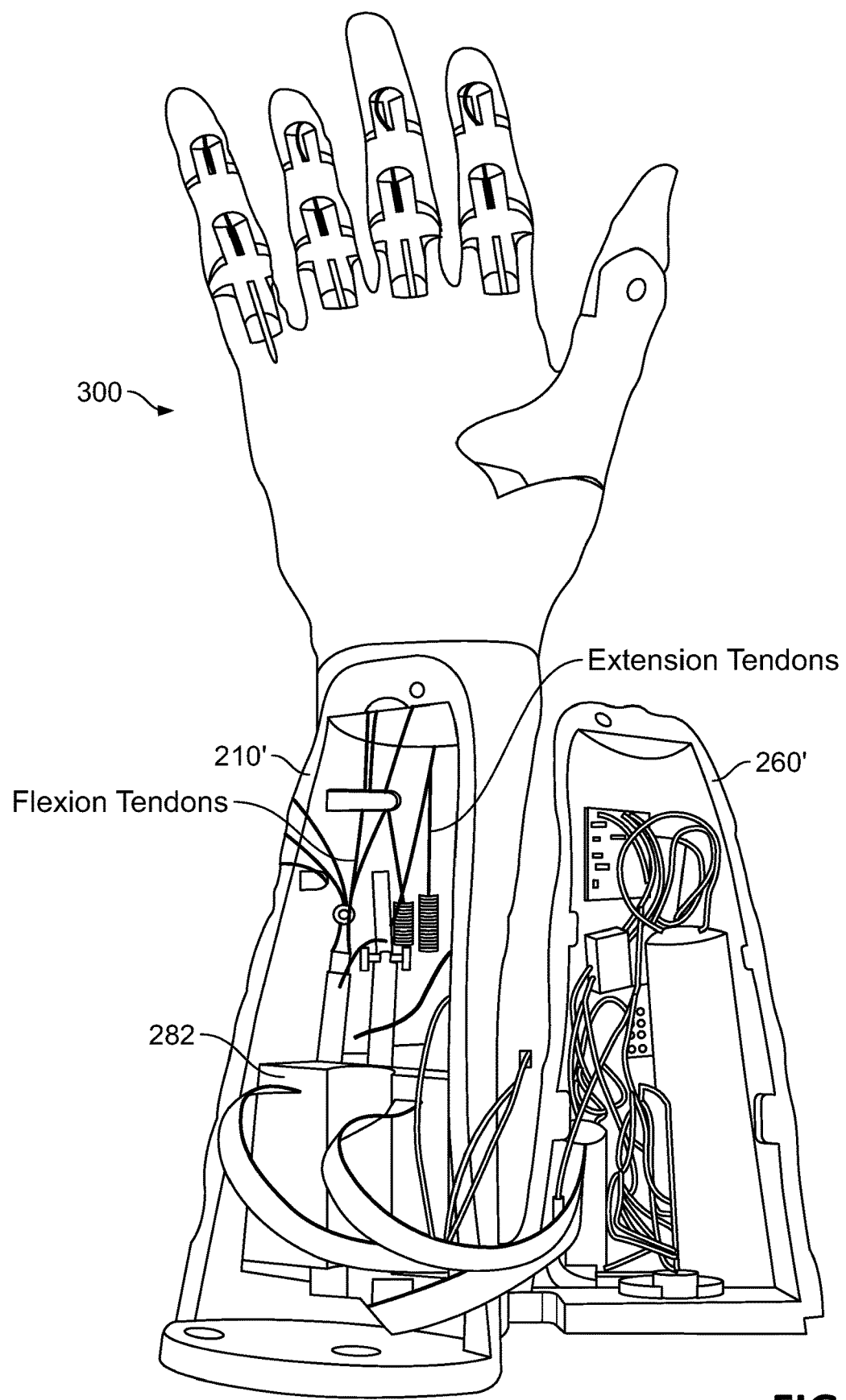
FIG. 10B is a picture of a prosthetic forearm similar to that shown in FIGS. 6A-E with mechanical and electronic components housed therein.

FIG. 10A illustrates main forearm 210 with three linear actuators 282 positioned therein secured to support member 226. Each linear actuator 282 may include a distal portion 284 attached to one or more prosthetic tendons. The distal portion 284 of each linear actuator 282 may be coupled to one or more prosthetic tendons, for example in the form of a cable such as high strength fishing line. In the illustrated embodiment, one linear actuator 282 is coupled to a prosthetic tendon routed to the prosthetic thumb, one linear actuator 282 is coupled to a prosthetic tendon routed to the prosthetic index finger, and one linear actuator 282 is coupled to three prosthetic tendons coupled to the prosthetic middle, ring, and pinky fingers. With this configuration, one linear actuator 282 causes flexion of the prosthetic thumb, one linear actuator 282 causes flexion of the prosthetic index finger, and the remaining linear actuator 282 causes flexion of the remaining three fingers substantially in unison. Thus, these prosthetic tendons may be referred to herein as flexion tendons. FIG. 10B is a picture of a main forearm 210' and cover 260' with mechanical and electronic components coupled thereto. Main forearm 210' and cover 260' are substantially identical to main forearm 210 and cover 260, with the exception that the bases of the two components are substantially reversed so that the base of the cover 260' is positioned distal to the base of the main forearm 210' in an assembled condition. As illustrated, main forearm 210' may include all or substantially all of the mechanical components for moving prosthetic hand 300, while cover 260' may include all or substantially all of the electronic components for moving prosthetic hand 300. These components are described in greater detail below after the remainder of the structure of prosthetic hand 300 is described.

In the illustrated embodiment, each linear actuator 282 includes a geared DC motor, spur gears, a lead screw, a slide potentiometer, and a shaft that is actuated. Such an actuator 282 may work by the DC motor driving a lead screw which pushes a rod that is anchored to a nut that is threaded onto the lead screw. The slide potentiometer may be attached to the enclosure and the push rod of the actuator 282 to be able to track the linear position of the rod. The rod may be the distal portion labeled as 284 in FIG. 10A. The stroke of the linear actuator 282 may vary, but typically the stroke may be around 20 mm, which may allow for precise control over the position of the actuator 282.

Although the function and routing of the prosthetic tendons is described in greater detail below, the connection of the prosthetic tendons within prosthetic forearm 200 is described here. There may be small mounting hole at that the end of the rod 284 of the linear actuator 282. The prosthetic flexion tendons may be attached to this portion of the linear actuator 282. The prosthetic flexion tendons can attach to the rod end in various suitable ways. For example, the end of the prosthetic flexion tendon may be tied directly to the mounting hole of the rod. In another example, a bracket may be provided so there is a hole that runs substantially parallel to the prosthetic flexion tendon path that allows for a hollow threaded rod to sit inside of this hole and is secured and adjusted by a nut sitting inside of the bracket. The prosthetic flexion tendon may be tied off on the hollow threaded rod so that the tension of the prosthetic flexion tendon can be adjusted by rotating the nut on the hollow threaded rod. In a further embodiment, the prosthetic flexion tendon may be run through the hole of the linear actuator rod and an additional part that clamps the tendon to itself may be provided. This may be accomplished by making a loop of the prosthetic flexion tendon, pulling it tight and adding a clamp that attaches to the loop ends so there are two parts of the tendon running through the clamp. The clamp may tightened by turning a fastener which compresses the prosthetic flexion tendon to a flat surface. All of the tendons, both flexion and extension, may be high-end fishing line. Either a monofilament or a braided fishing line may be used depending on the size of the prosthesis 10. Preferably, a line with a break strength between about 20 lbs and about 100 lbs is used, although it should be understood that other types of wires or cables having the same or other break strengths may be suitable. The prosthetic tendons preferably include coatings to minimize friction on surfaces such as the tunnels 311 through which they are routed.

As noted above and explained in greater detail below, similar or identical tendons may be coupled to springs within the forearm to serve as extension tendons to put the fingers 360$a$-$d$ and thumb 330 in extension in the absence of applied forces. The prosthetic extension tendons may be formed of any of the materials described above for the flexion tendons, and the extension tendons may be coupled to the springs in substantially the same ways as the flexion tendons are coupled to the actuators 282.

Figure 11A:
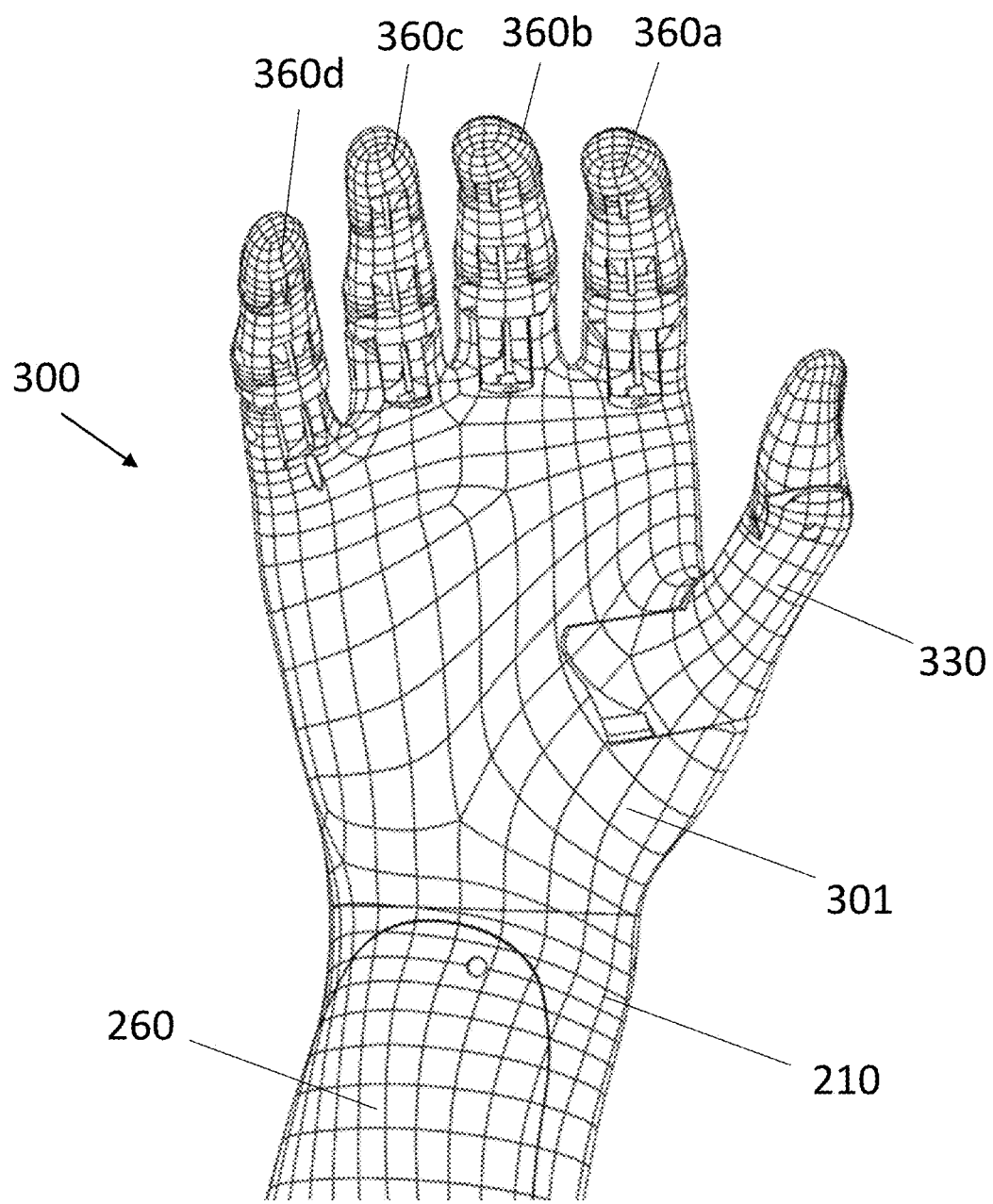
FIGS. 11A-C are views of a prosthetic hand of the prosthetic extremity of FIGS. 1A-C.
Figure 11B:
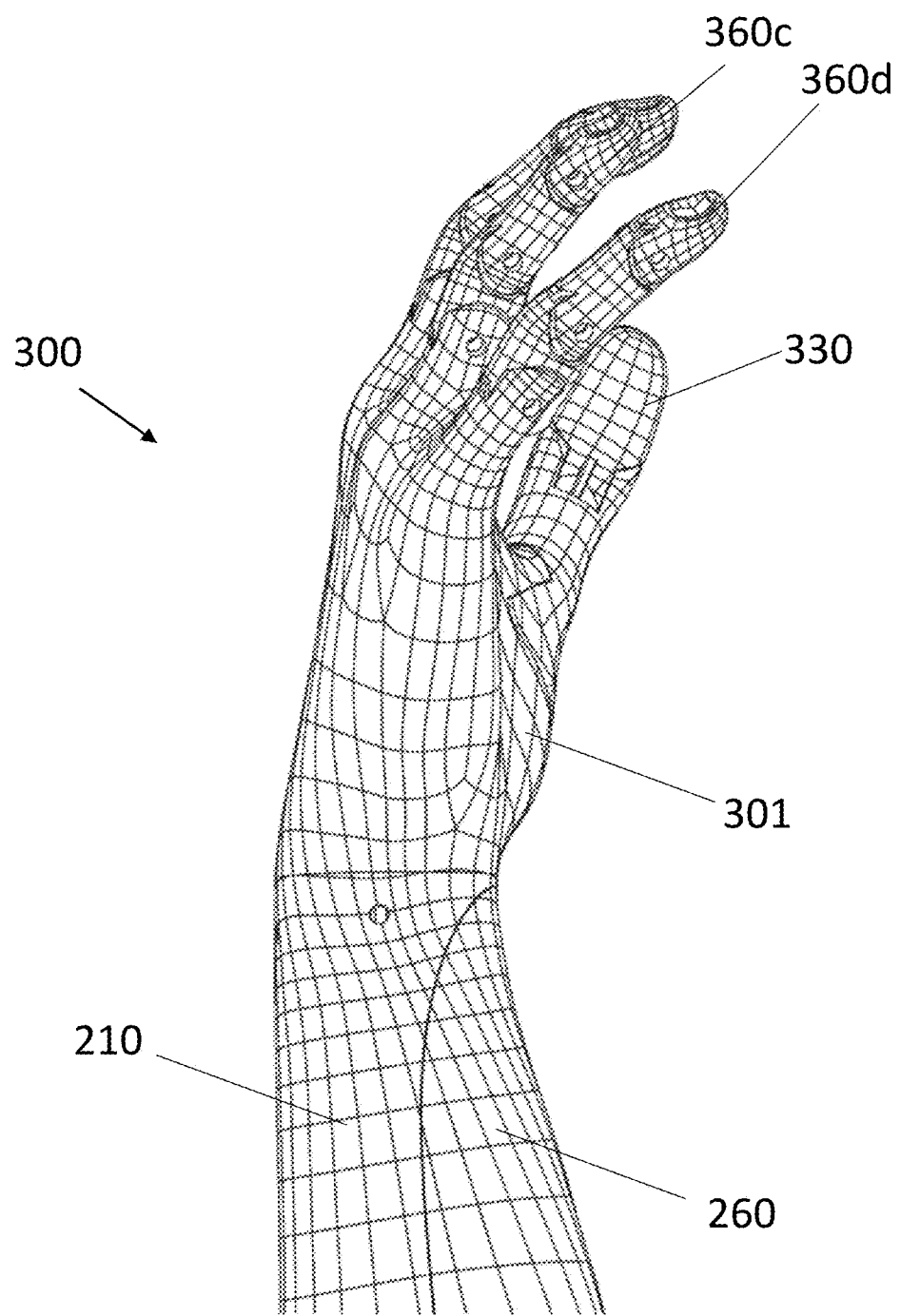
Figure 11C:
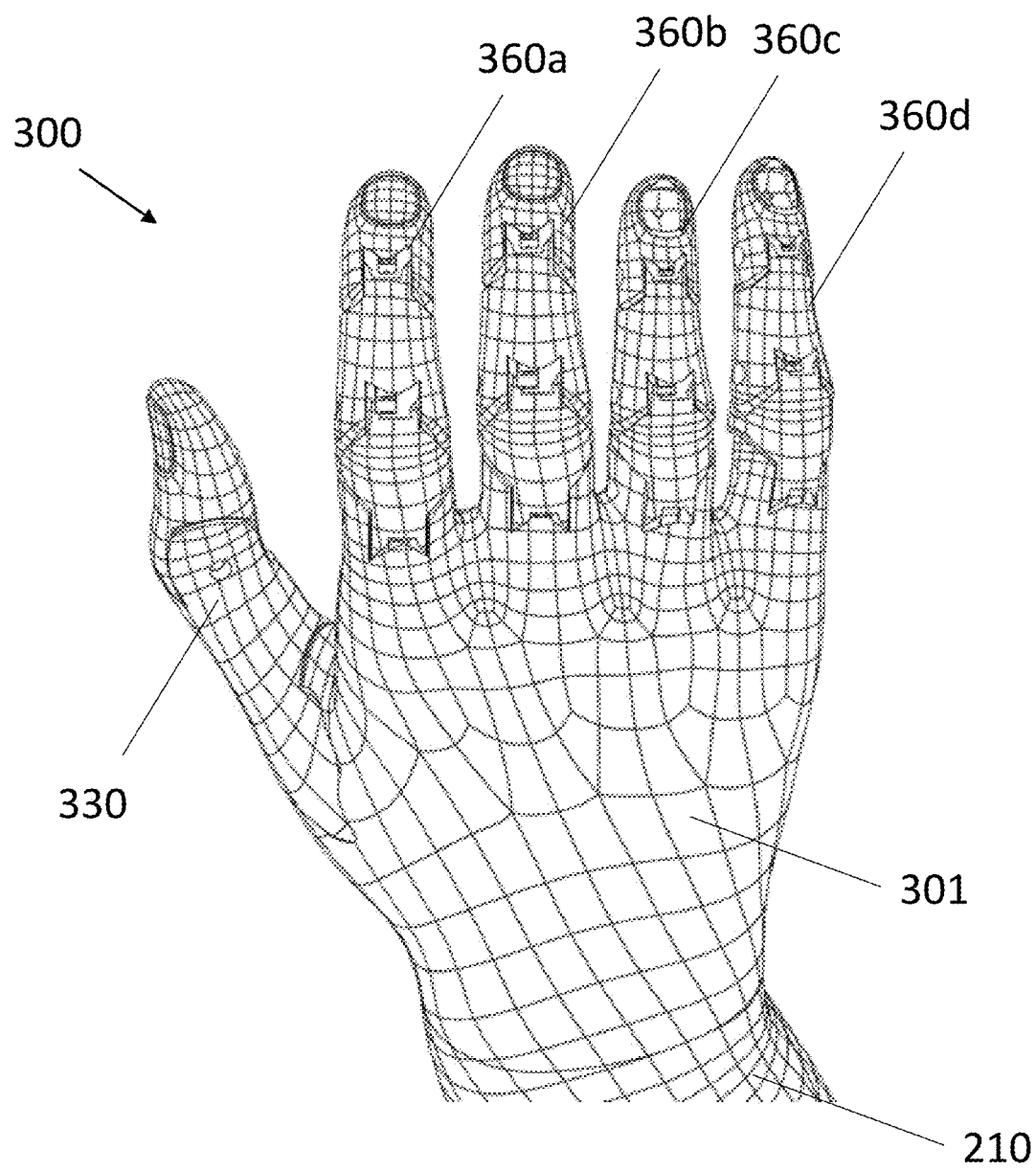
Figure 12A:
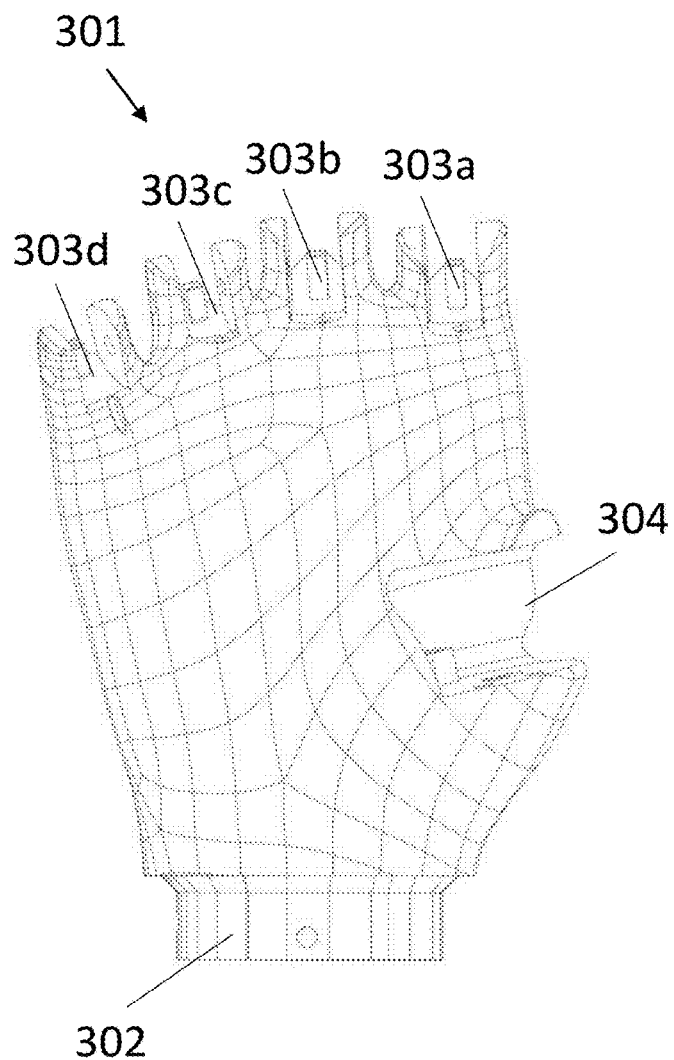
FIGS. 12A-D are views of a palm of the prosthetic hand of FIGS. 11A-C.
Figure 12B:
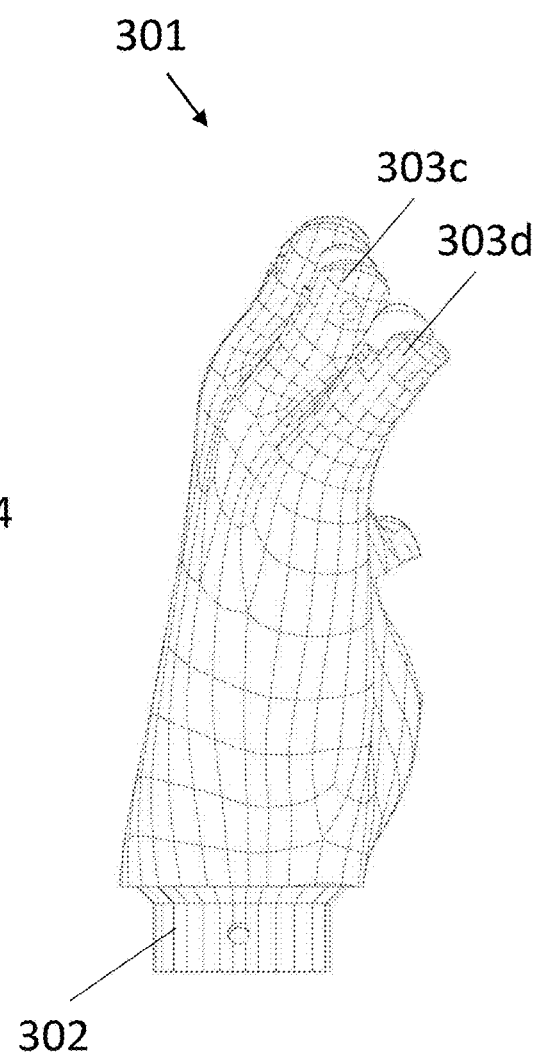
Figure 12C:
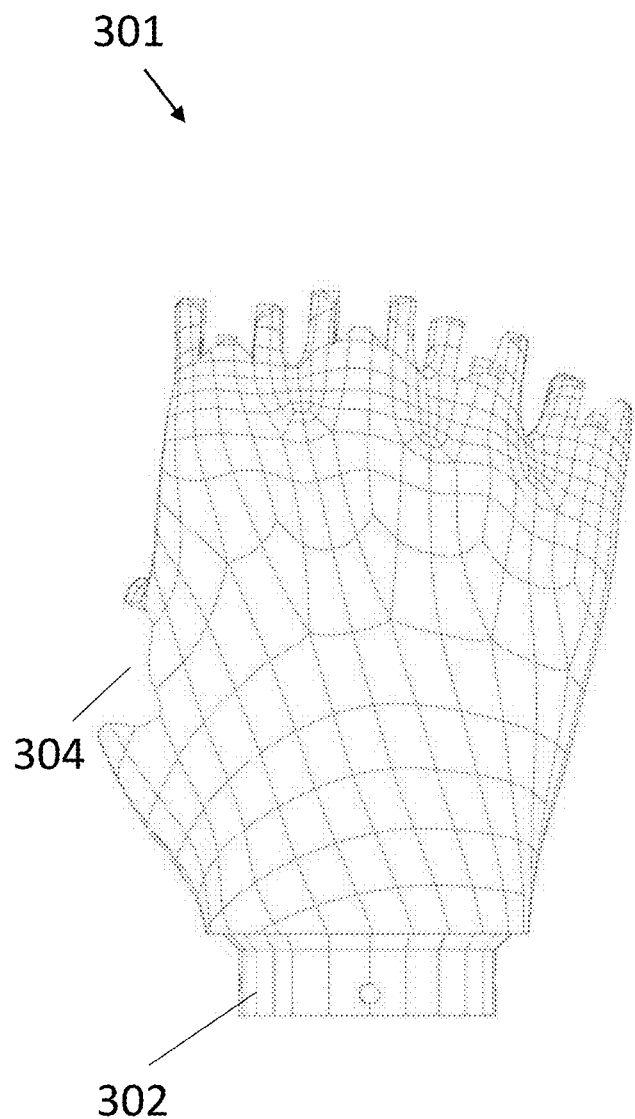
Figure 12D:
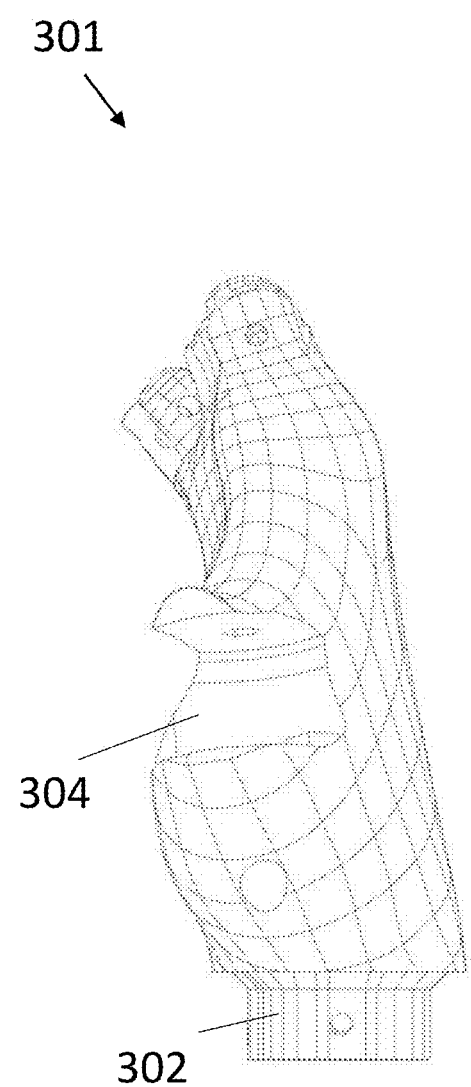

FIGS. 11A-C illustrate various views of prosthetic hand 300 coupled to main forearm 210 of prosthetic forearm 200. Generally, prosthetic hand may include a palm 301, thumb 330, and four fingers 360*a-d*, including an index finger 360*a*, middle finger 360*b*, ring finger 360*c*, and pinky finger 360*d*. As should be clear from the description below, fingers 360*a-d* may be substantially identical to one another in structure, and thus only the structure of a single finger 360 is described in detail below. However, the various fingers 360*a-d* and/or components thereof may be slightly differently sized or contoured in order to more closely mimic either an average hand or a remaining hand of a user. Similarly, the palm 301 (described in greater detail below), wrist 214, and prosthetic forearm 200, as well as components of each, may have different sizes and/or contours than are shown in the drawings and different sizes and/or contours relative to each other or relative to other components of the system than are shown in the drawings in order to provide a desired size and contour for a particular user.

FIGS. 12A-D illustrate various views of palm 301 disassembled from thumb 330 and fingers 360*a-d*. It should be understood that, as used herein, the term "palm" generally refers to the portion of the hand between the wrist and fingers, including both the front surface that may be frequently called a palm, and the back of the hand as well. Generally, palm 301 may include a proximal coupling portion 302 for coupling palm 301 to the main forearm 210 of prosthetic forearm 200, although in some embodiments palm 301 may be formed integrally with main forearm 210. Palm 301 may also include four finger couplings 303*a-d* and a thumb coupling 304 to facilitate attachment of the fingers 360*a-d* and the thumb 330 to the palm 301.

Figure 13A:
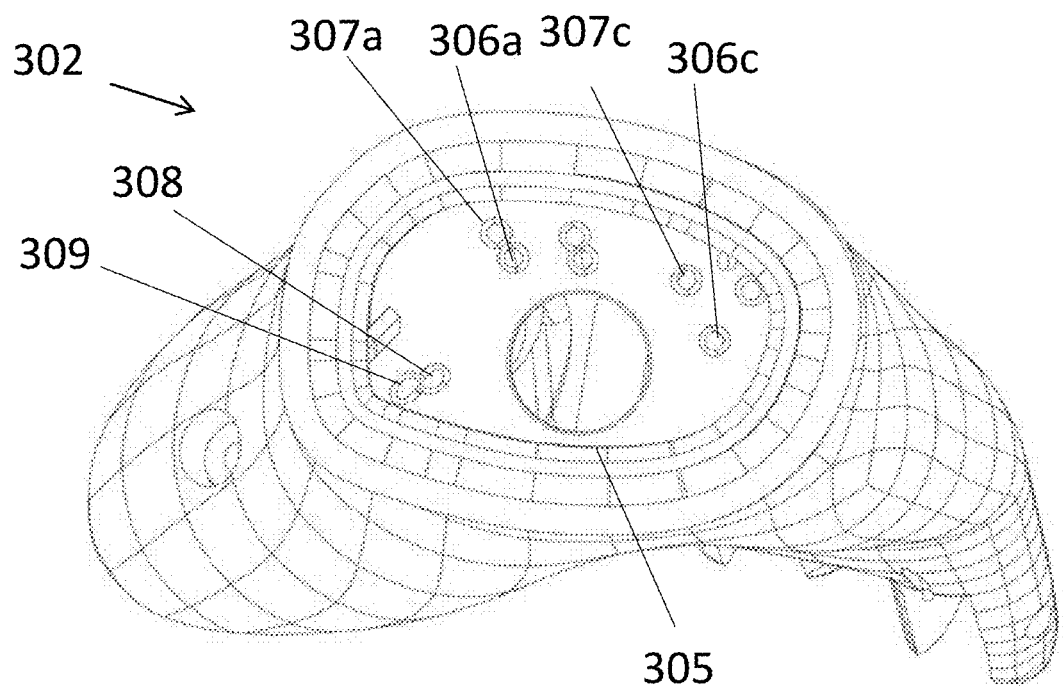
FIGS. 13A-B are views of a proximal coupling portion of the palm of FIGS. 12A-D.
Figure 13B:
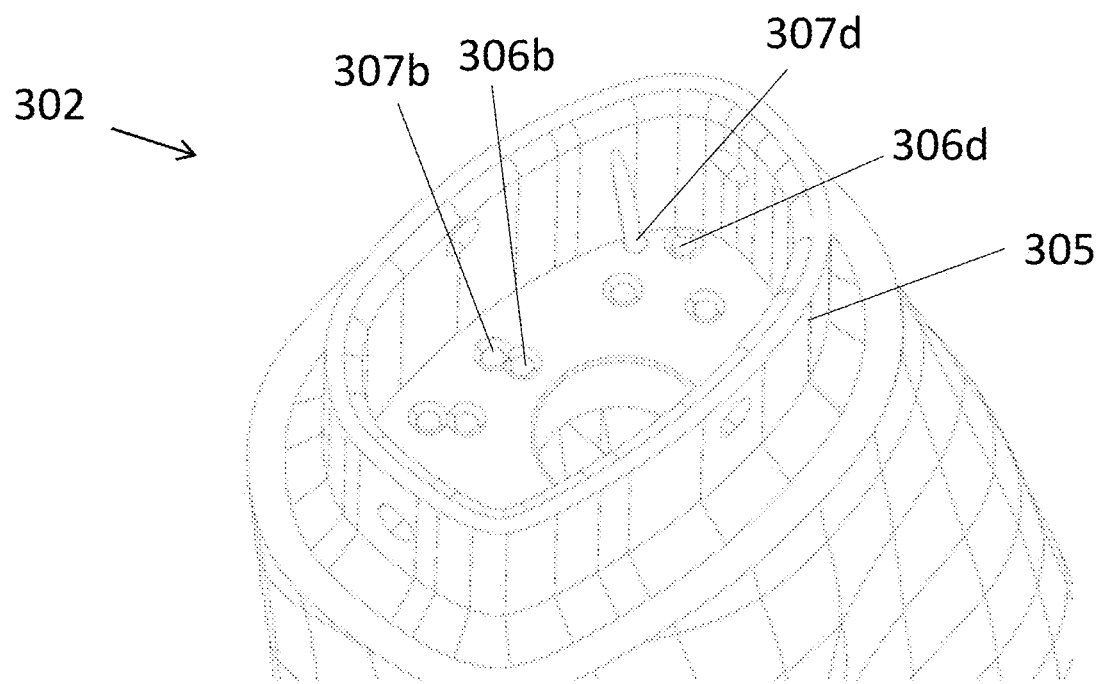

FIGS. 13A-B illustrate aspects of the proximal coupling portion 302 of palm 301. Proximal coupling portion 302 may include a lip 305 extending to the proximal end of palm 301. Lip 305 may be sized and shaped to fit within distal wrist 214 of main forearm 210 in only one or substantially only one configuration, and may include apertures or other coupling features that align or correspond to apertures or coupling features in distal wrist 214. For example, in the illustrated embodiment distal writs 214 and lip 305 include corresponding apertures that are aligned when palm 301 is assembled to forearm component 210. Pins may be inserted through the aligned apertures to secure the palm 301 relative to the main forearm 210. Preferably, the shape of lip 305 and the interior surface of distal wrist 214 are such that, upon assembly, the palm 301 is capable of no or substantially no rotation or other movement. However, as described in greater detail below, in other embodiments the palm 301 may be coupled to main forearm 210 via a joint or other mechanism that allows for movement of the palm 301 relative to the assembled forearm 200. Further, when palm 301 is coupled to assembled forearm 200, the transition between outer surfaces of the assembled forearm 200 and the palm 301 are preferably substantially smooth and continuous.

Still referring to FIGS. 13A-B, proximal coupling portion 302 may include a plurality of apertures to allow for prosthetic tendons, described in greater detail below, to pass from main forearm 210 to the thumb 330 and fingers 360*a-d* via palm 301. In the illustrated embodiment, proximal coupling portion 302 includes a pair of apertures for each finger 360*a-d* and a pair of apertures for thumb 330, such that one prosthetic tendon controlling flexion and one prosthetic tendon controlling extension may pass into palm 301 for each finger 360*a-d* and thumb 330. In the illustrated embodiment, apertures 306*a-d* correspond to the apertures through which a prosthetic tendon for flexion will pass into fingers 360*a-d*, respectively, while apertures 307*a-d* correspond to the apertures through which a prosthetic tendon for extension will pass into fingers 360*a-d*, respectively. Similarly, as illustrated, aperture 308 is configured to receive a prosthetic tendon for flexion of thumb 330, while aperture 309 is configured to receive a prosthetic tendon for extension of thumb 330. However, it should be understood that the particular positioning of the apertures need not be identical to the positions illustrated. A central hole in may be provided in proximal coupling portion 302, as best seen in FIG. 13A, for manufacturability purposes, for example so the palm 301 can be 3D printed with a hollow interior.

Figure 14A:
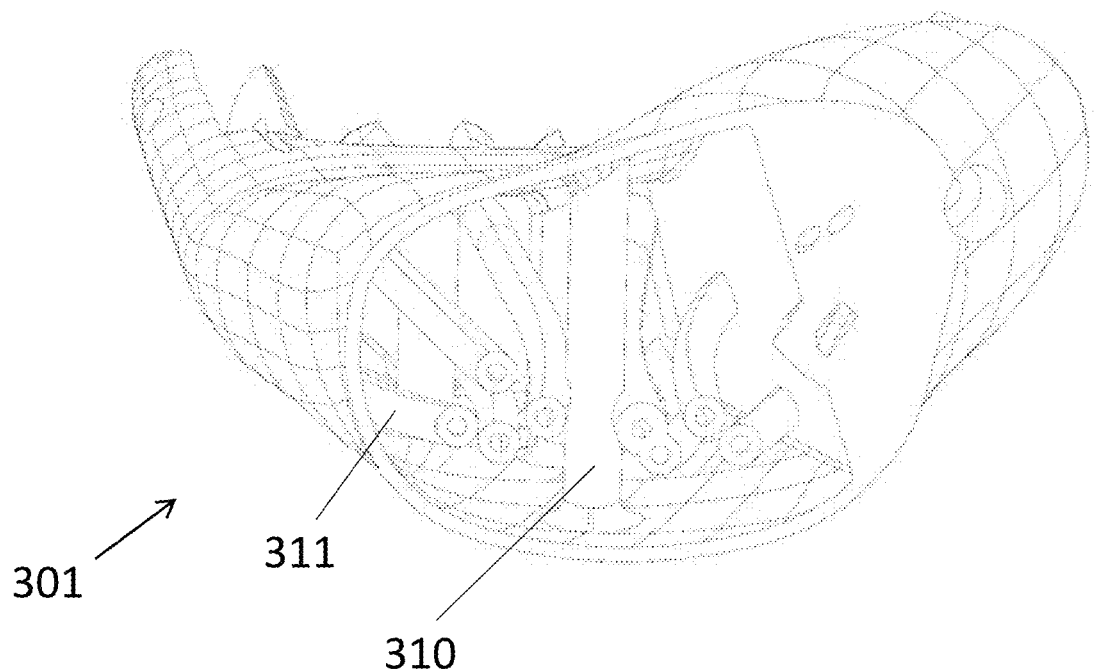
FIGS. 14A-F are various cross-sections of the palm of FIGS. 12A-D to illustrate internal components.
Figure 14B:
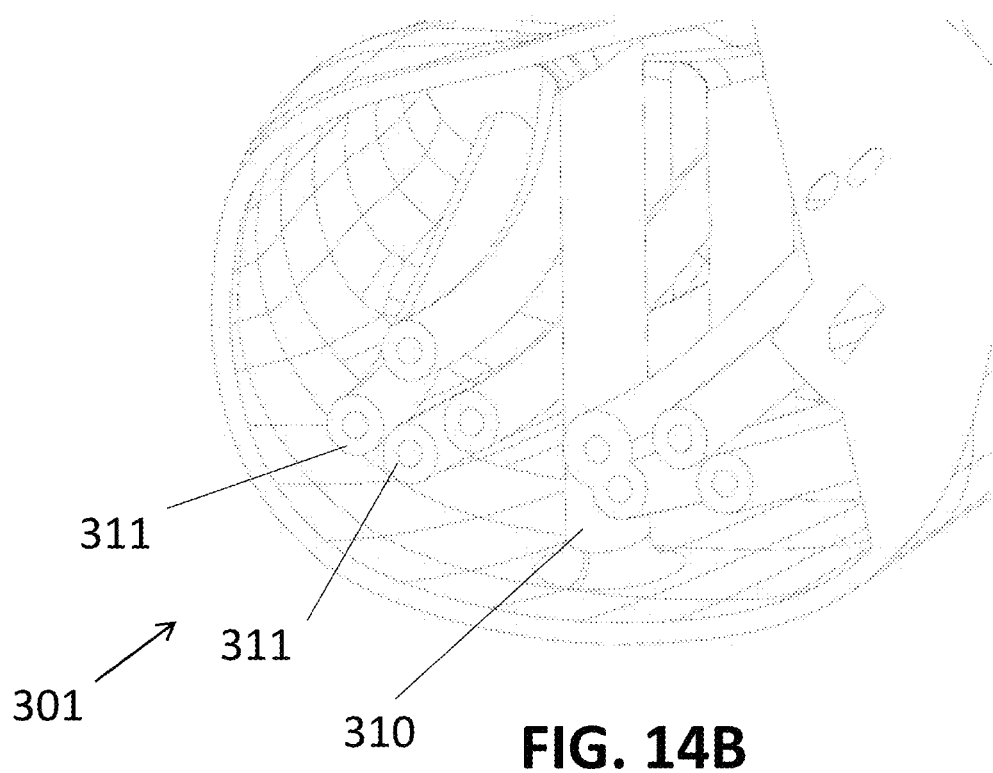
Figure 14C:
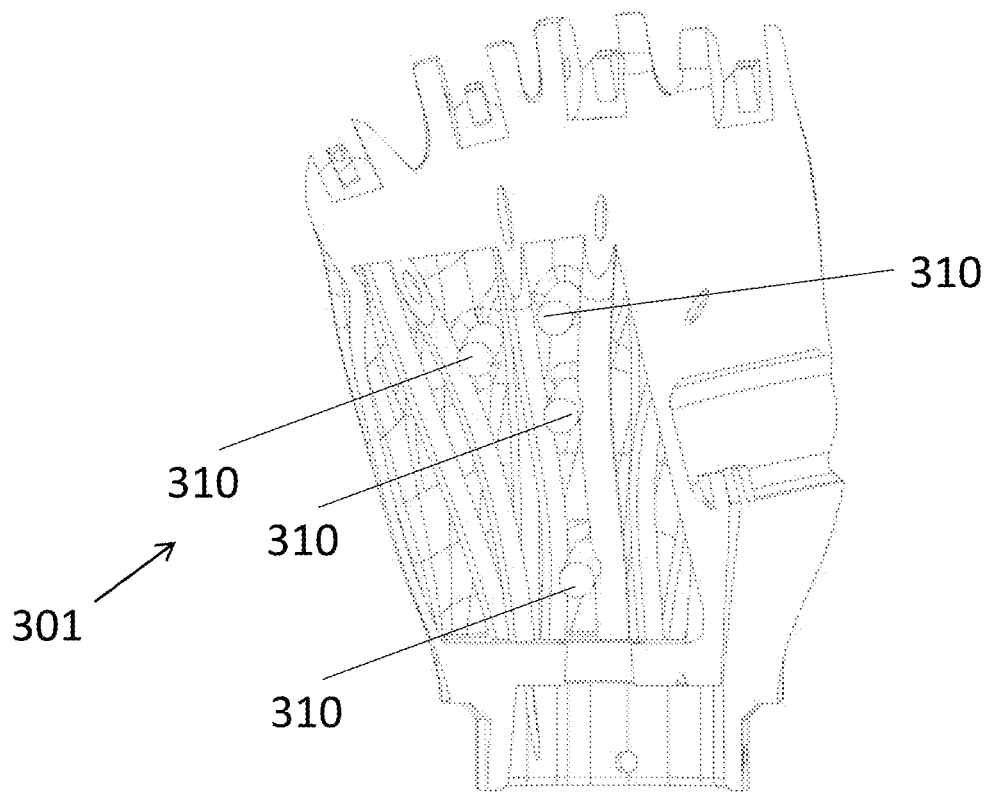
Figure 14D:
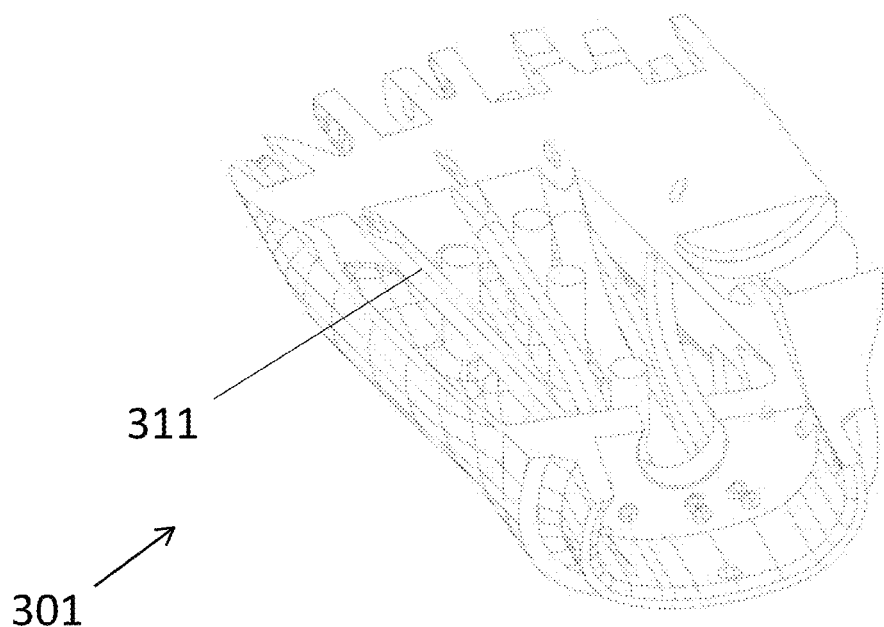
Figure 14E:
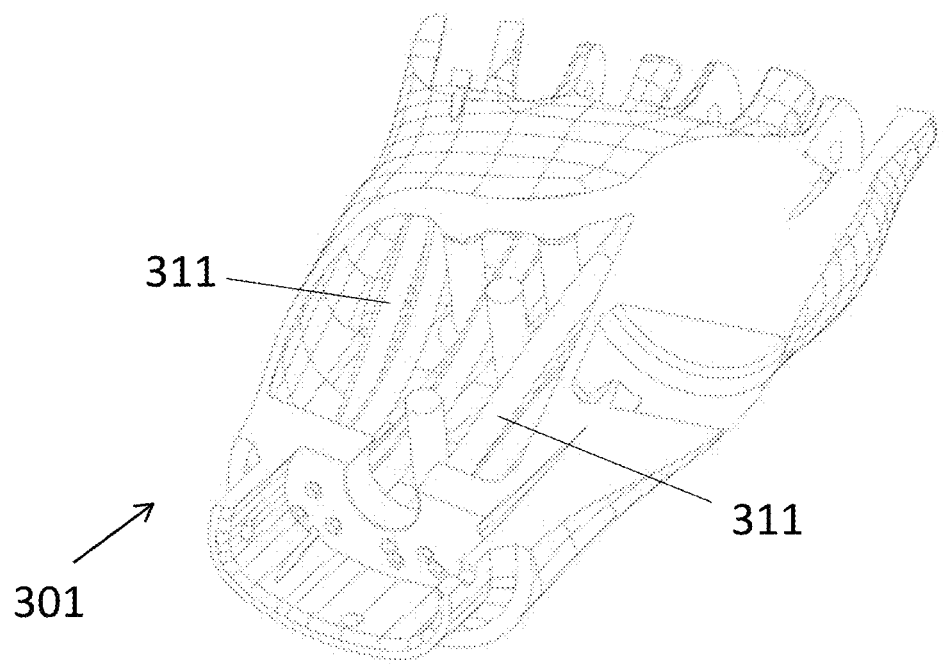
Figure 14F:
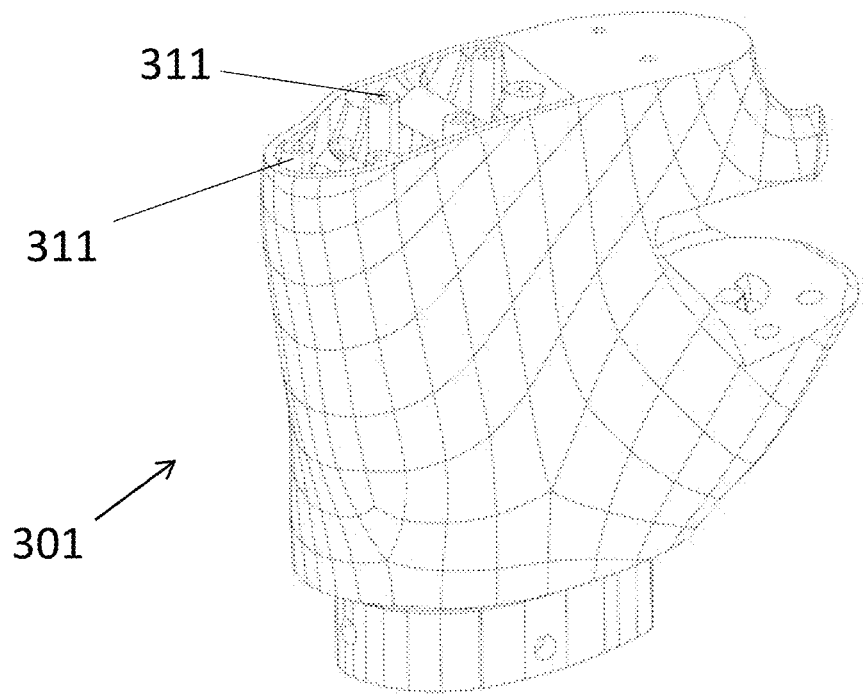

FIGS. 14A-F show various cross-sections of palm 301 to illustrate internal components of palm 301. It should be noted that most of palm 301 is hollow in order to reduce the amount of material required to form palm 301. However, at least because palm 301 is expected to experience various applied forces, particularly when prosthetic hand 300 is in the process of gripping an object by applying force to that object, a variety of support posts 310 are provided within palm 301. For example, as shown in FIGS. 14A-C, a first support post 310 may extend from a front surface to a rear surface of palm 301 near proximal coupling 302. A second support post 310 may extend from the front to the rear of palm 301 near a center of palm 301. A third support post 310 may extend from the front to the rear of palm 301 proximal to the space between the middle finger 360*b* and ring finger 360*c*. A fourth support post 310 may extend from the front to the rear of palm 301 proximal to the space between the ring finger 360*c* and the pinky finger 360*d*. It should be understood that the position and number of posts 310 may be varied in order to provide support to any hollow areas of palm 301 expected to experience forces that could otherwise compromise the structural integrity of palm 301, particularly when prosthetic hand 300 is gripping or applying force to an object. Further, as best shown in FIGS. 14C-D, the knuckle areas may be made solid since a large amount of mechanical stress is expected in those positions when the fingers 360*a-d* and thumb 330 come in contact with an object. Other mechanisms for supporting likely stresses while minimizing material use, such as using internal lattice patterns, may also be utilized.

Still referring to FIGS. 14A-F, a plurality of tendon tunnels 311 may be positioned interior to palm 301 in order to help guide prosthetic tendons from the apertures 306*a-d*, 307*a-d*, 308, 309 in proximal coupling portion 302 to the corresponding aperture in finger coupling 303*a-d* or thumb coupling 304. Although the tunnels 311 may not be required, the tunnels 311 may assist in helping ensure that the tendons do not entangle one another and do not experience significant damage, for example by ensuring that as the tendons move, they remain in contact with a substantially smooth inner surface of the tunnels 311 without experience sharp turns. Although every tunnel 311 is not separately labeled in FIGS. 14A-F, it should be understood that, as illustrated, ten tunnels 311 are provided, each tunnel 311 having an inlet defining one of the apertures 306*a-d*, 307*a-d*, 308, or 309. Each tunnel 311 also has a corresponding outlet in a finger coupling 303*a-d* or thumb coupling 304, at which point the prosthetic tendons extend to the front of a fingertip 390 or thumb tip for providing flexion, or to a rear of a fingertip 390 or thumb tip for providing extension. The apertures at the tunnel 311 outlets are described in greater detail below.

Figure 15:
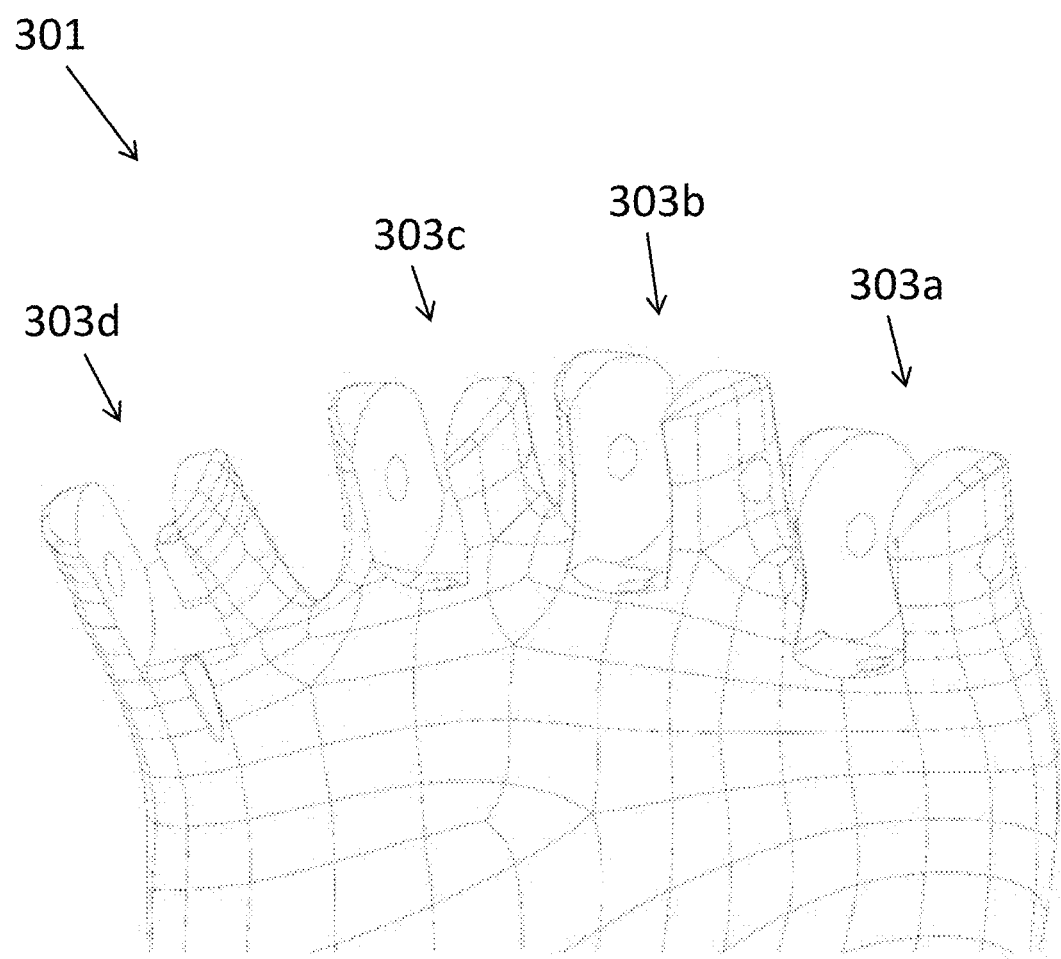
FIG. 15 is an enlarged view of a distal end of the palm of FIGS. 12A-D.
Figure 16A:
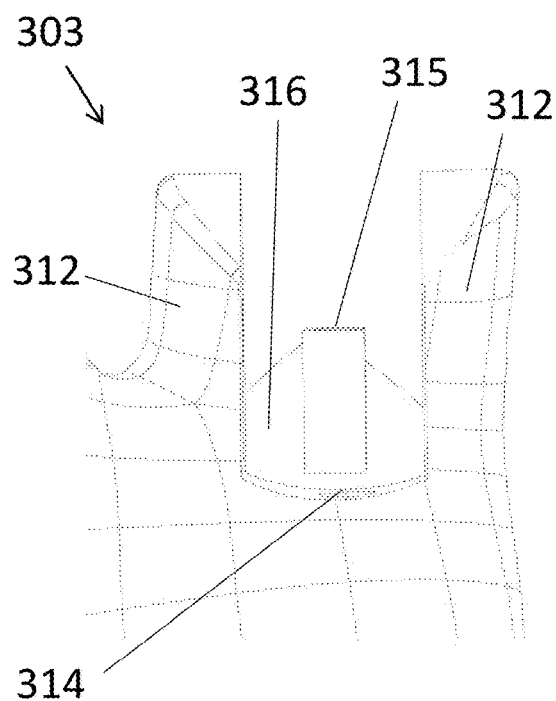
FIGS. 16A-C are enlarged views of a representative finger coupling of the palm of FIGS. 12A-D.
Figure 16B:
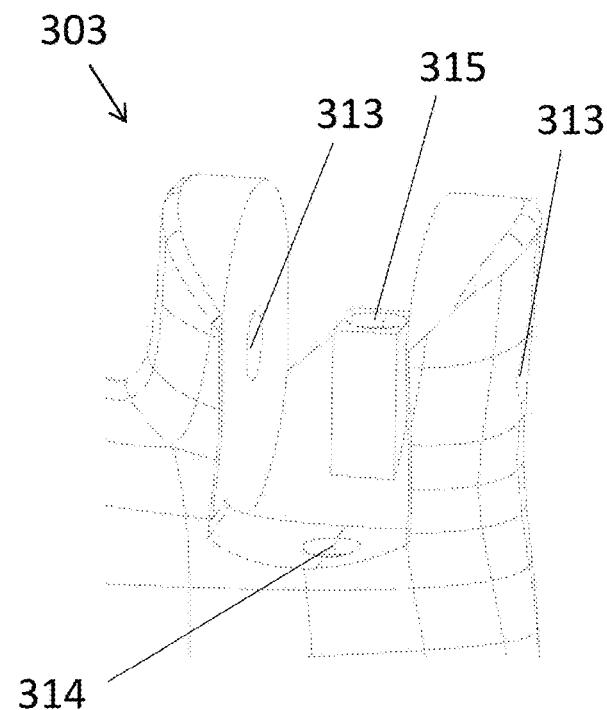
Figure 16C:
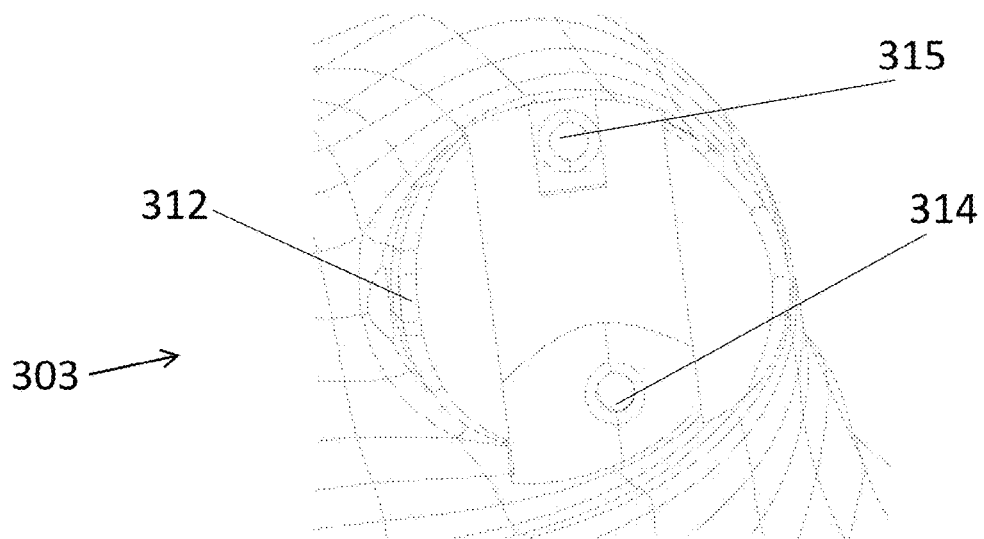
Figure 17A:
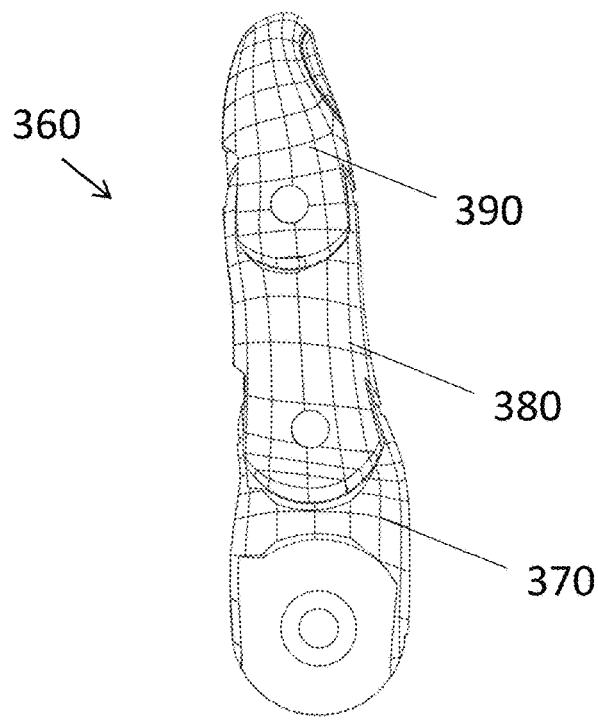
FIGS. 17A-D are views of a representative finger of the prosthetic hand of FIGS. 11A-C.
Figure 17B:
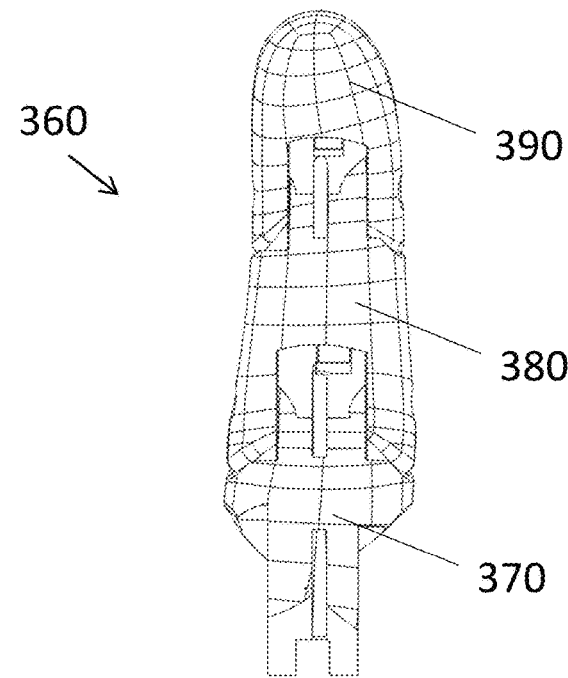
Figure 17C:
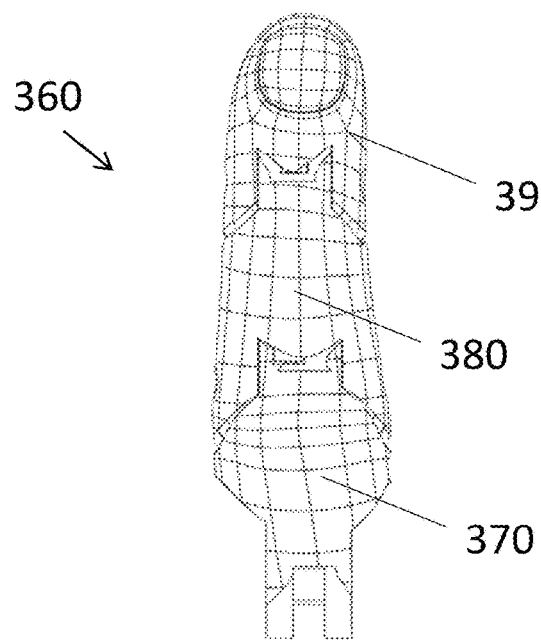
Figure 17D:
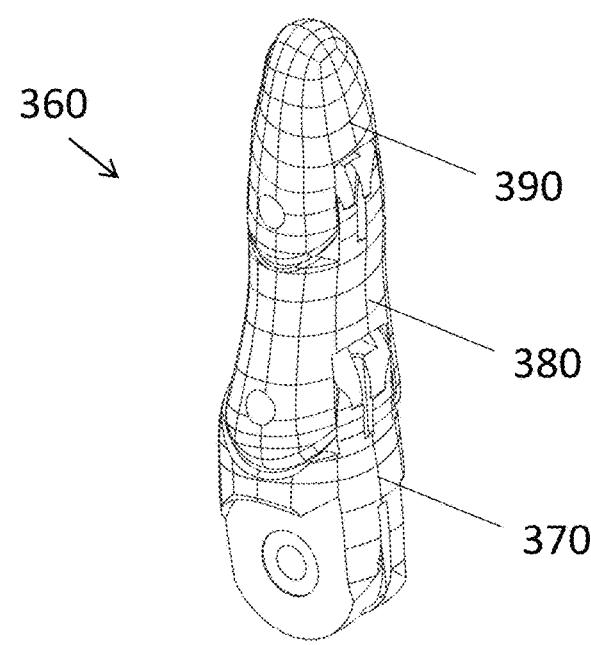

FIG. 15 illustrates a distal end of palm 301 to better show the finger couplings 303*a-d*. Each finger coupling 303*a-d* functions to couple a corresponding prosthetic finger 360*a-d* to the palm 301. FIGS. 16A-C illustrate enlarged views of a representative finger coupling 303. It should be understood that finger couplings 303*a-d* may be substantially identical to one another, although sizes and shapes may vary slightly in order to better mimic the user's remaining hand. However, because of the similarity of the structure of each finger coupling 303a-d, representative finger coupling 303 of FIGS. 16A-C is described and that description generally applies to each of the individual finger couplings 303a-d.

Referring now to FIGS. 16A-C, finger coupling 303 may include two lateral extensions 312. Each lateral extension 312 may include an aperture 313 therein, as best shown in FIG. 16B. The two lateral extensions 312 may function to receive a finger base 370 therebetween, with a pin or other fastener extending through the apertures 313 and corresponding apertures 371 in the finger base 370 so that the finger base 370 is capable or substantially freely rotating about an axis passing through apertures 313. In addition, each finger coupling 303 may include a flexion tendon aperture 314 and an extension tendon aperture 315. Flexion tendon aperture 314 may be the outlet of a corresponding flexion tendon tunnel 311, while extension tendon aperture 315 may be the outlet of a corresponding extension tendon tunnel 311. In the illustrated embodiment, the lateral extensions 312 form a general "U"-shape with the distal portion of palm 310. As described below, fingers 360a-d may include a finger base 370 that has a complementary shape for insertion between the lateral extensions 312. Further, in the illustrated embodiment, extension tendon aperture 315 is provided within a rear generally "V"-shaped or generally "U"-shaped extension portion that extends farther distally than a front portion of finger coupling 303.

A representative prosthetic finger 360 is illustrated in FIGS. 17A-D. As noted above, each prosthetic finger 360a-d may be substantially identical in structure, although the shape and size of each finger 360a-d may vary slightly to better mimic the user's remaining hand or otherwise an average natural hand. As such, a single representative finger 360 is described and it should be understood that the description generally applies to each prosthetic finger 360a-d. Generally, prosthetic finger 360 may include a base portion 370, a middle portion 380, and a tip portion 390. The individual portions of representative prosthetic finger 360 are described in detail below.

Figure 18A:
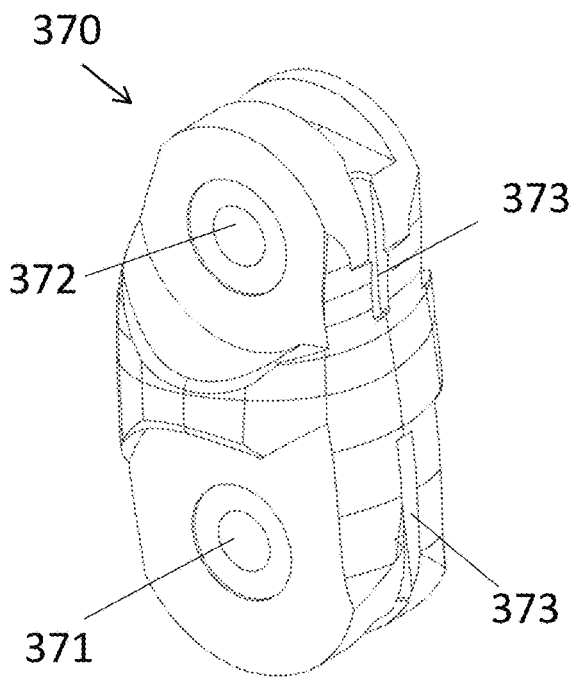
FIGS. 18A-F are views of a base of the finger of FIGS. 17A-D.
Figure 18B:
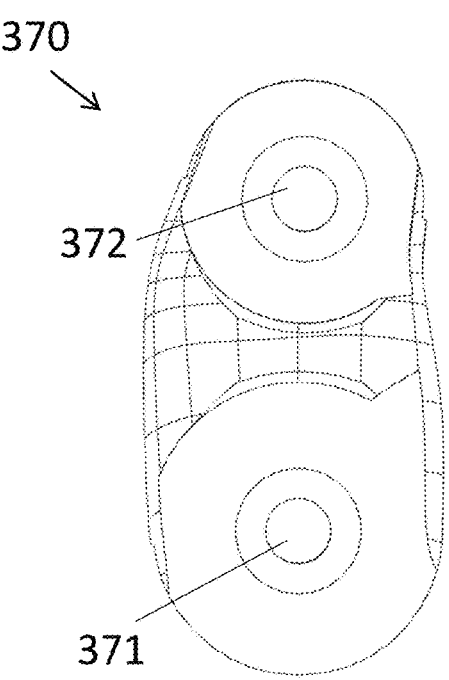

FIGS. 18A-F illustrate various views of finger base 370. Finger base 370 may include a rounded proximal portion with an aperture 371 extending therethrough. As best shown in FIG. 18B, the proximal portion may be substantially "U"-shaped. When coupled to finger coupling 303, a pin or other fastener may pass through both aperture 371 and apertures 313 so that finger base 370 is rotatable about aperture 371. This proximal portion of finger base 370 and finger coupling 303 may substantially mimic the function of the metacarpophalangeal joint. Finger base 370 may similarly include a distal portion with an aperture 372 extending therethrough, the distal portion shaped and configured to jointedly couple to middle portion 380, described in greater detail below.

Figure 18C:
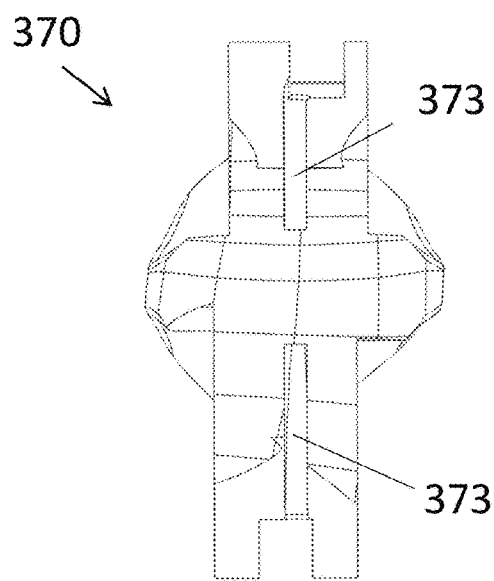
Figure 18D:
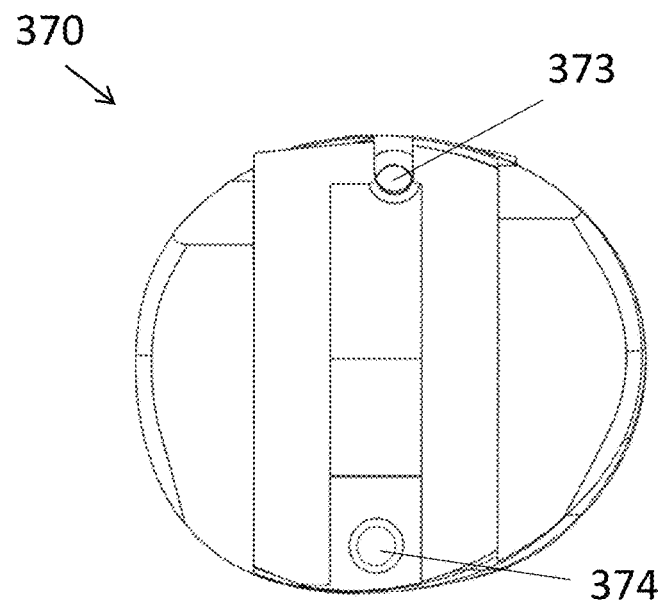
Figure 18E:
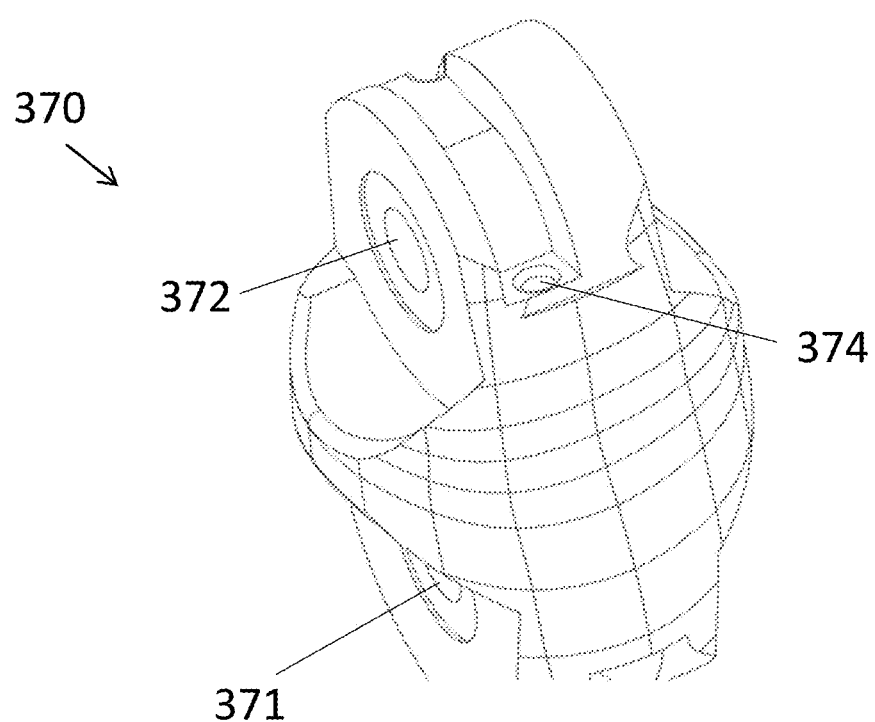
Figure 18F:
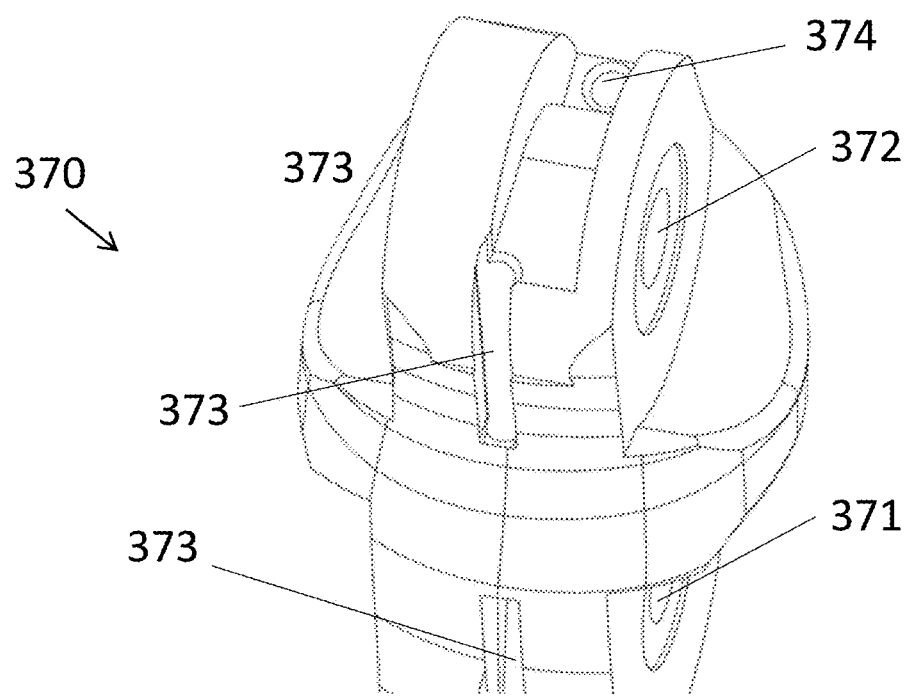

Referring now to the bottom view of finger base 370 of FIG. 18D, an anterior tunnel 373 and posterior tunnel 374 may be provided. When finger base 370 is coupled to finger coupling 303, anterior tunnel 373 may substantially align with flexion tendon aperture 314 and posterior tunnel 374 may substantially align with extension tendon aperture 315. The prosthetic flexion tendon exiting flexion tendon aperture 314 may pass through anterior tunnel 373. As best shown in FIGS. 18A, 18C, and 18E, anterior tunnel 373 may be open at the anterior-most portion, with a middle portion of the anterior tunnel 373 being fully closed between the proximal and distal portions of finger base 370. In this context, "anterior" refers to the front face of the palm, while the "posterior" direction refers to the back face of the hand. As sill become clear by the additional descriptions below, as the prosthetic flexion tendon passing into finger 360 is flexed, the finger base 370 begins to flex with respect to the finger coupling 303. The open anterior portions of anterior tunnel 373 helps to facilitate rotation of the joints in the finger 360 in a desired fashion without binding or otherwise damaging the prosthetic flexion tendon of the finger 360. This may be particularly true if the prosthetic flexion tendon has a substantially fixed length and is rigidly coupled at its first end to the fingertip 390 and at its other end to a linear actuator 282. Posterior tunnel 374, on the other hand, may be fully enclosed, as best shown in FIGS. 18E-F. A prosthetic extension finger tendon passing through extension tendon aperture 315 in finger coupling 303 may pass through posterior tunnel 374 and toward a rear of fingertip 390. As described in greater detail below, one end of prosthetic extension finger tendon may be coupled to a spring fixed within main forearm 210, with the other end fixedly coupled to a rear portion of fingertip 390, so that in the absence of other applied forces, finger base 370 tends to be in the extended condition as opposed to the flexed condition.

FIGS. 19A-E illustrate various views of the middle portion 380 of finger 360. Middle portion 380 may include a proximal portion with two lateral extensions 381, and each lateral extension 381 may include an aperture 382 extending therethrough. Lateral extensions 381 may be sized and shaped to fit over the distal portion of finger base 370 so that apertures 372 align with apertures 382. A pin or other fastener may pass through apertures 382 and 372 to hingedly couple middle portion 380 to finger base 370. Lateral extensions 381 may be substantially rounded at their proximal ends to fit within or adjacent correspondingly rounded portions of the middle section of finger base 370. The coupling between the proximal portion of middle portion 380 and the distal portion of finger base 370 may substantially mimic the function of the proximal interphalangeal joint. Middle portion 380 may similarly include a distal portion with an aperture 383 extending therethrough, the distal portion shaped and configured to jointedly couple to fingertip 390, described in greater detail below.

Figure 19A:
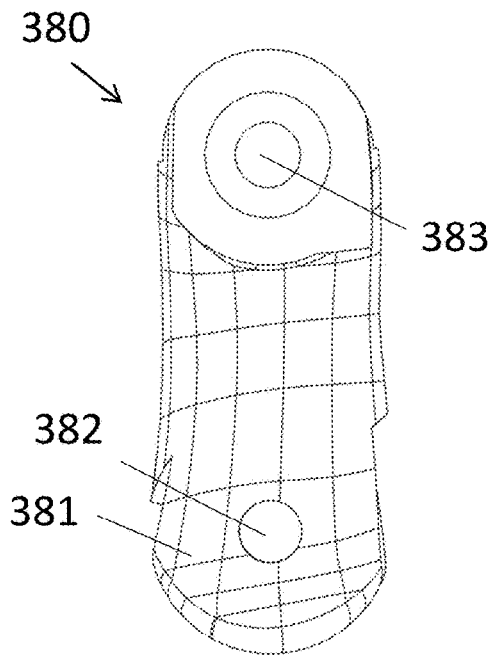
FIGS. 19A-E are views of a middle portion of the finger of FIGS. 17A-D.
Figure 19B:
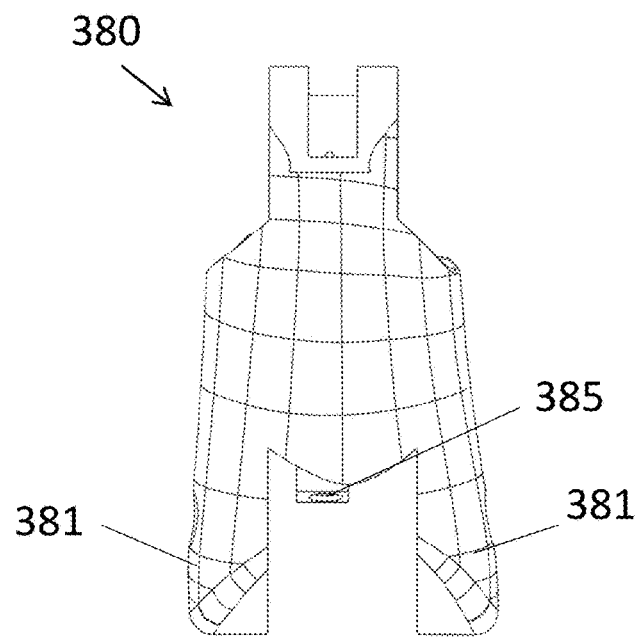
Figure 19C:
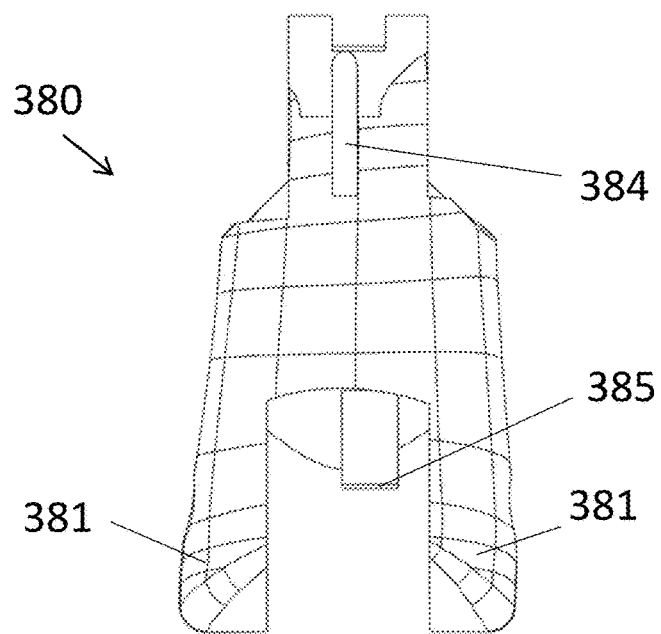
Figure 19D:
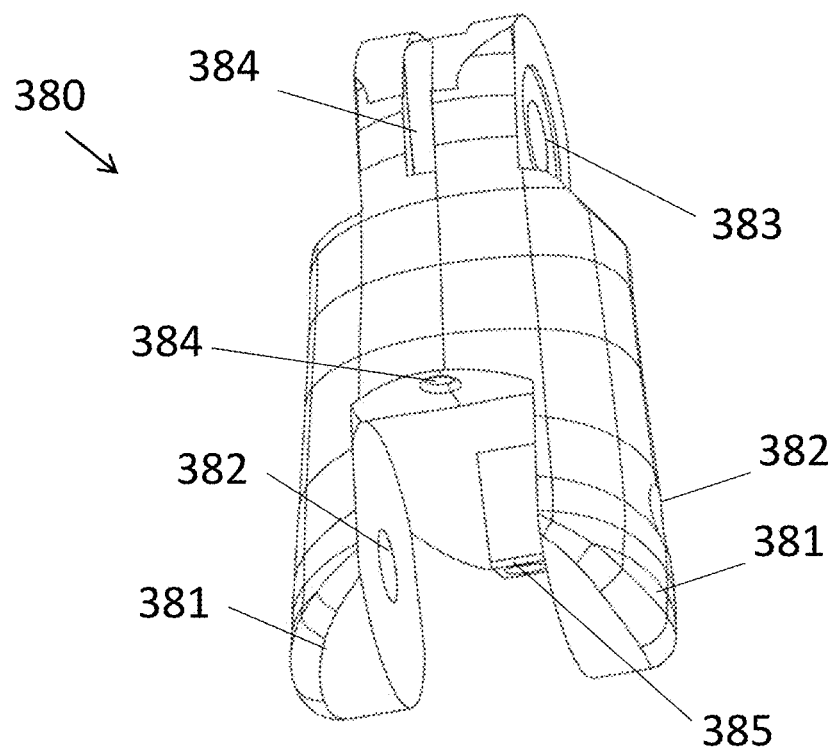
Figure 19E:
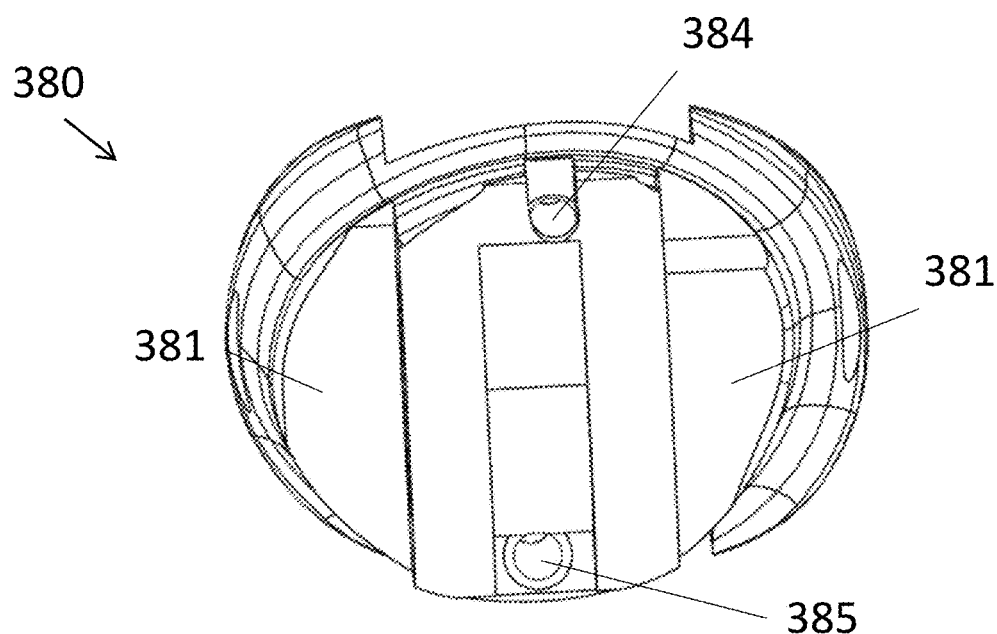
Figure 20A:
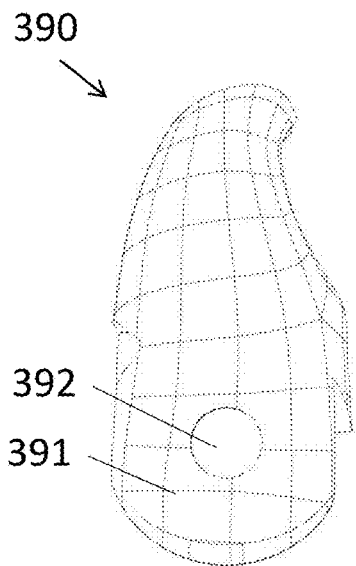
FIGS. 20A-H are views of a tip of the finger of FIGS. 17A-D.
Figure 20B:
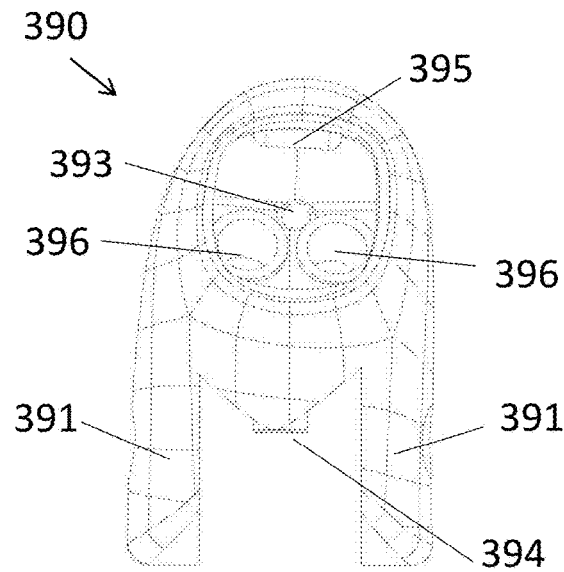
Figure 20C:
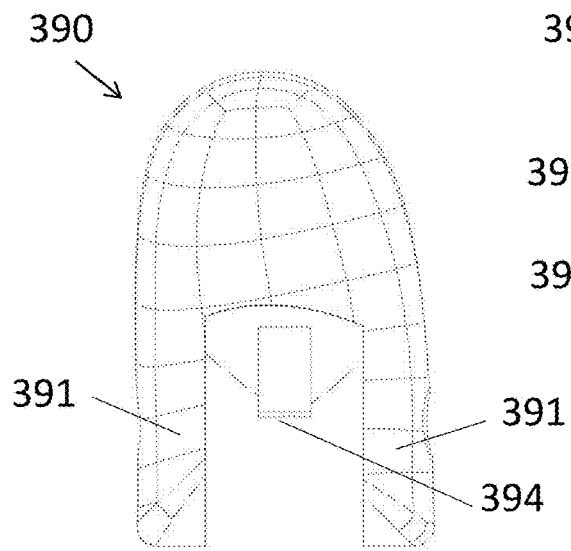
Figure 20D:
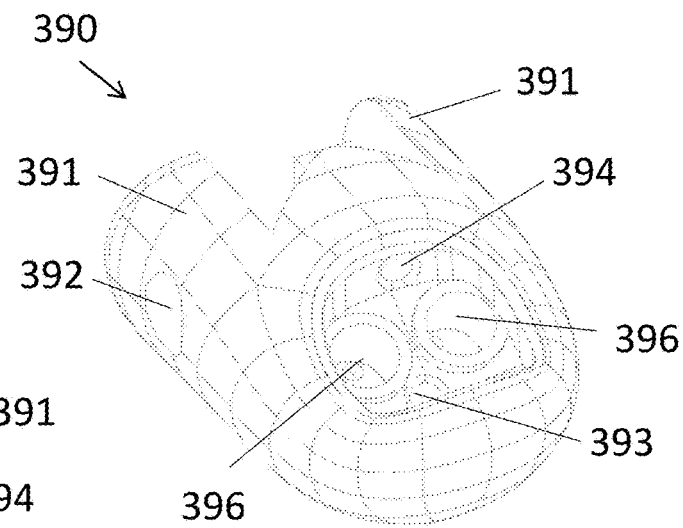
Figure 20E:
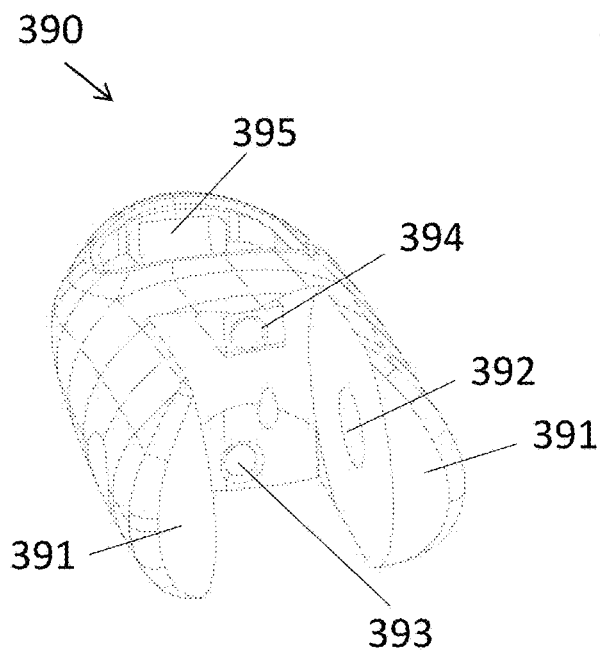
Figure 20F:
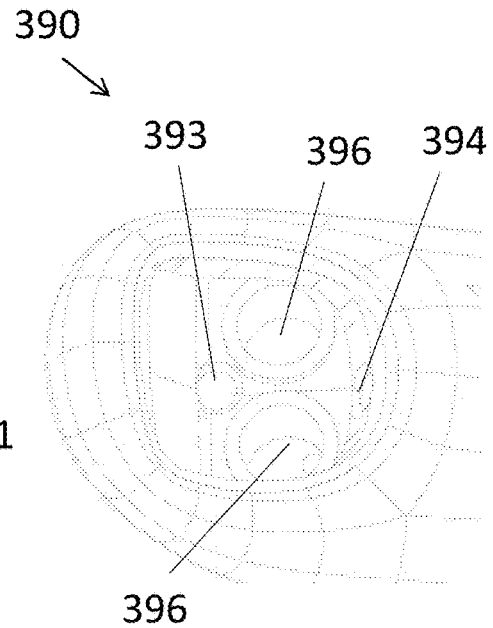
Figure 20G:
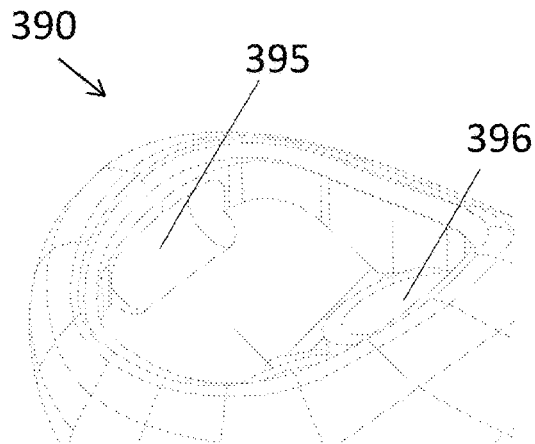
Figure 20H:
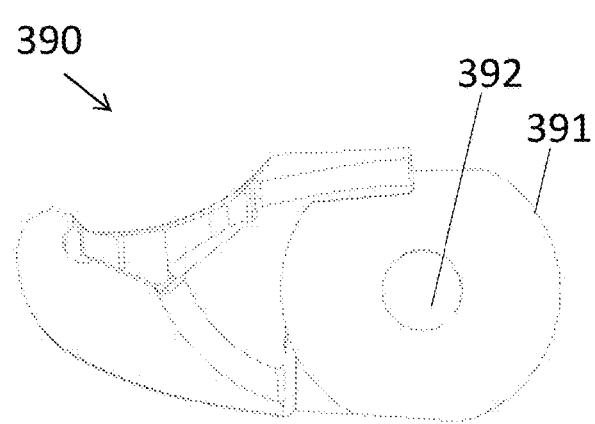
Figure 21A:
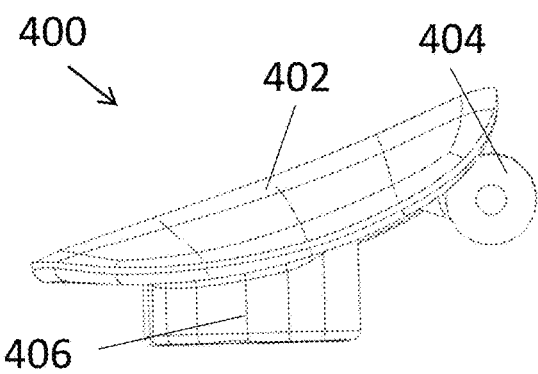
FIGS. 21A-E are views of a nail for use with the fingertip of FIGS. 20A-H.
Figure 21B:
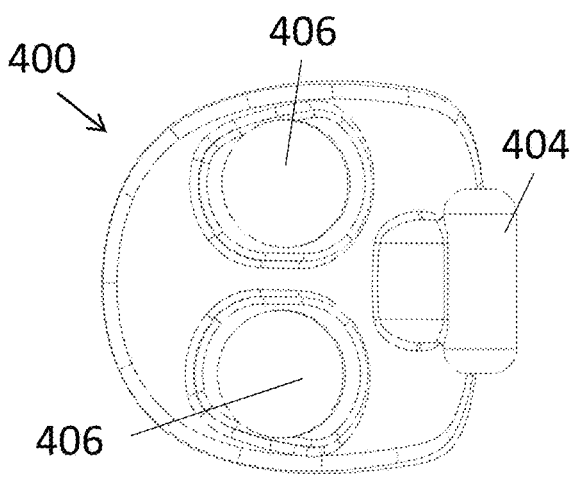
Figure 21C:
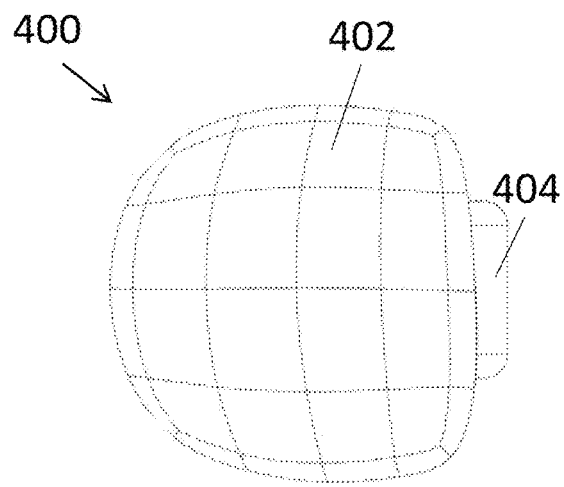
Figure 21D:
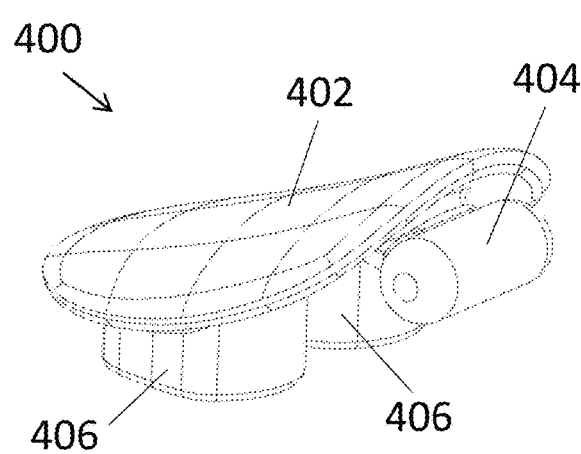
Figure 21E:
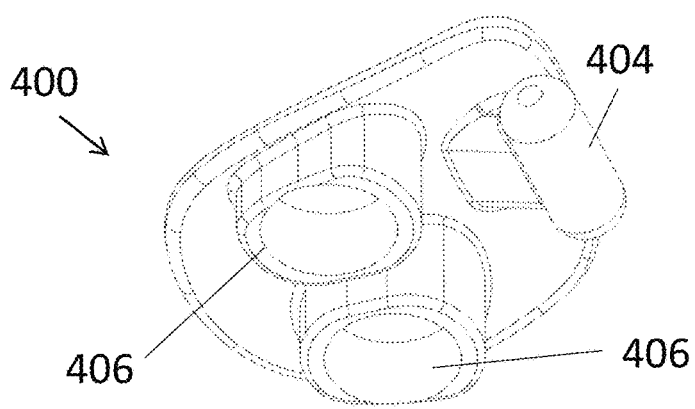

Referring now to the bottom view of middle portion 380 of FIG. 19E, an anterior tunnel 384 and posterior tunnel 385 may be provided. When middle portion 380 is coupled to finger base 370, anterior tunnel 384 may substantially align with the anterior tunnel 373 of finger base 370, while posterior tunnel 385 substantially aligns with the posterior tunnel 374 of finger base 370. As best shown in FIGS. 19C and 19D, anterior tunnel 384 may be open at the anterior-most portion near the distal end of middle portion 380. Posterior tunnel 385, on the other hand, may be substantially closed between the inlet and outlet ends of the posterior tunnel 385. The prosthetic finger flexion tendon may pass from anterior tunnel 373 through anterior tunnel 384, while the prosthetic finger extension tendon may pass from posterior tunnel 374 through posterior tunnel 385.

FIGS. 20A-H illustrate various views of the fingertip 390 of finger 360. Fingertip 390 may include a proximal portion with two lateral extensions 391, and each lateral extension 391 may include an aperture 392 extending therethrough. Lateral extensions 391 may be sized and shaped to fit over the distal portion of middle portion 380 so that apertures 392 align with apertures 383. A pin or other fastener may pass through apertures 392 and 383 to hingedly couple middle portion 380 to fingertip 390. Lateral extensions 391 may be substantially rounded at their proximal ends to fit within or adjacent correspondingly rounded portions of the middle section of middle portion 380. The coupling between the proximal portion of fingertip 390 and the distal portion of middle portion 380 may substantially mimic the function of the distal interphalangeal joint.

The distal portion of fingertip 390 may be include a hollow compartment and may be open in order to allow access to the compartment. Fingertip 390 may include an anterior tunnel 393 and posterior tunnel 394. Anterior and posterior tunnels 393, 394 may have an outlet that opens into the compartment within fingertip 390. When middle portion 380 is coupled to fingertip 390, the inlet of anterior tunnel 393 may substantially align with the outlet of anterior tunnel 384, and the inlet of posterior tunnel 394 may substantially align with the outlet of posterior tunnel 385. With this configuration, a prosthetic finger flexion tendon extending from the prosthetic forearm 200 through the various anterior tunnels may exit the outlet of anterior tunnel 393 and be tied off or otherwise secured within the compartment of fingertip 390. Similarly, a prosthetic finger extension tendon extending from the prosthetic forearm 200 through the various posterior tunnels may exit the outlet of posterior tunnel 394 and be tied off or otherwise secured within the compartment of fingertip 390. The opening within the compartment of fingertip 390 may provide easy access to one end of the tendons in case maintenance must be performed. However, a removable fingernail 400 may be provided to close the compartment when access is not needed, as described in greater detail below.

FIGS. 21A-E show various views of a fingernail 400 that be removably coupled to fingertip 390. The superior surface of fingernail 400 may include a nail plate 402 that is exposed when fingernail 400 is coupled to fingertip 390. A variety of coupling features may be attached to the inferior portions of fingernail 400 to help removably couple the fingernail 400 to the fingertip 390. For example, a cylindrical connector 404 may be positioned on a front of the fingernail 400, the connector 404 shaped to fit within a corresponding recess 395 in the compartment of fingertip 390. In order to couple fingernail 400 to fingertip 390, connector 404 may first be inserted into recess 395. Then, fingernail 400 may be rotated downward about connector 404 toward fingertip 390. One or more additional connectors 406 on the underside of the fingernail 400 may then contact corresponding connectors 396 in the compartment of fingertip 390. In embodiment, connectors 406 and 396 include magnets such that fingernail 400 is held in place on fingertip 390 by magnetic forces and/or friction forces. Fingernail 400 may be removed by applying force and pulling fingernail 400 away from fingertip 390 if access to the compartment of fingertip 390 is desired. Further, fingernail 400 may be formed of a material that can be easily painted so that a user may apply nail polish to the fingernails 400 if desired.

Figures 22A, 22B:
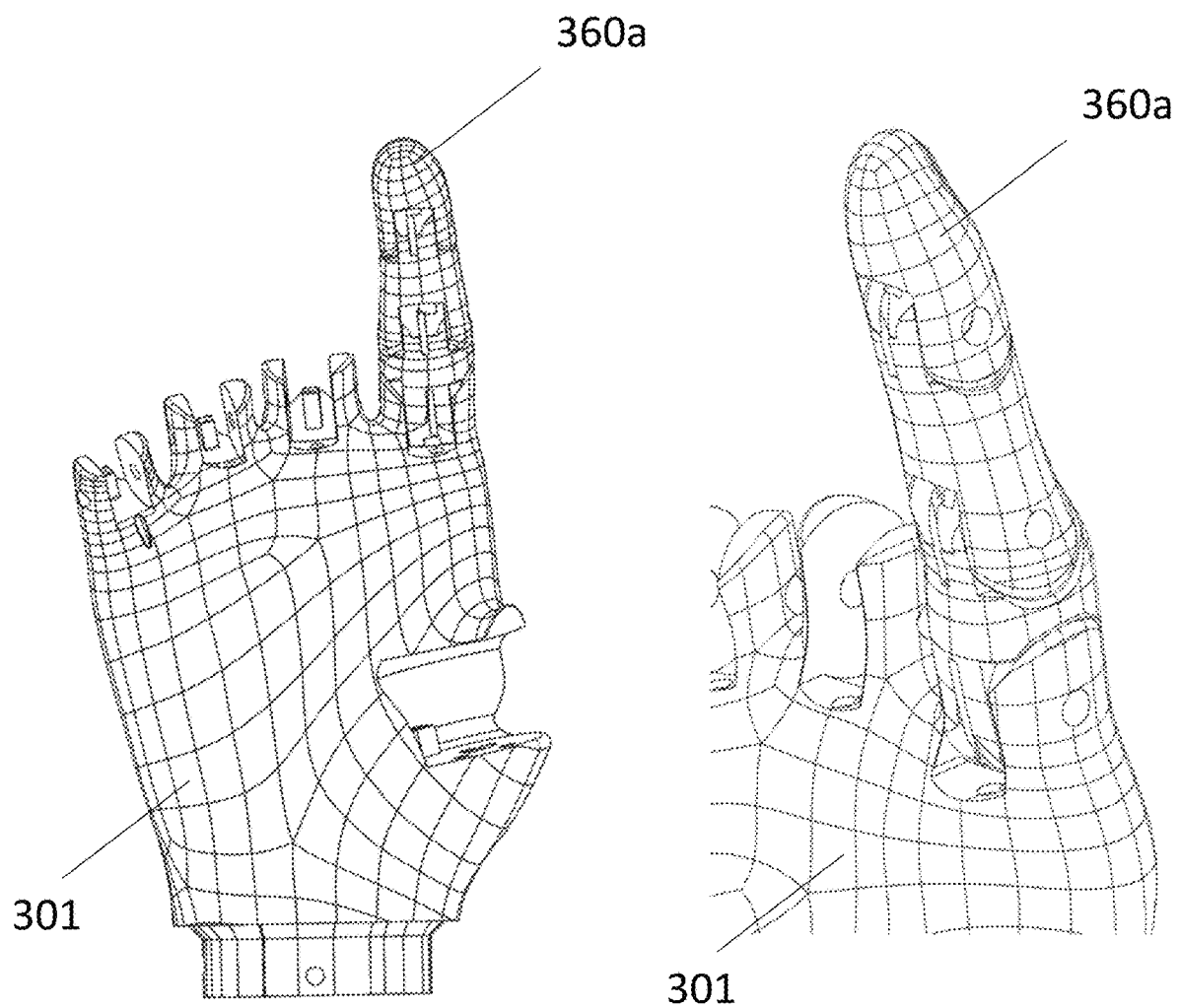
FIGS. 22A-B illustrate a prosthetic finger assembled to the palm in a fully extended condition.
Figure 23A:
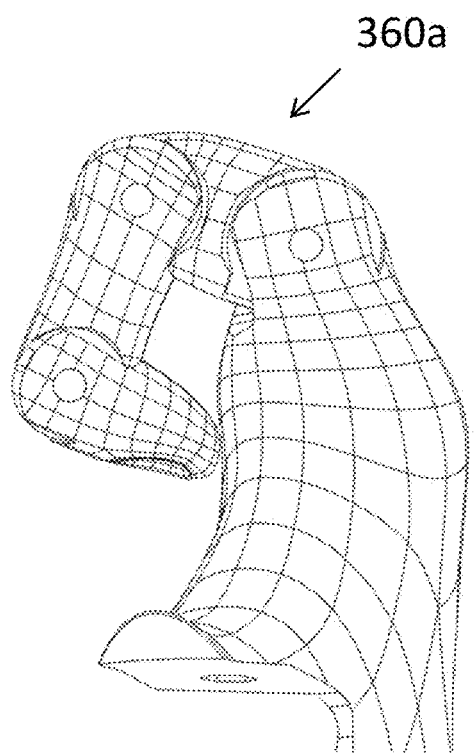
FIGS. 23A-D illustrate the prosthetic finger of FIGS. 22A-B in a fully flexed condition.
Figure 23B:
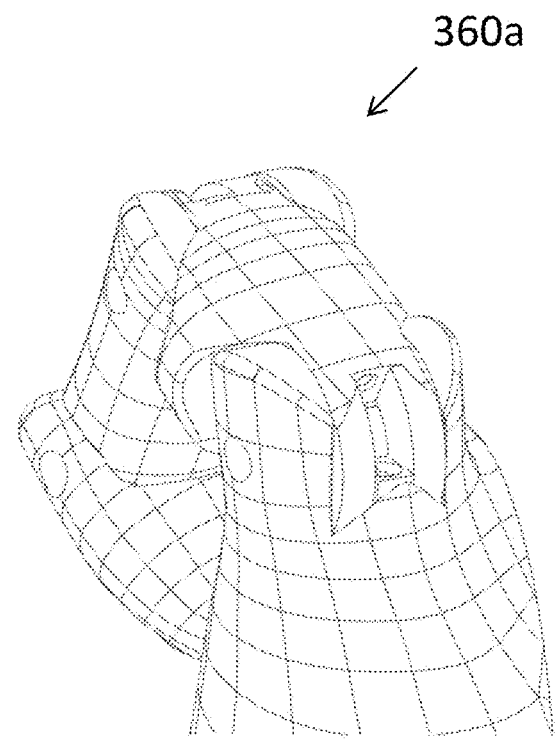
Figure 23C:
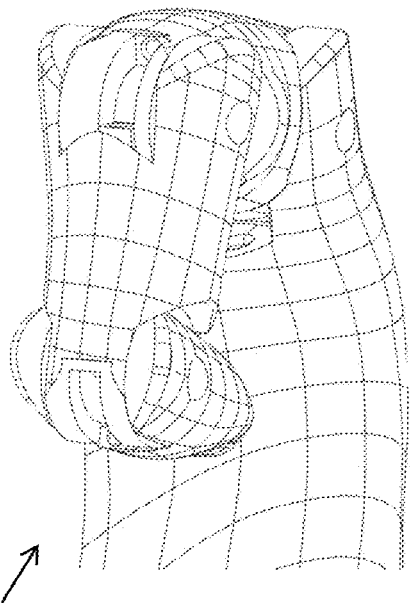
Figure 23D:
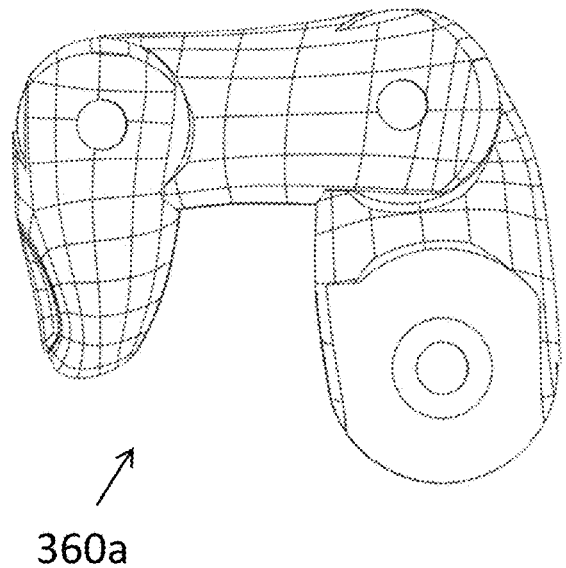

FIGS. 22A-B illustrate the three portions of prosthetic index finger 360a assembled to one another and coupled to palm 301 via finger coupling 303a. In FIGS. 22A-B, index finger 360a is in full extension. As noted above, one prosthetic finger extension tendon may be coupled to a spring that is coupled within forearm 200, with the extension tendon extending through the posterior tunnel 311 within palm 301 corresponding to index finger 360a, and through the various posterior tunnels within finger 360a, the extension tendon terminating and anchored within the fingertip 390. The spring exerts a constant force so that, in the absence of other applied force, index finger 360a tends to be in the full extension position shown in FIGS. 22A-B. FIGS. 23A-D illustrate prosthetic index finger 360a in a condition of full or substantially fully flexion. As noted above, one prosthetic finger flexion tendon may be coupled to an actuator such as linear actuator 282 in forearm 200, with the flexion tendon extending through the anterior tunnel 311 within palm 301 corresponding to index finger 360a, and through the various anterior tunnels within finger 360a, the flexion tendon terminating and anchored within the fingertip 390. The components of finger 360a and the other fingers may be formed to provide certain desired functionality. For example, the shape of the various joints as shown are designed to minimize sharp corners and to maintain a realistic shape when the finger is in the extended condition of FIGS. 22A-B as well as the flexed condition of FIGS. 23A-D. Further, the each finger joint may be structured to allow approximately 90 degrees of flexion relative to the adjacent finger portion (or relative to the palm 301) before a mechanical stop limits further flexion. The order of flexion may also be controlled by controlling mechanical advantage. For example, fingertip 390 may have a smaller diameter than middle portion 380, which in turn may have a smaller diameter than finger base 370. The resulting differential mechanical advantage may result in the finger base 370 flexing relative to palm 301 when linear actuator 282 pulls the prosthetic flexion tendon. As the prosthetic flexion tendon is pulled further, the finger base 370 continues to flex until it hits the mechanical stop at about 90 degrees relative to the palm 301. At that point, if linear actuator 282 continues pulling the prosthetic flexion tendon, the middle portion 380 next begins to flex relative to finger base 370, until middle portion 380 rotates about 90 degrees and hits the mechanical stop. If linear actuator 282 still pulls the prosthetic flexion tendon, the fingertip 390 begins to flex relative to the middle portion 380, until it flexes about 90 degrees relative to the middle portion 380 and hits the mechanical stop, resulting in the full available flexion shown in FIGS. 23A-D. This ordered flexion allows for a more natural gripping motion for a user using the prosthetic extremity 10. It should be noted that, as the three portions of finger 360 flex relative to one another or relative to the palm 301, the open portions of the anterior tunnels allow for the prosthetic flexion tendon to move to facilitate the desired flexing motion. Other components may be provided to facilitate the motion, such as washers or other bearings on the pins that coupled the portions of finger 360 to one another or to the finger coupling 303.

Figure 24A:
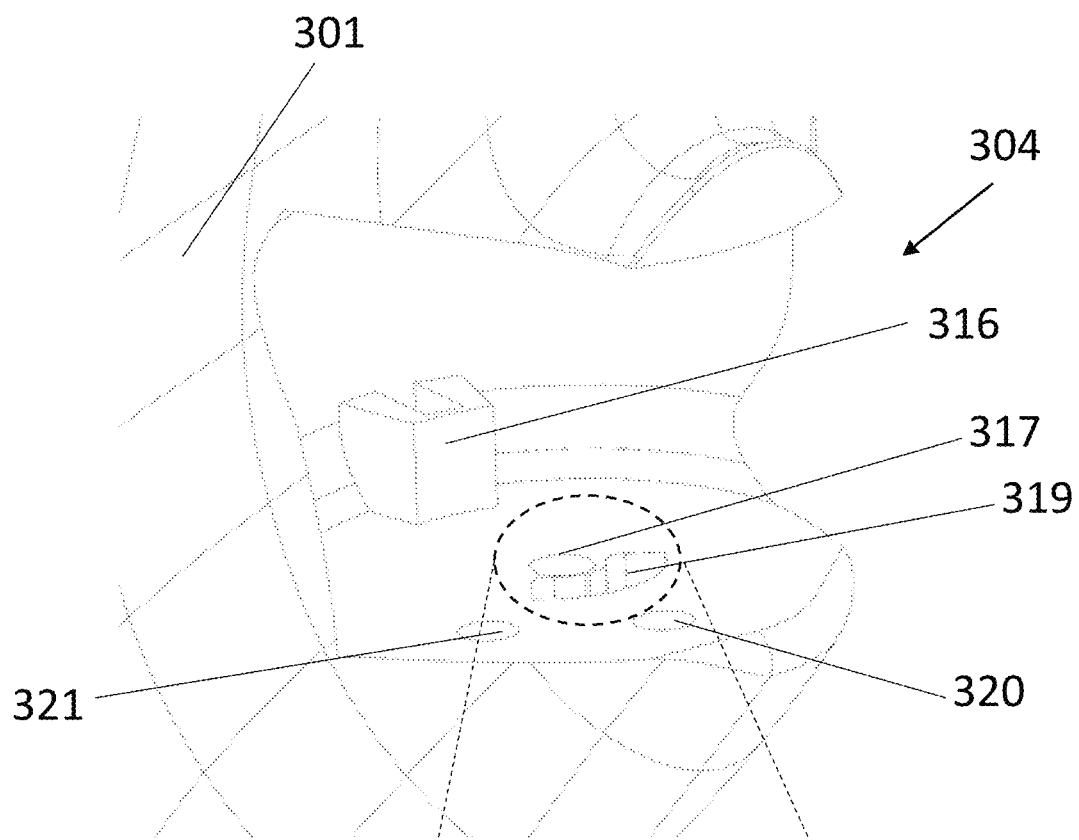
FIGS. 24A-C are views of portions of the thumb coupling of the palm of FIGS. 12A-D.

FIG. 24A is an enlarged view of the thumb coupling 304 of palm 301. Thumb coupling 304 may be substantially in the shape of a recessed cylinder or a portion thereof. The recessed cylindrical shape may include a proximal circular surface shown in FIG. 24A and a distal circular surface shown in FIG. 24C, although it should be understood that these surfaces need not be perfectly circular. Thumb coupling 304 may include a protrusion 316. As is described in greater detail below, protrusion 316 may serve to limit an amount of rotation of thumb 330, and may also house a sensor such as a Hall Effect sensor to sense what rotational position the thumb 330 is in at any moment. The proximal surface may include a central aperture 317 that is aligned with a central aperture 318 in the distal surface of thumb coupling 304. A pin or other fastener may extend through both of these apertures 317, 318 and through a base 340 of the thumb 330 so that the thumb 330 may rotated about that pin.

Figure 24B:
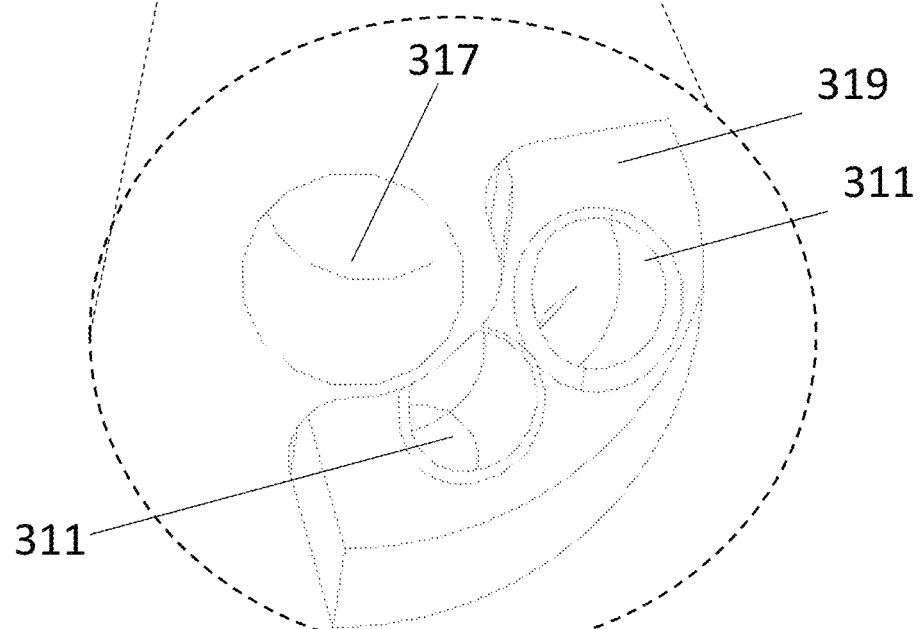
Figure 24C:
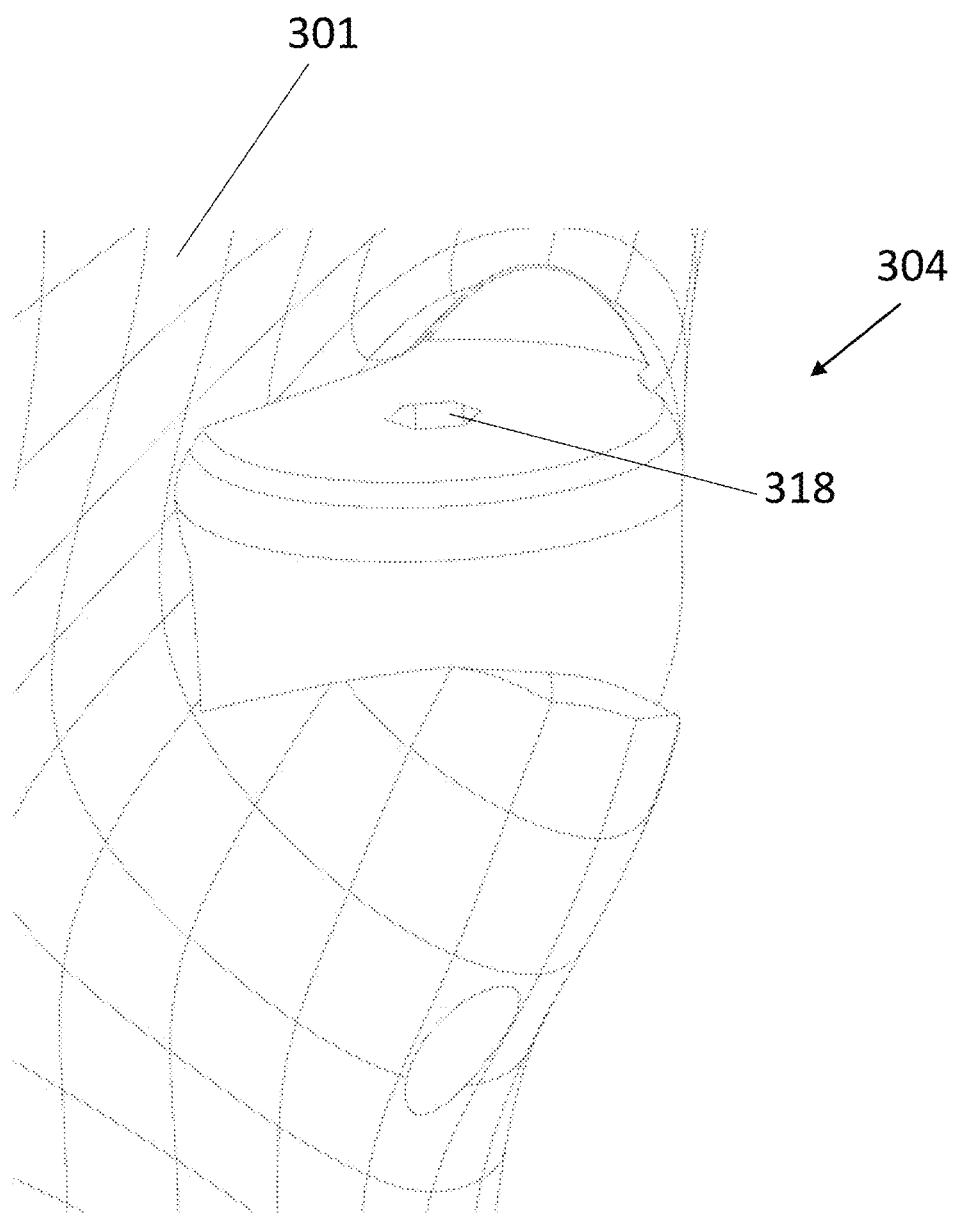

Referring to FIGS. 24A-B, an arcuate recess 319 may be positioned within the proximal surface of thumb coupling 304. Arcuate recess 319 may include therein the outlets of two tendon tunnels 311, corresponding to a prosthetic thumb flexion tendon and a prosthetic thumb extension tendon. As is described in greater detail below, thumb 330 may be capable of rotation in addition to flexion and extension, and the additional space provided by arcuate recess 319 may help ensure that the prosthetic thumb flexion and extension tendons have space to move as the thumb 330 is rotated. The proximal surface of thumb coupling 304 may include two additional apertures 320, 321. As is described in greater detail below, apertures 320, 321 may be sized and positioned two receive a locking pin of thumb 330 so that, when the locking pin of the thumb 330 is received within aperture 320, thumb 330 is locked into one rotational position, while when the locking pin of the thumb 330 is received within aperture 321, thumb 330 is locked into a different rotational position.

Figure 25A:
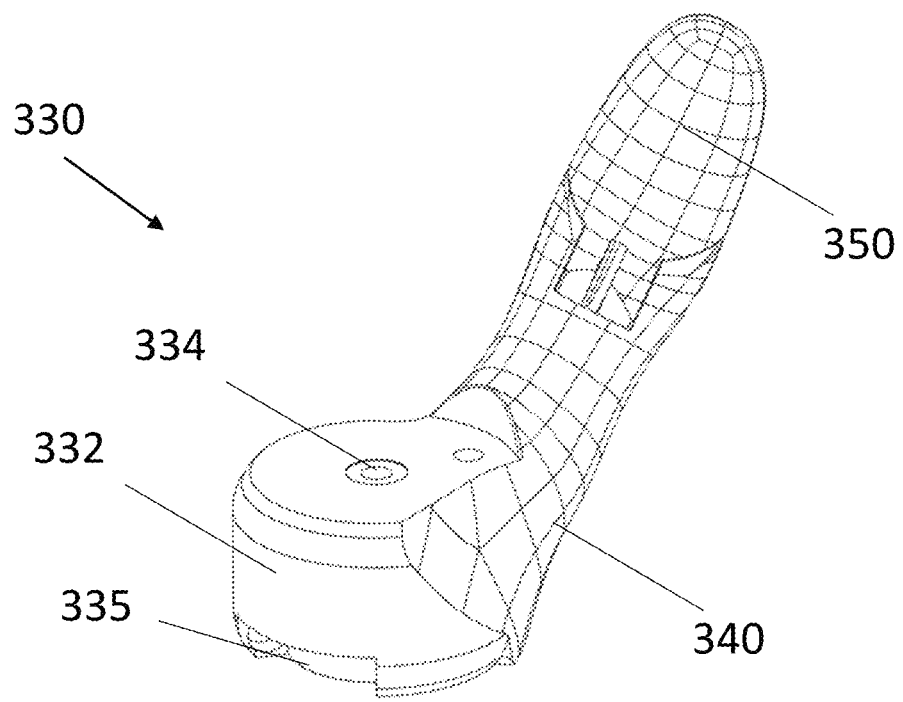
FIGS. 25A-B are views of the prosthetic thumb of the hand of FIGS. 11A-C.
Figure 25B:
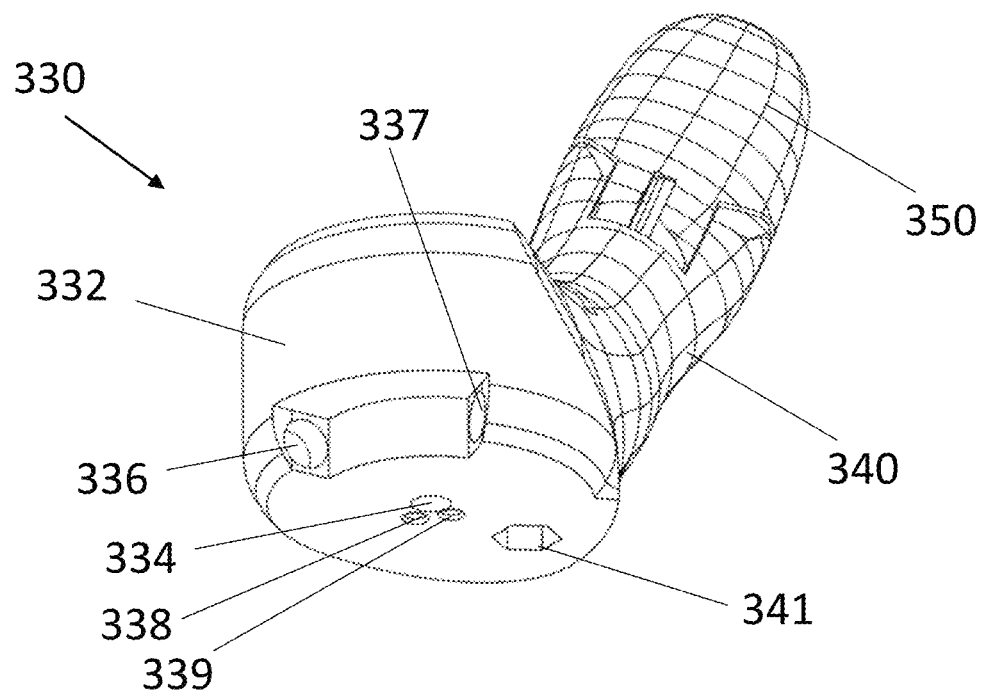

FIGS. 25A-B show two views of prosthetic thumb 330. Generally, thumb 330 may include a thumb base 340 and a thumb tip 350. Base 340 may include a substantially cylindrical member 332 with a central aperture 334 extending therethrough. Base 340 may be coupled to thumb coupling 304 via a pin extending through aperture 334 and into apertures 317, 338 of thumb coupling 304, with the base 340 being rotatable about that pin. Washers or other bearings may be positioned on or adjacent central apertures 334 in order to facilitate rotation of base 340 against thumb coupling 303. A proximal side of cylindrical member 332 may include an arcuate recess 335 into which protrusion 316 is adapted to extend. As thumb 330 is rotated within thumb coupling 304, the two faces 336, 337 of recess 335 may limit the extent to which thumb 330 may rotate in either direction. If a Hall Effect sensor is provided within protrusion 316, the faces 336, 337 of recess 335 may each include a magnet so that the Hall Effect sensor is able to detect the rotation position of thumb 330 within thumb coupling 303.

The proximal face of cylindrical member 332 may include two apertures 338, 339 adapted to receive a prosthetic thumb flexion tendon and a prosthetic thumb extension tendon therethrough, respectively. When thumb 330 is coupled to thumb coupling 304, apertures 338, 339 may generally be located near or adjacent arcuate recess 319, such that even during rotation of thumb 330, the prosthetic thumb tendons are not damaged. Another aperture 341 may be included in the proximal face of cylindrical member 332. Aperture 341 may receive a pin, such as a spring biased pin, therein. The pin within aperture 341 may extend into aperture 320 in a first rotational position of thumb 330, or aperture 321 in a second rotational position of thumb 330. Preferably, the pin is biased such that, upon aligning with either aperture 320 or 321, the pin pops or otherwise moves within the aperture to limit additional rotation of thumb 330. In some embodiments, the biasing force is relatively low so that, although thumb 330 will remain in one of the two rotational positions when the pin is within aperture 320 or 321 in the absence of additional intentionally applied force, applying manual rotational forces to the thumb 330 overcomes the friction force exerted by the pin and the thumb 330 is manually moveable to the other rotational position. In some embodiments, aperture 341 may include a recess such as a hexagonal recess to accept a nut therein, and the pin may be threaded into the nut within apertures 341 in order to adjust the amount of biasing force provided by the pin in aperture 341.

Figure 26A:
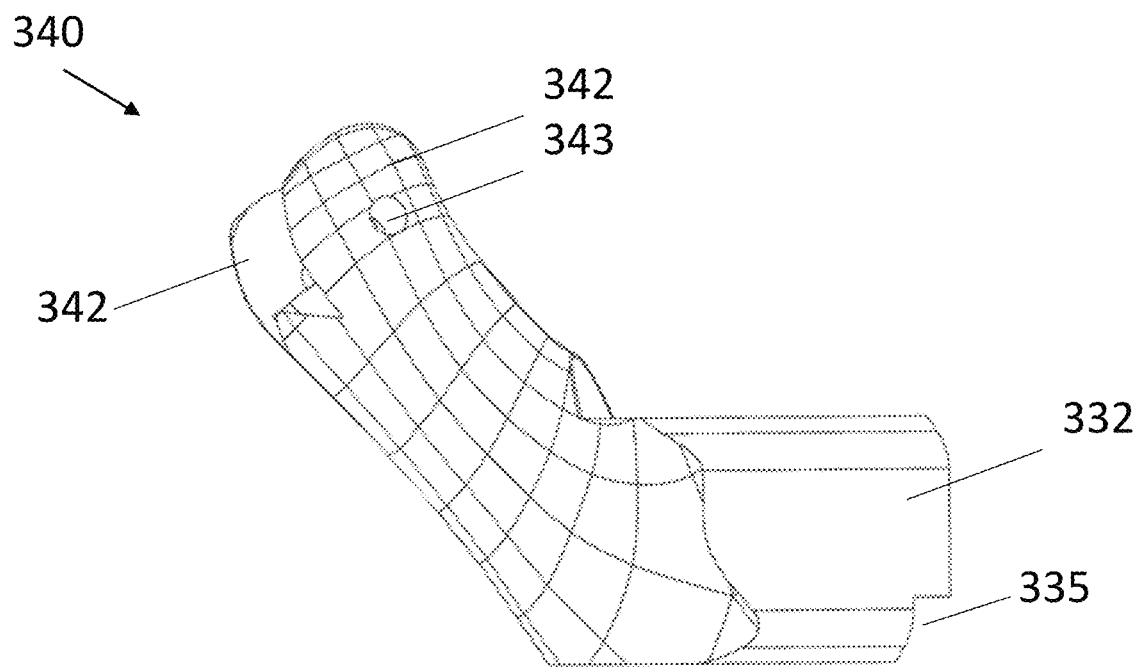
FIGS. 26A-F are various views of the base of the thumb of FIGS. 25A-B.
Figure 26B:
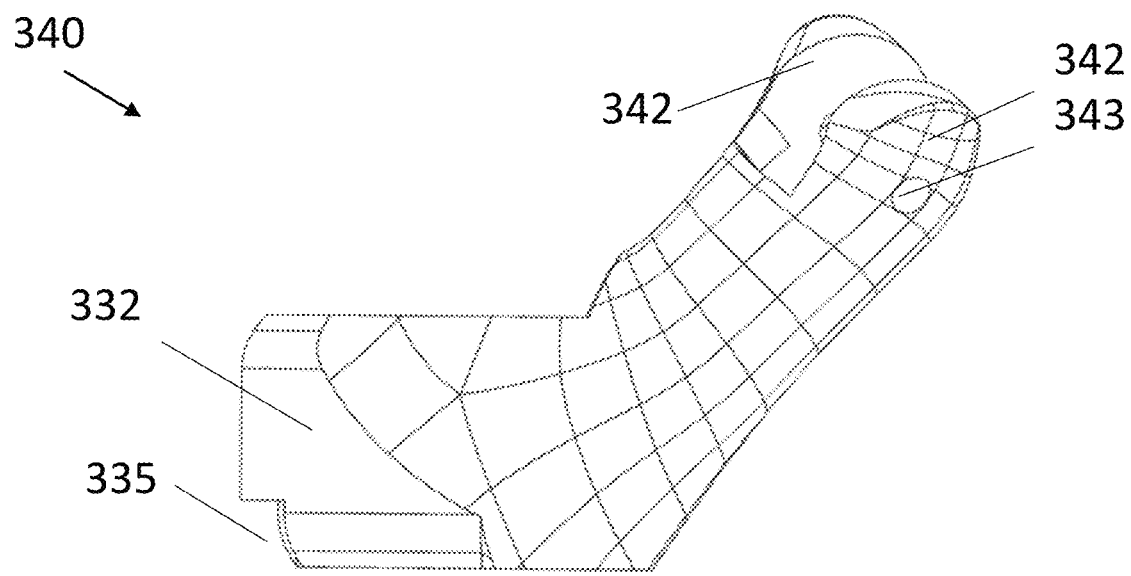
Figure 26C:
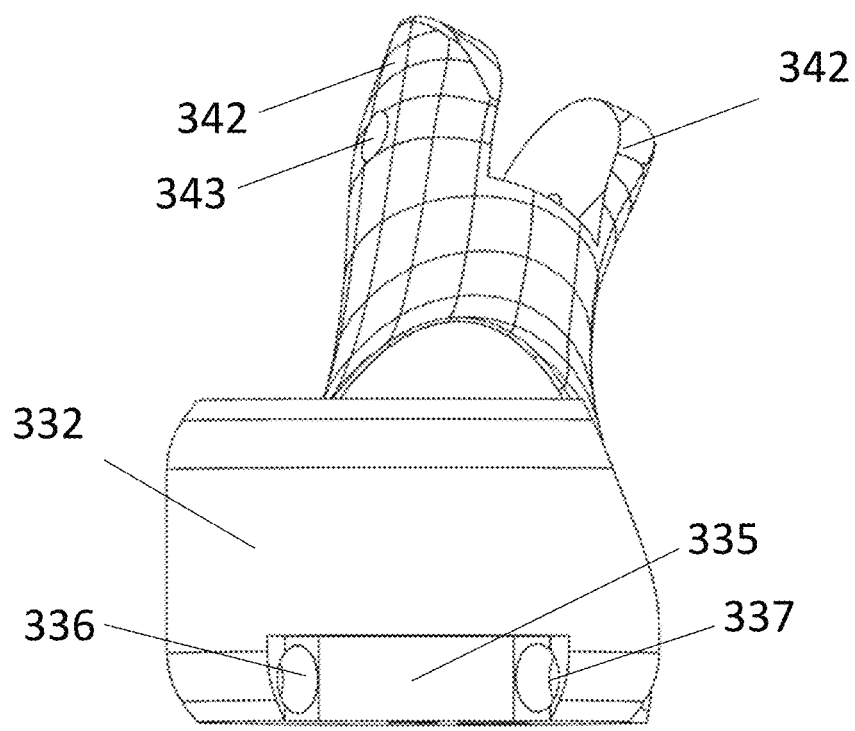
Figure 26D:
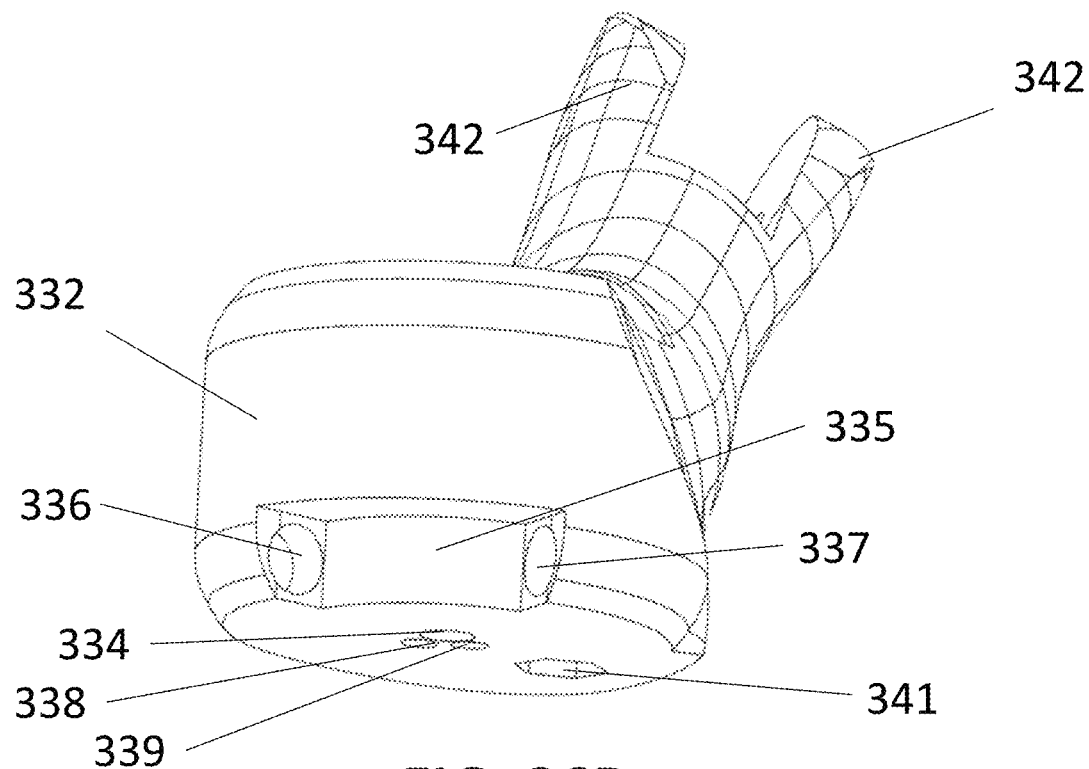
Figure 26E:
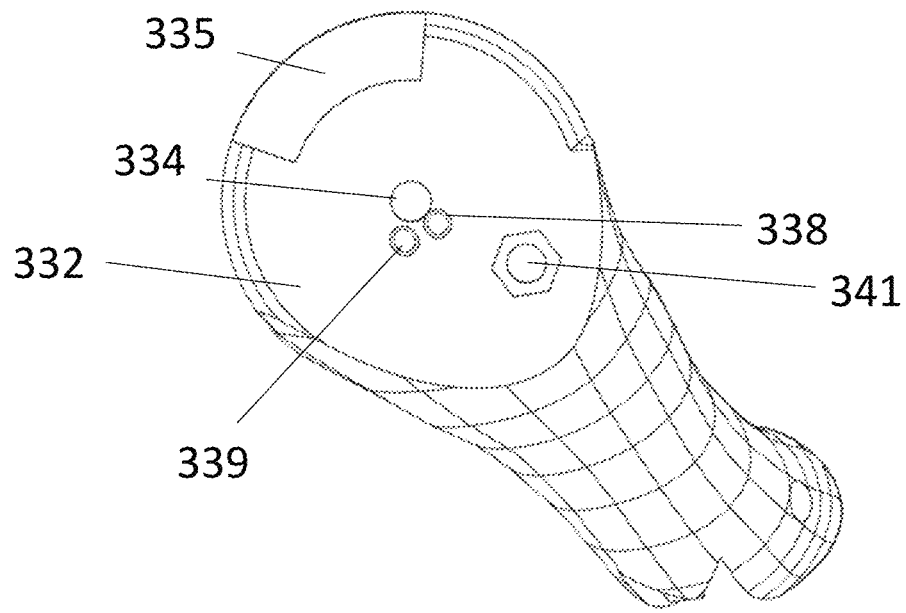
Figure 26F:
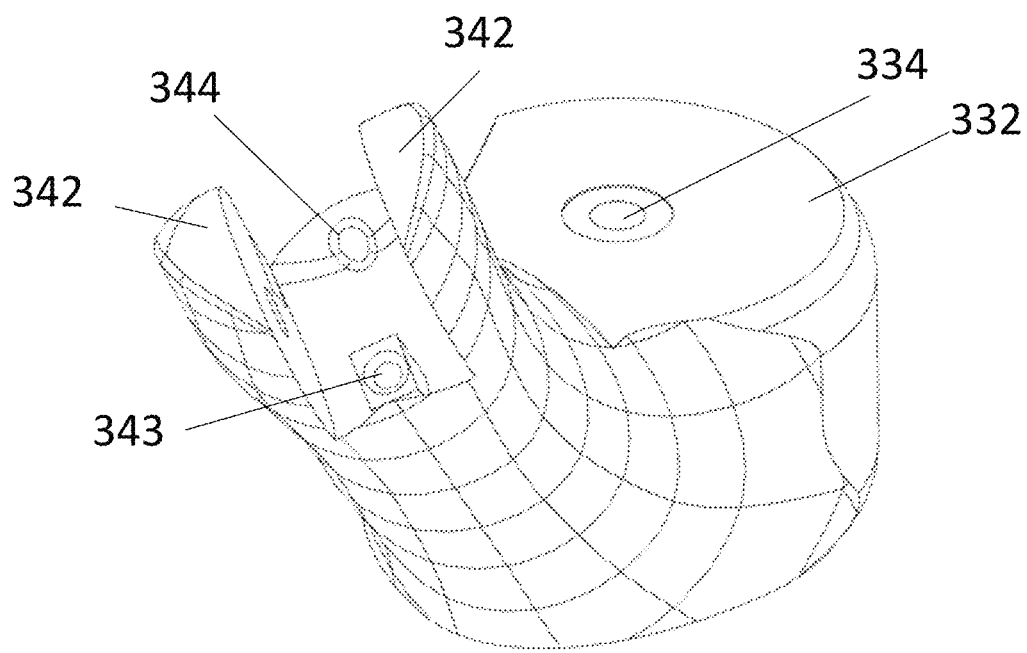

Referring to FIGS. 26A-F, base 340 may include two lateral extensions 342 each having an aperture 343 extending therethrough. Similar to finger base 370, the extensions 342 of thumb base 340 may be shaped and positioned to receive a proximal portion of thumb tip 350 therein, with a pin coupling the thumb base 340 to the thumb tip 350 to allow for flexion or extension of the thumb tip 350 about the pin. Referring to FIG. 26F, thumb base 340 may include a posterior tunnel 343 for receiving a thumb extension tendon therethrough and an anterior tunnel 344 for receiving a thumb flexion tendon therethrough, similar to the corresponding channels described for finger 360.

Figure 27A:
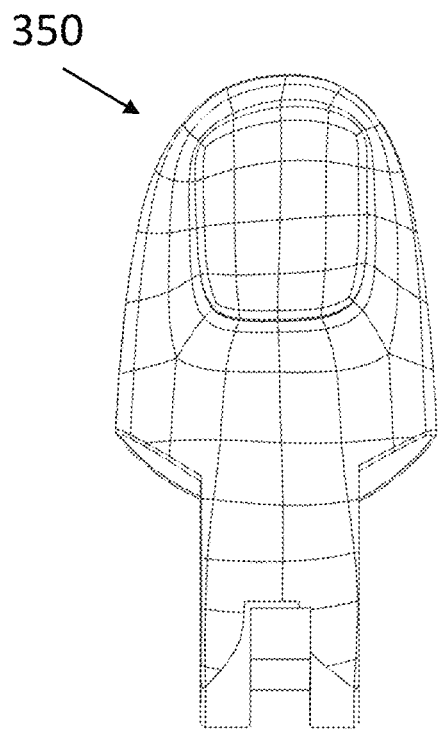
FIGS. 27A-E are various views of the tip of the thumb of FIGS. 25A-B.
Figure 27B:
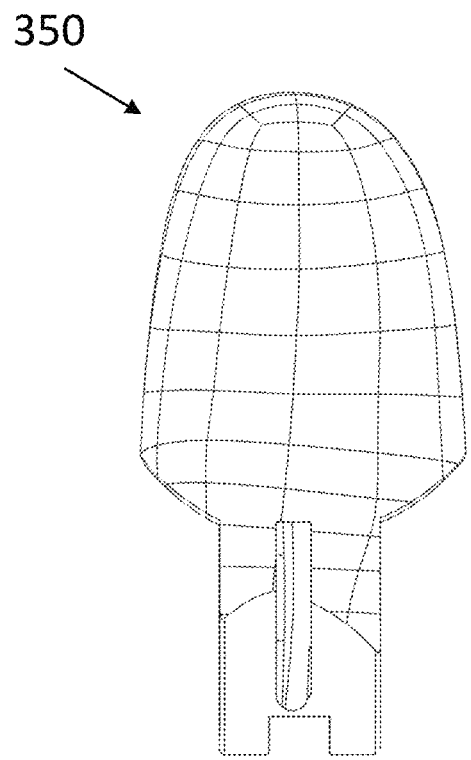
Figure 27C:
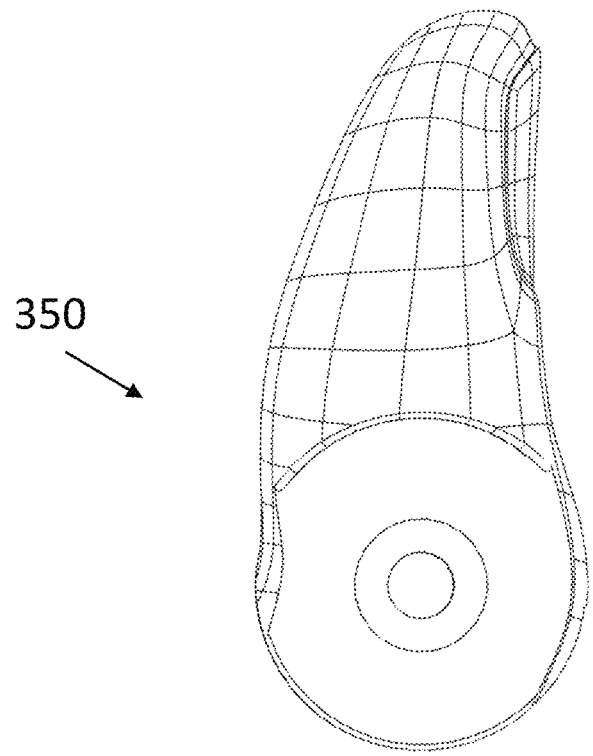
Figure 27D:
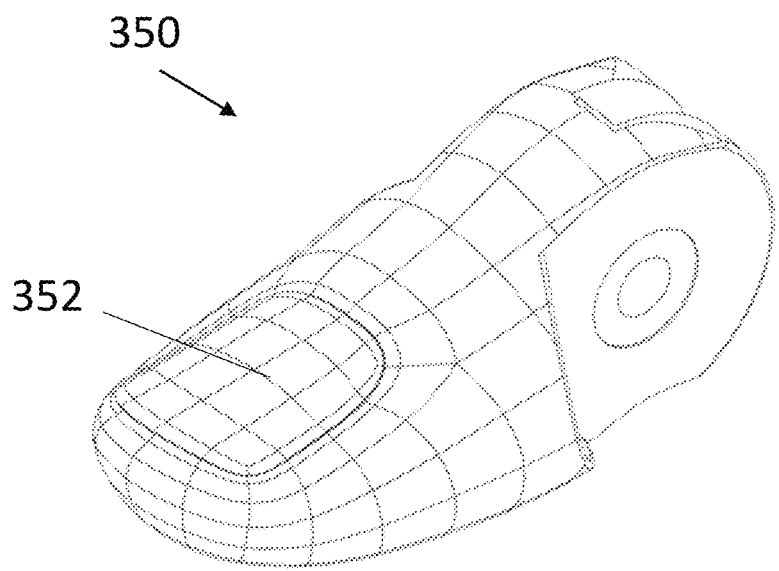
Figure 27E:
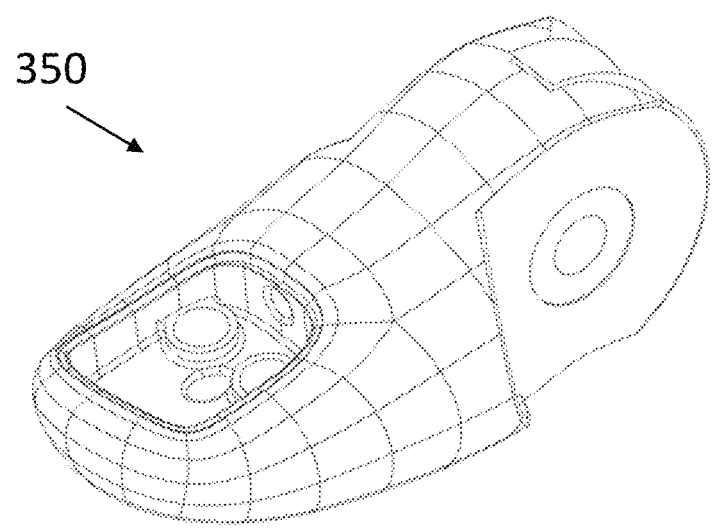

FIGS. 27A-E show various views of thumb tip 350. Thumb tip 350 may include a central aperture for coupling to the a pin extending through extensions 342 to allow for tip 350 to flex or extend relative to base 340. Thumb tip 350 may be substantially similar to fingertip 390 and is thus not described in significant detail herein. However, it should be understood that a thumb flexion tendon and thumb extension tendon may pass through thumb tip 350 into a compartment below thumb nail 352, which may be removable similar to finger nail 400 as shown in FIG. 27E. The thumb flexion and extension tendons may be anchored within the compartment beneath thumb nail 352 to provide for extension or flexion of thumb tip 350 relative to base 340 in a similar fashion as described above for finger 360. Thumb nail 352 may also be substantially similar to fingernail 400 and may couple to thumb tip 350 the same way or substantially the same way which fingernail 400 couples to fingertip 390.

Figure 28A:
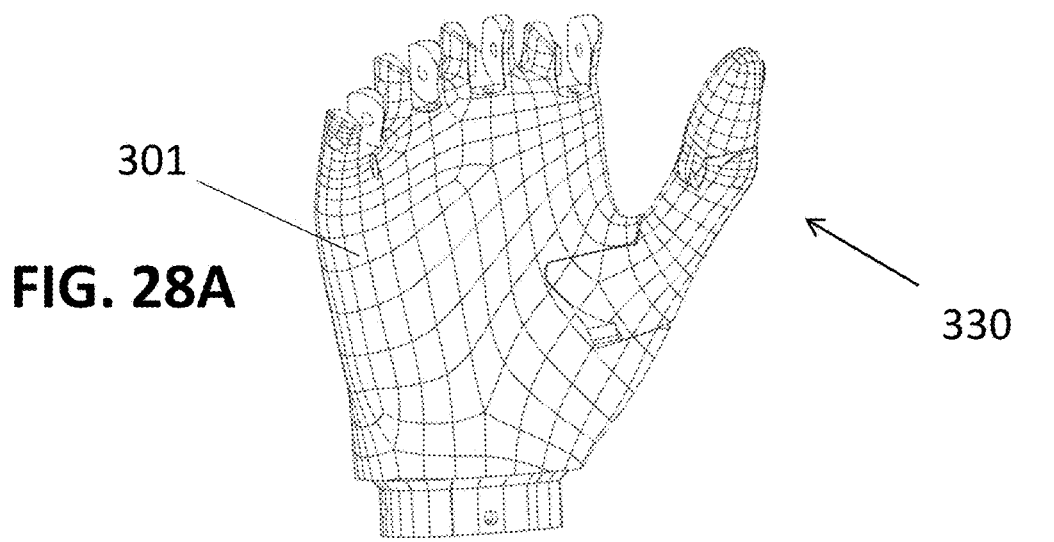
FIGS. 28A-C show the thumb of FIGS. 25A-B coupled to the palm of FIGS. 12A-D in different rotational positions.
Figure 28B:
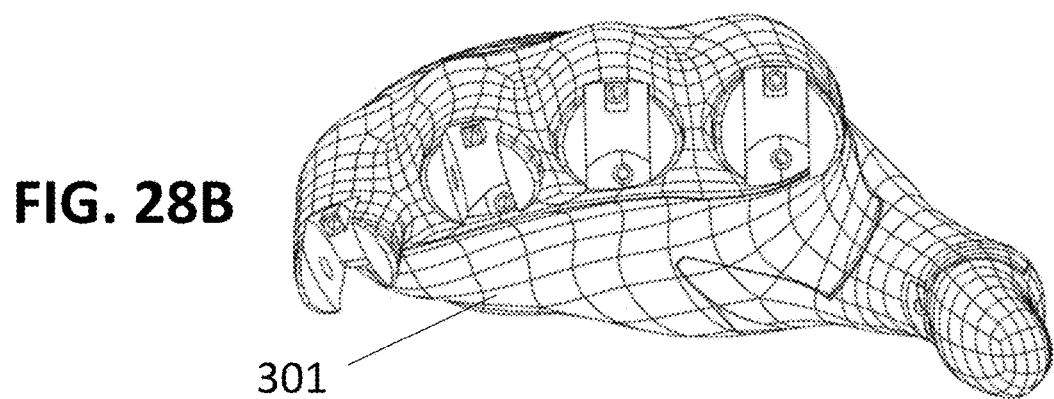
Figure 28C:
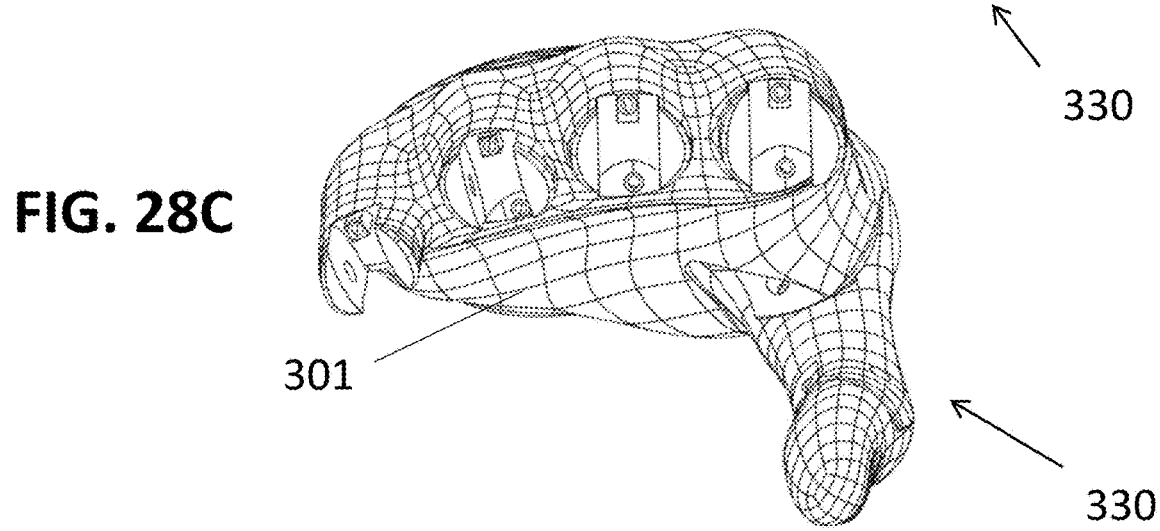
Figure 29A:
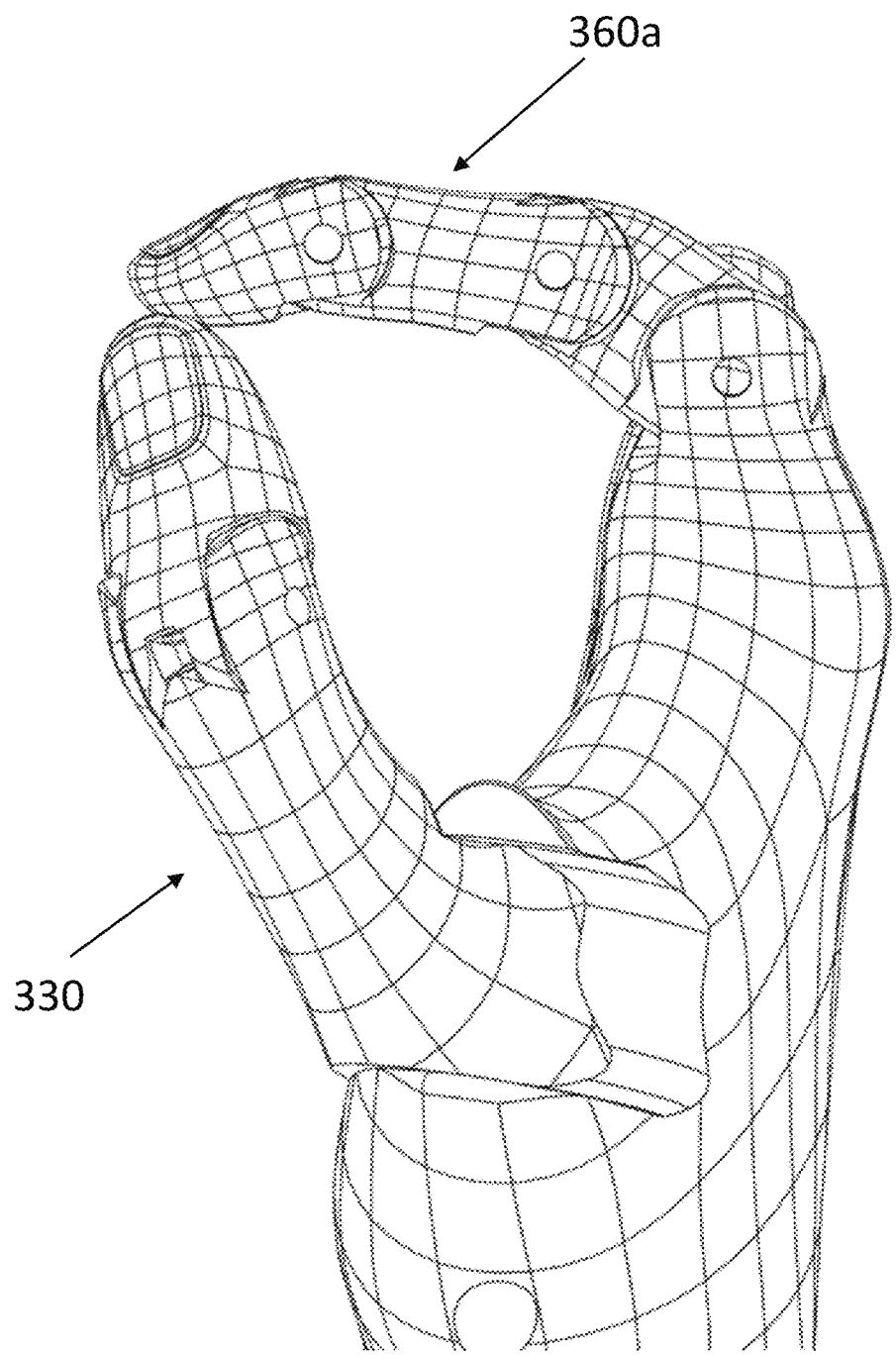
FIGS. 29A-C illustrate possible grips between the prosthetic thumb and prosthetic index finger.
Figure 29B:
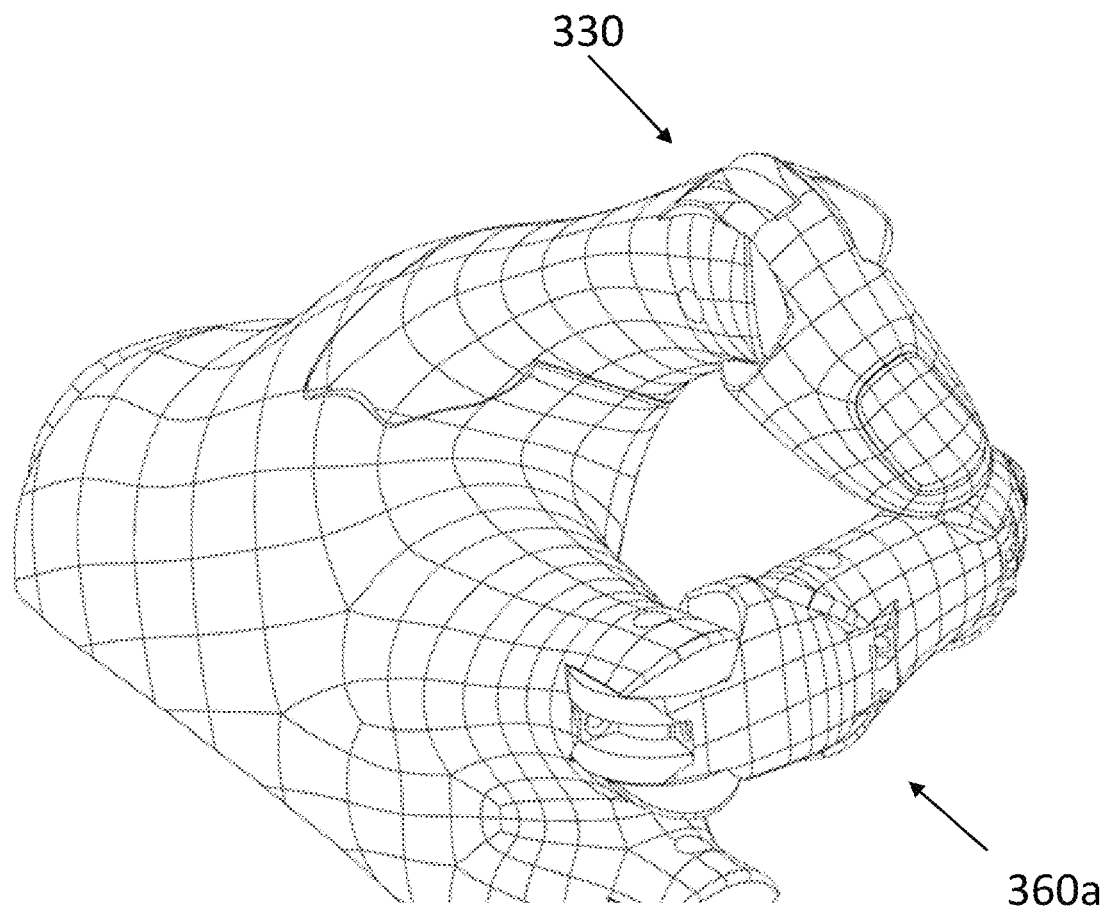
Figure 29C:
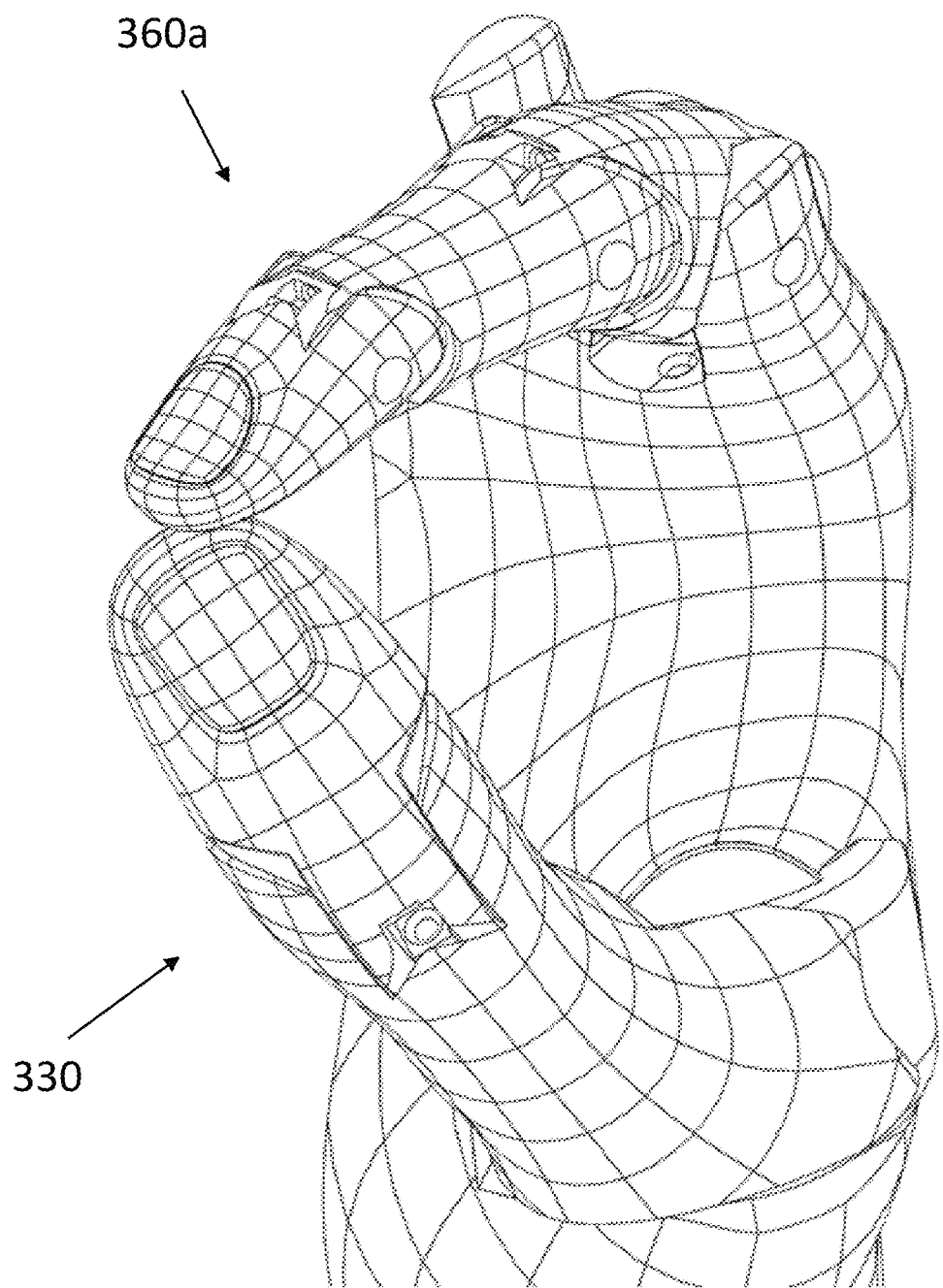

FIGS. 28A-B show thumb 330 assembled to palm 301 in a first rotation position with the locking pin extending from aperture 341 into aperture 320 of thumb coupling 303. As noted above, in this position, the thumb 303 generally remains in this rotational position until an intentional rotational force is applied to the thumb 303 to disengage the pin from aperture 320. After disengaging the pin from aperture 320, thumb 303 may be further rotated until the locking pin is positioned adjacent aperture 321 and springs and locks into aperture 321, locking thumb 330 into the second rotational position shown in FIG. 28C. It should be understood that in either rotational position of thumb 330, pulling the prosthetic thumb flexion tendon, for example via actuating a linear actuator 282, the thumb tip 350 will flex with respect to thumb base 340. Similarly, in the absence of other forces, in either rotation position of the thumb 330, the force applied by a spring to the prosthetic thumb extension tendon will tend to cause the thumb tip 350 to extend relative to the thumb base 340. Similar to the fingers 360a-d described above, thumb 330 may include mechanical stops so that thumb tip 350 is capable of a maximum of about 90 degrees of movement between flexion and extension. FIGS. 29A-C illustrate some grips that are possible between prosthetic thumb 330 and prosthetic index finger 360a.

With much of the structure of prosthetic extremity 10 having been described above, controls for a user to control the movement of fingers 360a-d and thumb 330 are described in additional detail. As noted above, for a user whose arm is amputated distal to the elbow joint, the user may position the prosthesis 10 on the body with the proximal socket 110 attached to the upper arm and the distal socket 150 compressed over the residual forearm, with or without the help of elastic, straps, or additional attachment means.

One or more sensors may be provided on distal socket 150 to be in direct or indirect contact with the user's residual limb in order to assist the user in providing input for controlling prosthetic hand 300. For example, a force sensor may be used to sense the force of a muscle contraction by the user. When the user flexes the muscle, the muscle changes shape and can expand. The force sensor(s) may work when a force is exerted from the user's muscle onto the surface of the force sensor(s), the force being transmitted into layers of a conductive polymer that change resistance based on the amount of force applied. One or more force sensors may be anchored to an elastic band, for example on a surface of distal socket 150 intended to contact the user's residual limb, the elastic band helping to provide consistent pressure of the force sensor to the user's skin. The reading of the force sensor(s) once the elastic band is in the desired position and the user's muscles are in a resting state may be used as a zero point within software to track changes. A small cylindrical shaped foam piece may also be used to concentrate the force from the user's muscle to the force sensing area of the force sensor. By using a smaller diameter piece of foam than the diameter of the sensing area, the reading is amplified and smaller changes may be detected. When a muscle is flexed, the muscle pushes on this piece of foam that pushes on the force sensor. This may also provide proportional data of the amount of muscle activity. In other words, instead of being a binary on/off signal, this above-described sensor configuration may provide data regarding the intensity of the muscle flex, the duration of flexing, and any kind of ramping of the flexing. This data may be used, alone or in combination with other data, to provide information to a controller, such as a controller within the cover 260 of prosthetic forearm 200, and in turn to accurately control the various actuators 282 to accurately flex or extend the fingers 360*a-d* and thumb 330. It should be understood that any sensors in socket 100 may be coupled to electronics within prosthetic forearm 200, either wirelessly or in a wired fashion as described above.

Another sensor that may be used in order to help a user control the flexion and extension of fingers 360*a-d* and thumb 330 is an electromyography ("EMG") sensor, which detects the electrical potential generated by muscle cells. In one example, the EMG sensor may include three surface electrodes, including positive, negative, and reference. The positive and negative electrodes may be placed on the desired muscle and the reference electrode may be placed somewhere without muscles, such as the elbow area. The EMG sensor may detect muscle activity and provide information to the electronics within prosthetic forearm 200 in order to control the actuation of actuators 282 and, in turn, control the flexion and extension of fingers 360*a-d* and thumb 330.

In one embodiment, one or more force sensors may be used along with one or more EMG sensors. In one example, the electrodes of the EMG sensor may be placed on the force sensors so that when a user flexes the muscle, the electrodes make consistent contact and push into the force sensor. This may provide two different types of data to analyze and to translate into desired movement of the prosthetic hand 300. This combination has been found by the inventor to provide better results than using force sensors and EMG sensors independently. It should be understood that for each of the examples above, the linear actuators 282 may be individually controlled, so that the user may individually control the thumb 330, index finger 360*a*, and the remaining fingers 360*b-d*.

Additional features may be activated other than through muscle control. For example, as noted above, forearm cover 260 may include a recess 274 for a push button. The push button may provide any desired functionality when pressed. In one example, pressing the push button activates the actuators 282 to cause flexion in the fingers 360*a-d* and thumb 330, so that the prosthetic hand 300 may be used to grip an object without the user initiating muscle flexing to cause the actuation. The button may be binary in the sense that pressing the button once causes flexion, and pressing it again causes extension. In other embodiments the button may be force sensitive where pressing the button with more force causes the fingers 360*a-d* and thumb 330 to flex with greater force. Such a button may in some embodiments be coupled with indicators, such as an LED or an array of LEDs to provide visual feedback to the user to communicate a current state of the device, calibration, power level, and/or detected errors.

As noted above, in the illustrated embodiment, most or all of the electronics are coupled to or positioned within the interior of forearm cover 260, similar to the picture shown in FIG. 10B. One or more processors or controllers may be coupled to the various actuators 282 to provide actuation of the prosthetic flexion tendons as described above to flex the fingers 360*a-d* or the thumb 330. The connection between the processor(s) and the actuators 282 may be any suitable connection such as the ribbons shown in FIG. 10B. Power may be provided to the device by any suitable method. In the illustrated example, a rechargeable battery made from lithium-ion technologies is provided within cover 260. Depending on the size of the user and the prosthetic upper extremity 10, at least a single cell battery may be used. The batteries may be recharged by using an external power source that is connected by a cable to a harness, such as a USB port, a magnetic connector, or other suitable modalities. The batteries can also be charged wirelessly by an inductive charging system including circuity and transmitting and receiving coils. The receiving coil may be placed on the inside of the forearm cover 260 with the main electronics or in another position, such as within the palm 301. The transmitting coil and circuitry may be in the form of a plate on which the prosthetic forearm 200 may rest. Magnets may be used for alignment to ensure the coils are in a desired alignment. These magnets may be imbedded into the charging plate and placed in the prosthetic forearm 200 below the outer surface so that magnets attract each other.

Haptic feedback systems may be integrated into prosthetic extremity 10 to provide various types of information to the user, including device status, battery level, warnings, errors, selections, triggers, and/or force being encountered by prosthetic hand 300 during gripping. A small vibrating motor, similar to what is used in many cell phones, may be provided within cover 260 or another component of prosthetic device 10 to provide the haptic feedback to the user. In one example, the vibration motor is secured to a flat surface inside of the prosthetic forearm 200 so that the vibrations pass through the forearm 200, to the socket 100, and then to the skin of the user. Certain patterns and intensities of vibrations may be used to communicate different information to the user. For example, the device can calculate force that is being exerted on an object by the prosthetic hand 300, and the amount of force is communicated by a varying intensity of vibration, for example with a lower frequency corresponding to a relatively low amount of force and a high frequency corresponding to a relatively large amount of force. Other examples of haptic feedback may include a particular pattern of vibrations being provided when the prosthesis 10 is powered on to inform the user that the device 10 has adequate battery power and is ready to calibrate.

As noted above, force being exerted by prosthetic hand 300 on an object, for example during gripping, may be calculated for various uses, including to inform the user of the amount of force via haptic feedback as noted above. In one example, this force may be calculated by determining via the processor or other appropriate electronics the amount of current being drawn by the actuators 282 and by determining the position of the actuator compared to time of the actuation. For example, when the fingers 360*a-d* or thumb 330 meet an object during flexion, the speed of the flexion slows down to a stall, and the measured current draw of the motor can be correlated to the amount of force being exerted. Force can also be calculated by comparing the position of the actuator 282 to the time from the start of movement. When the fingers 360a-d or thumb 330 meet an object during flexion, they slow down the actuator for a small amount of time. By using a combination of both methods described above, an accurate force can be calculated to use for a force limit and to communicate the force being exerted through haptic feedback. Force limiting may be used to ensure the actuators 282 stop before they exert too much force on the object, as well as to protect components in the prosthesis 10. An alternative or additional way to sense the force from the fingers 360a-d or thumb 330 is to provide force sensors on the fingers 360a-d, thumb 330, and/or the front of palm 301.

One additional benefit of the control systems and methods described above is the creation of a feedback loop, which can result when the user has proportional control of the movement of hand 300, as well as feedback, such as visual or haptic feedback, regarding the force. For example, when the user starts to flex the muscle, the user can typically see a response of the prosthetic hand 300 starting to close. This creates a closed loop that allows the user to control the position of the fingers 360a-d and thumb 330 with more precision. When the fingers 360a-d and thumb 330 meet an object, the user may feel vibrations based on the amount of force from the fingers 360a-d and thumb 330. The inclusion of both visual and haptic feedback regarding this force may provide even further precision in control of the prosthetic hand 300.

As noted above, it is preferable that the portions of prosthetic device 10 that are in contact with a residual limb of the user are user-specific in the sense that they closely complement the contours and shape of the residual limb, and also in the sense that the other components such as the forearm 200 and hand 300 substantially match or mirror the user's other limb if it is intact. Exemplary methods of creating components of prosthetic device 10 are described below.

In one embodiment, to begin creating prosthesis 10, three-dimensional scans of the user's residual limb are performed, as well as three-dimensional scans of the opposite full arm if the arm is available for scanning. These 3D scans may be generated from any suitable 3D scanner, preferably a mobile 3D scanner. The 3D scans preferably also include color data which can be used to 3D-print the components of the prosthesis 10 in a matching color. If the 3D scanner is a mobile scanner, the user can create these scans remotely, with or without the assistance of another person. A mobile application may be used to interface with the 3D scanner, which may allow for live monitoring, starting/stopping a scan, reviewing the scan, and/or submitting a scan. The 3D scan(s) of the user's limbs may be used to generate a custom prosthetic hand 300, forearm 200, and socket 100.

A 3D scan of the residual limb may be used to create a socket 100, and in particular distal socket 150, that is complementary to the shape and contours of the residual limb. As noted above, an offset may be built into distal socket 150 to provide an interface layer for foam or another layer, which may not only increase comfort for the user, but help reduce the effect of any inaccuracies in the scanning process. During the design process, it is preferably to have as much surface area from the distal socket 150 in contact with the user's residual limb, as it must support the weight of the remaining components of prosthetic device 10 and any objects the prosthesis may be lifting.

In one embodiment, a test socket may be produced initially to confirm a desired fit with the user prior to producing a final socket. For example, if the user scans his or her residual limb remotely, that data may be sent to a facility to rapidly print a 3D test socket that may be shipped to the user to confirm fit. In one example, the test socket is 3D printed based on the scan data using a FDM 3D printer with a large nozzle to rapidly print the test socket. Because the initial socket is a test socket, it may be produced more quickly than the final socket. The test socket may be printed the same day the 3D scans are received and it may be shipped to the user to confirm fit. The user may contract the manufacturer to determine if any alterations to the design are required or desired, and a final socket may be 3D printed with higher quality, which may take a longer time, with or without modifications from the shape of the test socket. The final 3D-printed socket may be rigid and may be 3D-printed on FDM 3D printer using clear plastic, which may be preferred or aesthetics compared to, for example, carbon fiber. In other embodiments, flexible plastics or other flexible materials may be used to construct the socket, or a combination of rigid and flexible materials may be used to construct the socket, which may make the socket more universal and have a better fit and relieve points of pressure.

While 3D scan data of the user's residual limb may be used to design the socket 100 (or portions thereof), the 3D scan of the user's opposite limb may be used to design the shape, contours, and dimensions of the prosthetic forearm 200 and hand 300. For example, from the 3D scan data of the opposite limb, specific dimensions may extracted and used to create a proportional forearm 200 and hand 300. These dimensions may include finger length, finger height, finger width, palm length, palm thickness, palm width, wrist circumference, forearm length and various circumferences of the opposite limb.

The measurements extracted from the 3D scans may be input into a master CAD model that has all of the mechanical and robotic features described above already designed in. Measurements may be automatically imported or manually entered into this CAD model to create a new user specific model using the user's specific measurements. For example, the finger length may be entered and the master CAD model would update to match the user's finger length. This methodology allows for rapid creation of custom devices without having to design a custom model for each user.

Once a custom model is generated from the user's measurements from the master CAD model, the individual parts are ready to be made physically by using a 3D printer. A high-end 3D printer is preferably used to provide high levels of accuracy that ensure the mechanisms within the prosthesis 10 are able to function properly. Such a 3D printer may use a secondary support material which may reduce the design constraints of a model. As a result, it is possible to print parts assembled. For example, instead of joining the finger joints together using a pin, an interlocking structure can be printed utilizing the support material, so the parts do not fuse together.

It should be noted that, when printing the prosthetic forearm 200 and hand 30, it may be preferably that the weight of those devices, including components positioned therein, are as close as possible to the weight of the user's residual limb to help avoid creating a lever effect, which may make the device feel heavier to the user. As a result, it should be understood that certain internal components may be positioned in uniquely for each prosthesis 10 to provide desired weights and weight distribution.

It may be preferable to utilize a 3D printer that is capable of printing in full color which allows the outer surface of the prosthesis 10 to match the skin color of the user. In one example, all of the components of prosthesis 10 may be printed in a single color that is extracted from the 3D scan color data. In another example, a texture map may be created from the 3D scan, and the texture map can wrap the CAD model so that a 3D picture is printed on the exterior surfaces of the 3D printed components. This method may provide extreme realism, for example as the user's arm hair, wrinkles, blemishes, freckles, variations in color, veins, etc. may all visually show on the prosthesis 10. Further, by changing the texture of the outer surfaces of the printed components from a smooth surface to a textured surface, a feel can be provided that matches that of skin. For example, small dimples can be added to provide a touch that feels like rough skin or small ridges for finger print ridges. This latter feature may also help with gripping onto objects as well as improving the aesthetics of prosthesis 10. Physical wrinkles and veins can be added too in combination with the coloring/texturing described above to increase the realistic appearance of the prosthesis 10.

The printed prosthesis components may also be coated using a sealant and/or a clear coat to increase the strength and durability of the parts and to make the parts scratch resistance. The clear coat may also be used to match the gloss of skin.

Once the components of prosthetic device 10 are finalized and printed or otherwise manufactured, they may be provided to the user. When the user receives prosthesis 10, the user may go through an initial calibration to ensure the sensors, such as the combined force/EMG sensors, are reading the user's muscle activity correctly. The muscle sensors, described above, are mounted to the inside of the distal socket 150 so that when the user puts the prosthesis on, the sensor is in a consistent position relative to the residual limb and makes contact with the muscle. An application such as a smartphone app may provide live data from the sensor to the user, which may allow the user to place the sensor on the muscle and to test the sensor before mounting the prosthetic forearm 2000 to the socket 100. Once the data meets the requirements the sensor may be mounted, and the prosthesis 10 may be ready to use. Once the device is in position on the user and powered on, the user may be prompted on the mobile application to train a gesture profile. This process may display a gesture on the screen and record the raw data from the sensors that correspond to that gesture. Haptic feedback may be used to communicate to the user when the arm in powered on, when the data is recording for a grip, and/or when the recording has stopped. For example, the user may be prompted make a closed hand gesture for five seconds and the raw data may be recorded from the sensors for that time. The data resulting for all the hand grips may be loaded into a neural network that utilize machine learning to look for patterns and to watch the raw data and trigger a particular grip in response to a recognized pattern. This process can be repeated many times to improve accuracy.

Additional electronics and/or software may be provided to enhance functionality. For example, onboard accelerometers, gyroscopes, and/or magnetometers may be used to measure the orientation and movement of the prosthesis. This monitoring may allow software to analyze this data and recognize patterns to trigger events or to conserve battery. For example, these components may be able to detect that the user is walking. In response, the prosthesis 10 may be put into a low power mode as it is unlikely that gripping motions will be used while walking. In another example, the monitoring may result in recognition that the walking is being performed during a particular event, such as carrying groceries, and the grip of the prosthetic hand 300 may be locked to help ensure the groceries remain firmly secure within the prosthetic hand 300. In another example, if the sensors detect a hand shake, the prosthetic hand 300 may close to make an intelligent selection based on movement. Recognizing these types of patterns throughout the day and week can help the prosthesis 10 become easier to use and to conserve battery. For example, if a certain grip is used more than others, the software can change the sensor input needed to trigger this grip making it easier to control.

The mobile application may also be used to configure the different grips and how those are triggered. For example, a user may be able to select the "pointer" grip to be triggered by the muscle being held for one second and the full hand close being triggered by a muscle burst. This allows the user to customize the device to function in a desired way.

It should be understood that the particular embodiment of prosthesis 10 illustrated in the figures and described above may be for a user with a forearm that has been amputated distal to the elbow joint. In other words, prosthesis 10 is suited for a user with an intact elbow joint. However, it should be understood that the concepts described herein can be applied to similar prosthetic devices for user's with various conditions of residual limbs, including a completely missing upper extremity.

For example, if the user is missing the elbow joint, the socket could include a lower and upper structure that attaches to the bicep area and shoulder area, instead of the bicep area and the residual forearm. In such a circumstance, a robotic elbow joint may be provided to replicate the motion of the elbow. For that circumstance, the electronics and mechanical parts may be located in a compartment within a prosthetic upper arm, rather than the prosthetic forearm.

In still another example, if the user has a large amount of the forearm remaining, there may be limited space within the prosthetic forearm to house the mechanical and/or electronic components. In that circumstance, the components may be positioned within the hollow space of the prosthetic hand 300. In this situation, the tunnels 311 may be unnecessary since the prosthetic tendons could be routed directly from the actuators within the hand to the fingers 360a-d and the thumb 330, freeing up more space for electronic components. The actuators in this scenario may be mounted in a staggered pattern to fit in the relatively small space. These may start near the knuckles and end near the wrist. The electronics and batteries could also be mounted in the palm cavity, for example either on top of or below the actuators.

Although in the embodiment described above, the prosthetic forearm 200 is substantially fixed relative to the palm 301, a mechanical joint may be provided to join the prosthetic forearm to the palm that allows for an amount of rotation. This rotation can be manual, for example similar to how the thumb rotates relative to the palm, or via an actuator. Such a wrist joint may instead be a powered wrist joint, which could provide one, two, or more degrees of freedom of motion, which could be controlled manually, via an actuator and electronics, or both. For example, one of the degrees of freedom may be flexion and extension. Another of the degrees of freedom may be pronation and supination. And another of the degrees of freedom may be radial deviation and ulnar deviation. It should be understood that any one or combination of the above movements may be provided in a wrist joint. These wrist joint movements may be driven through ha direct drive or tendon-based mechanism coupled to an actuator on the joint or within the prosthetic forearm 200 or palm 301.

Still further, the illustrated embodiment of device 10 includes three linear actuators 282 coupled to five prosthetic flexion tendons, with three attached to one of the linear actuators, and the other two linear actuators being coupled to a single flexion tendon, either for flexing the index finger or the thumb. However, the use of three actuators 282 may be particularly suited to smaller prostheses 10 in which there is limited space within prosthetic forearm 200. If there is space, at least five actuators may be provided so that each finger (and the thumb) has independent flexion control.

If the user is a candidate for a socket that requires a mechanical joint at the elbow or shoulder, mechanical springs may be used to assist with lifting the prosthesis. For example, torsion springs can be integrated into the mechanical joint to provide rotational force, so that the prosthesis feels lighter during elbow flexion. This may be achieved by mounting the legs of the spring to the upper and lower part of the socket so that the center of the spring is in line with the socket's axis of rotation. The default position of the spring may be when the elbow is bent to its maximum amount of flexion. This will then provide increasing resistance from the spring as the socket starts to straighten. The spring tension may be balanced so that the weight of the prosthetic device will overcome the spring tension, so the prosthetic device can be in a straight position. When a small amount of flexion force is added by the user, the springs assist, making the device easier to move. Further, one or more actuators may be used to assist with prosthetic elbow flexion and extension when a mechanical elbow joint is included in the upper extremity prosthesis. Such an actuator may be mounted on the socket and positioned to exert rotational force on an axis of rotation of the socket. One or more sensors may be incorporated into the system to determine if the user is extending or flexing the arm so that the motor powers the joint in the desired direction of movement. This may allow for less physical exertion and easier use for the user in flexing or extending the elbow. These actuators may be located on the axis of rotation, elsewhere on the socket, and/or within the prosthetic forearm and may transmit rotation or linear force to the axis of rotation of the socket.

The prosthetic device 10 described above may be designed to be modular so that the socket can be replaced with an electro-mechanical powered joint. This joint could be a prosthetic elbow joint that fastens to the forearm in the same or a similar way as the socket attaches. This prosthetic elbow joint may have an actuator and sensory feedback for accurate control. The prosthetic elbow joint may be able to lift the prosthetic forearm and hand and may be controlled using muscle sensors. Additional modular joints may be added to create a powered bicep and shoulder to achieve pronation, supination, abduction, adduction, flexion and extension of the shoulder and bicep. A universal bolt pattern may be used to fasten the joints together similar to how the socket attaches to the forearm as shown in FIG. 9. Wires for power and control may be routed to the forearm where they connect to the main control electronics. A secondary control board may be integrated into the module joints to control the motor and read position and current sensors. This may allow for easy integration, fewer wires being routed and smaller main control electronics. This may also allow the main control electronics to send desired position data to the modular joints where the secondary control electronics compute and control the joint.

Figure 30:
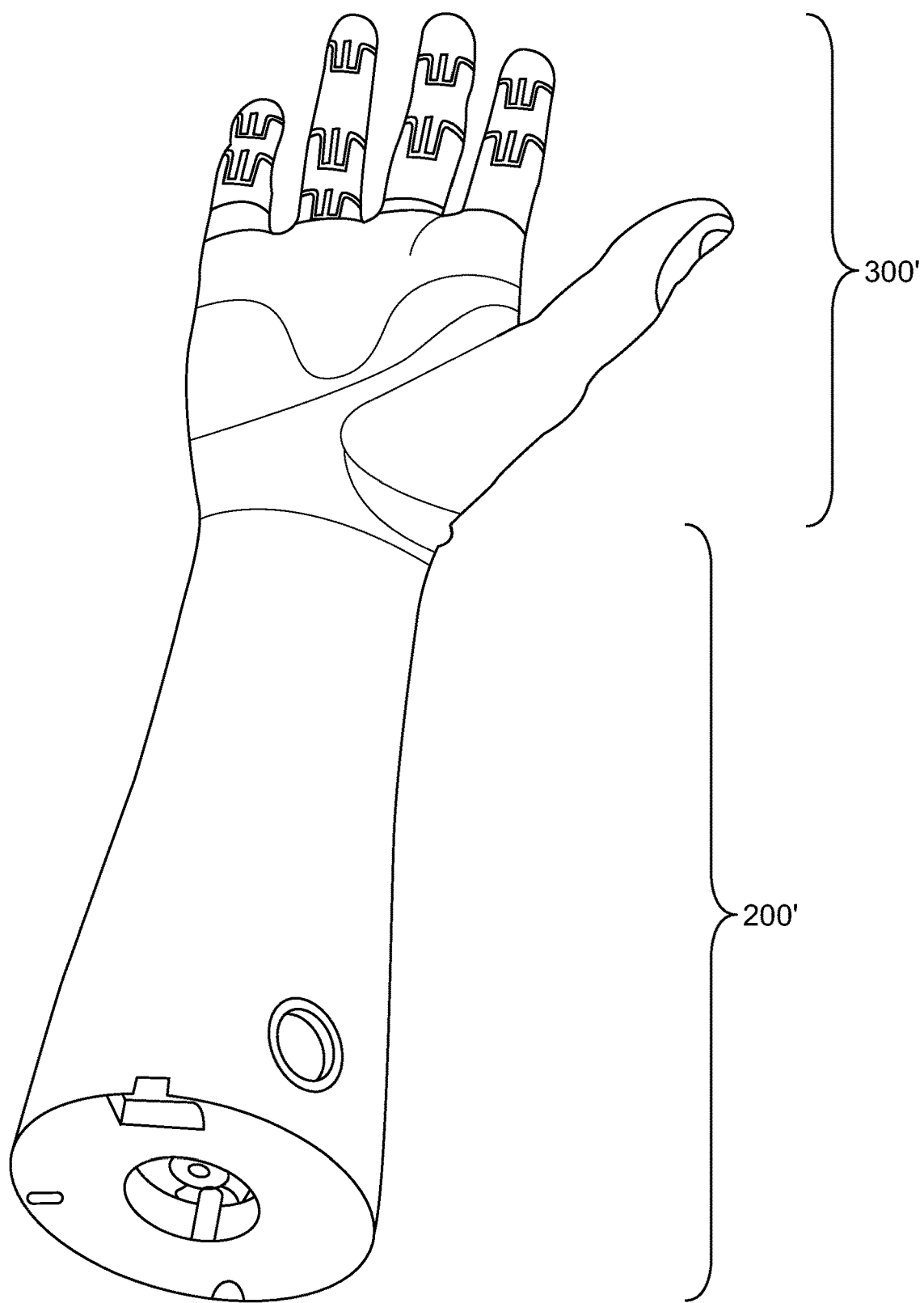
FIG. 30 is a perspective view of a prosthetic forearm assembled to a prosthetic hand according to another aspect of the disclosure.

As noted above, although in some embodiments most or all of the mechanical and electrical components of prosthetic upper extremity 10 may be housed within prosthetic forearm 200, in other embodiments, most or all of the mechanical and electrical components may be housed within prosthetic hand 300. On example of such an embodiment is shown in FIG. 30, which illustrates prosthetic forearm 200' and prosthetic hand 300'. It should be understood that many of the components of upper extremity 10 may otherwise be identical when using the embodiment of prosthetic forearm 200' and prosthetic hand 300', so much of the above description applies with equal force to prosthetic forearm 200' and prosthetic hand 300'.

Figure 31:
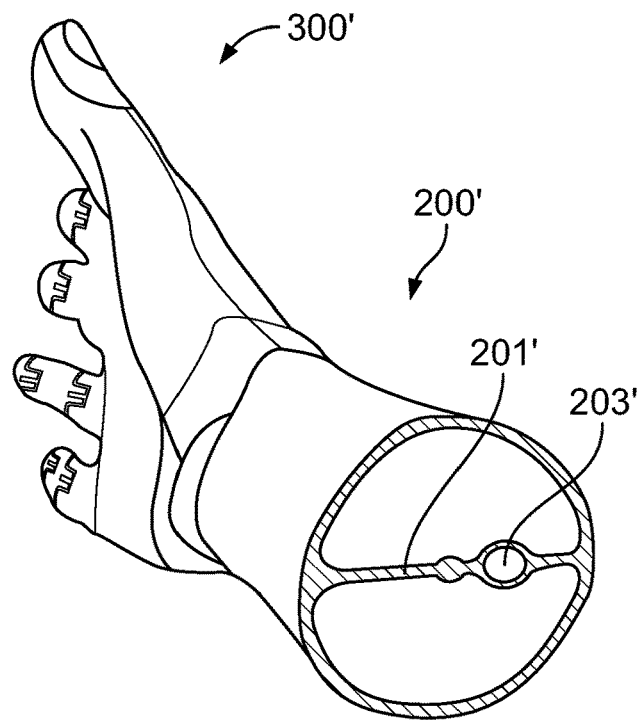
FIG. 31 is a transverse cross-section of the prosthetic forearm of FIG. 30.

Still referring to FIG. 30, prosthetic forearm 200' may be formed as a single integral member, as opposed to prosthetic forearm 200. For example, since prosthetic forearm 200' may not need to be accessed or need to house a significant amount of electrical and/or mechanical components therein, there may be no need to form prosthetic forearm 200' from multiple pieces, although it may be formed of multiple pieces if desired. The proximal end of prosthetic forearm 200' may include a feature(s) to couple to a prosthetic socket, such as prosthetic socket 100, that may the same or similar to those described above in connection with prosthetic upper extremity 10. In some embodiments, a mechanical attachment may be provided between prosthetic forearm 200' and socket 100 (or a socket similar to socket 100). As an example, a bolt or other fastener may be used to fasten prosthetic forearm 200' to socket 100, and may also act as a rotational pivot to rotate the prosthetic forearm 200' manually relative to the socket 100. This bolt or fastener may be tensioned to an appropriate degree so that the components are substantially fixed relative to each other, but still capable of manual rotation. The proximal end of prosthetic forearm 200' may also include a slot or other feature to allow for wires to pass between socket 100 and the interior of prosthetic forearm 200'. Prosthetic forearm 200' may include a recess 274' to receive a button, switch, or similar item therein, in the same or similar manner as described above in connection with recess 274 of prosthetic forearm 200. Prosthetic forearm 200' may be mostly hollow in order to reduce the weight of the prosthetic forearm 200' and to ease manufacturing. As shown in FIG. 31, prosthetic forearm 200' may include one or more supports 201, which may be in the form of ribs, flanges, etc. that assist in maintaining structural integrity of the prosthetic forearm 200' despite being substantially hollow. In addition, prosthetic forearm 200' may include one or more lumens, conduits, or passageways 203' that may assist in passing cables, such as electrical wires, through the prosthetic forearm 200', for example to connect sensors in a prosthetic socket to components within prosthetic hand 300'. Passageway 203' is shown in FIG. 31 as being formed as part of support 201', and extends from a proximal end to a distal end of prosthetic forearm 200'.

Figure 32:
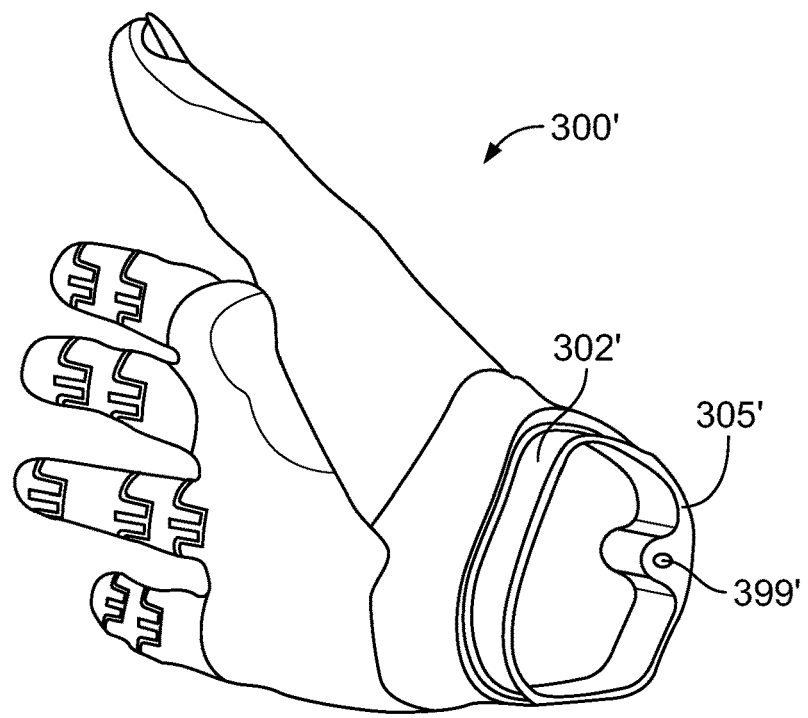
FIG. 32 is a perspective view of the prosthetic hand of FIG. 30.

Prosthetic hand 300' is illustrated isolated from the prosthetic forearm 200' in FIG. 32. Prosthetic hand may include a proximal coupling portion 302' that includes a lip 305' that is generally similar to proximal coupling portion 302 and corresponding lip 305 of prosthetic hand 300. Proximal coupling portion 302' may also include an aperture 399' that may align with a distal opening in passageway 203' to allow cables, wires, or other components that extend through prosthetic forearm 200' to enter the interior of prosthetic hand 300'.

Figure 33:
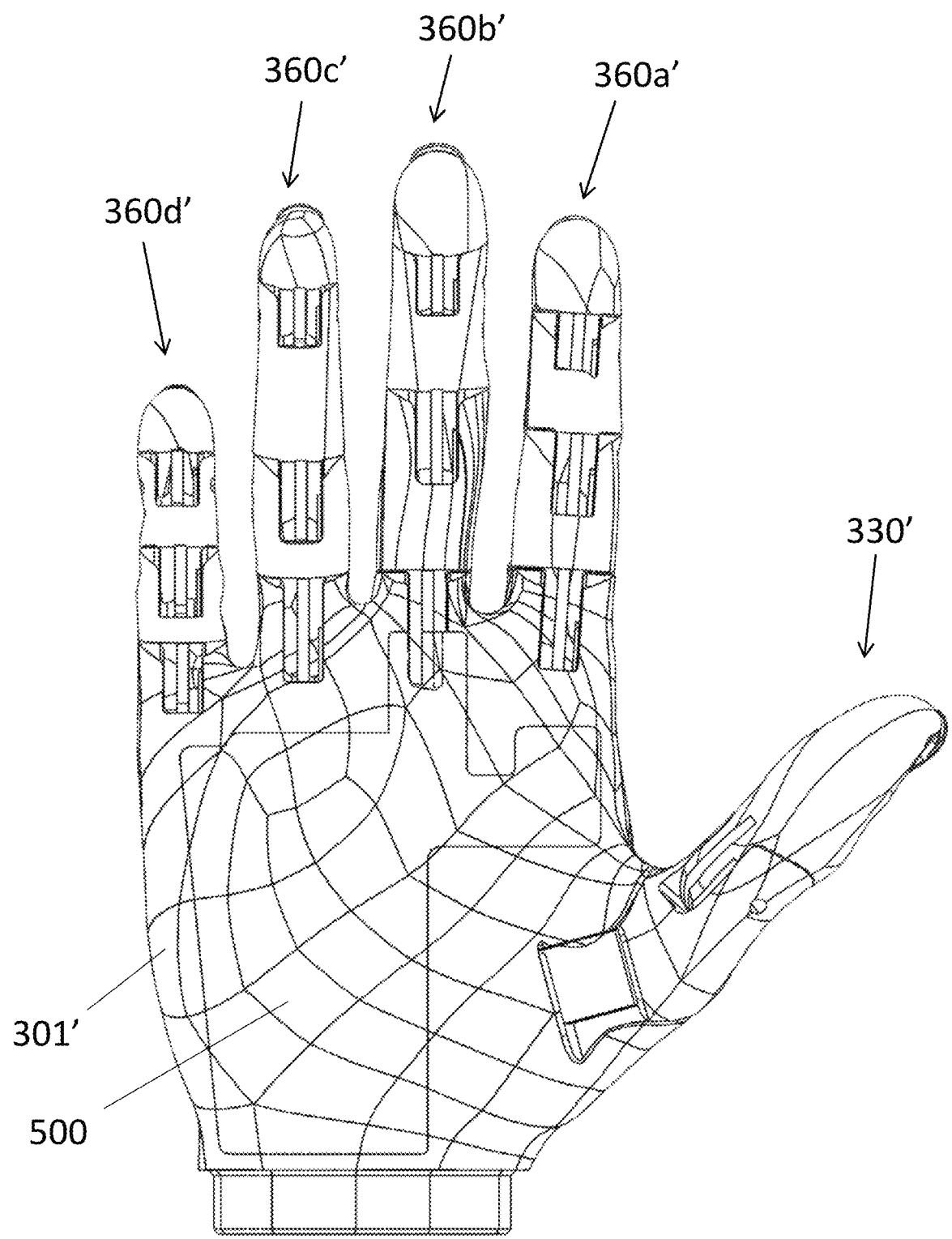
FIG. 33 is a front view of the prosthetic hand of FIG. 30.

FIG. 33 illustrates a front view of the palm 301' of prosthetic hand 300'. Generally, prosthetic hand 300' may be substantially identical to prosthetic hand 300 described above, with certain exceptions described below. In other words, unless a difference is pointed out between prosthetic hand 300 and prosthetic hand 300', or unless a difference is otherwise clearly present, the description of the corresponding portions of prosthetic hand 300 apply with equal force to prosthetic hand 300'. Generally, these exceptions include the fact that palm 301' includes an access panel 500 to access an interior volume of the palm 301' that may house electrical and/or mechanical components. Further, while the movement of fingers 360a'-360d' and thumb 330' may be generally similar or identical to those described in connection with hand 300, prosthetic hand 300' may utilize biasing members in the form of springs at each joint instead of extension tendons. And, as will be understood, internal components and structure of prosthetic hand 300' may be different than those of prosthetic hand 300.

Figure 34:
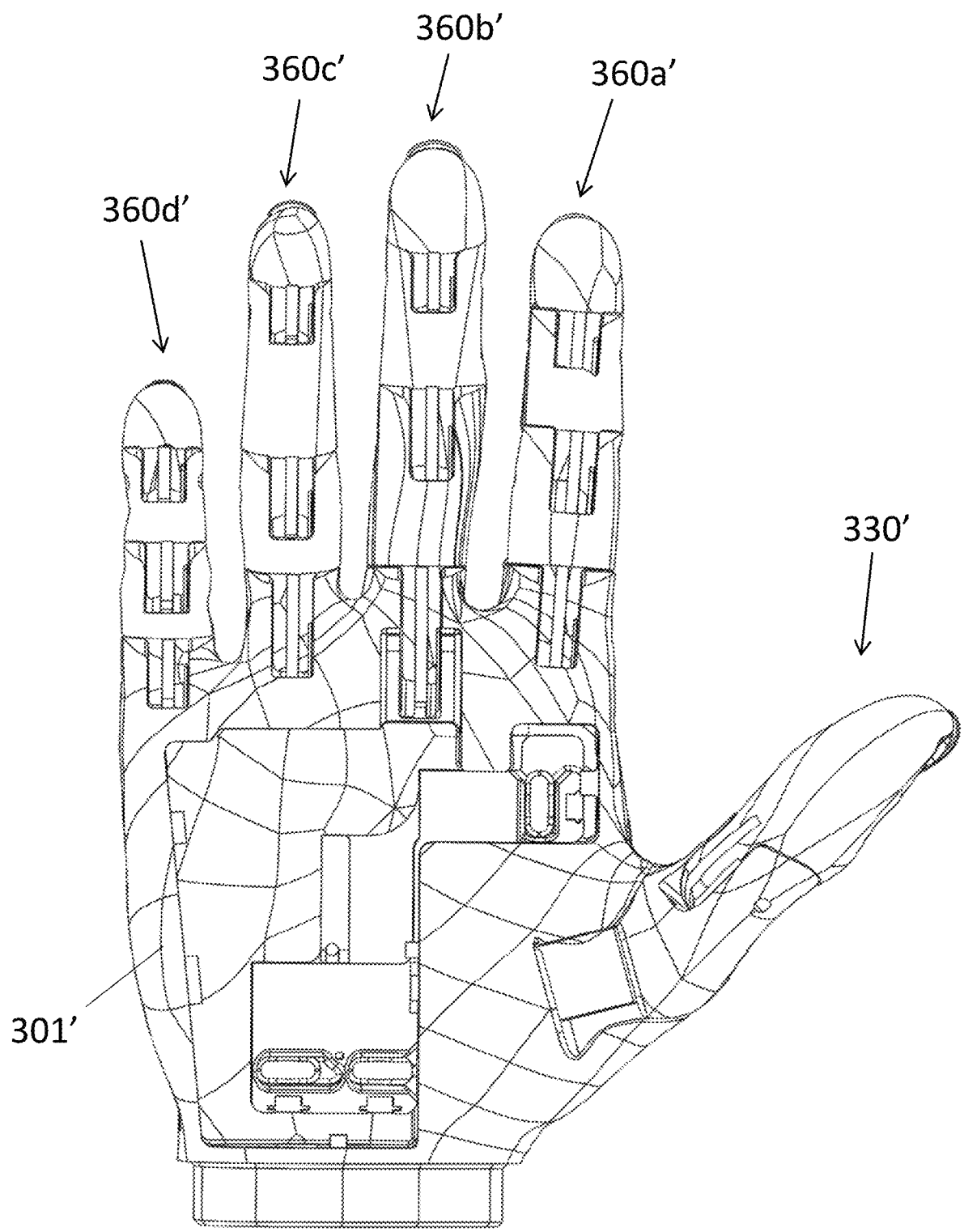
FIG. 34 is a front view of the prosthetic hand of FIG. 30 with an access panel removed.
Figure 35:
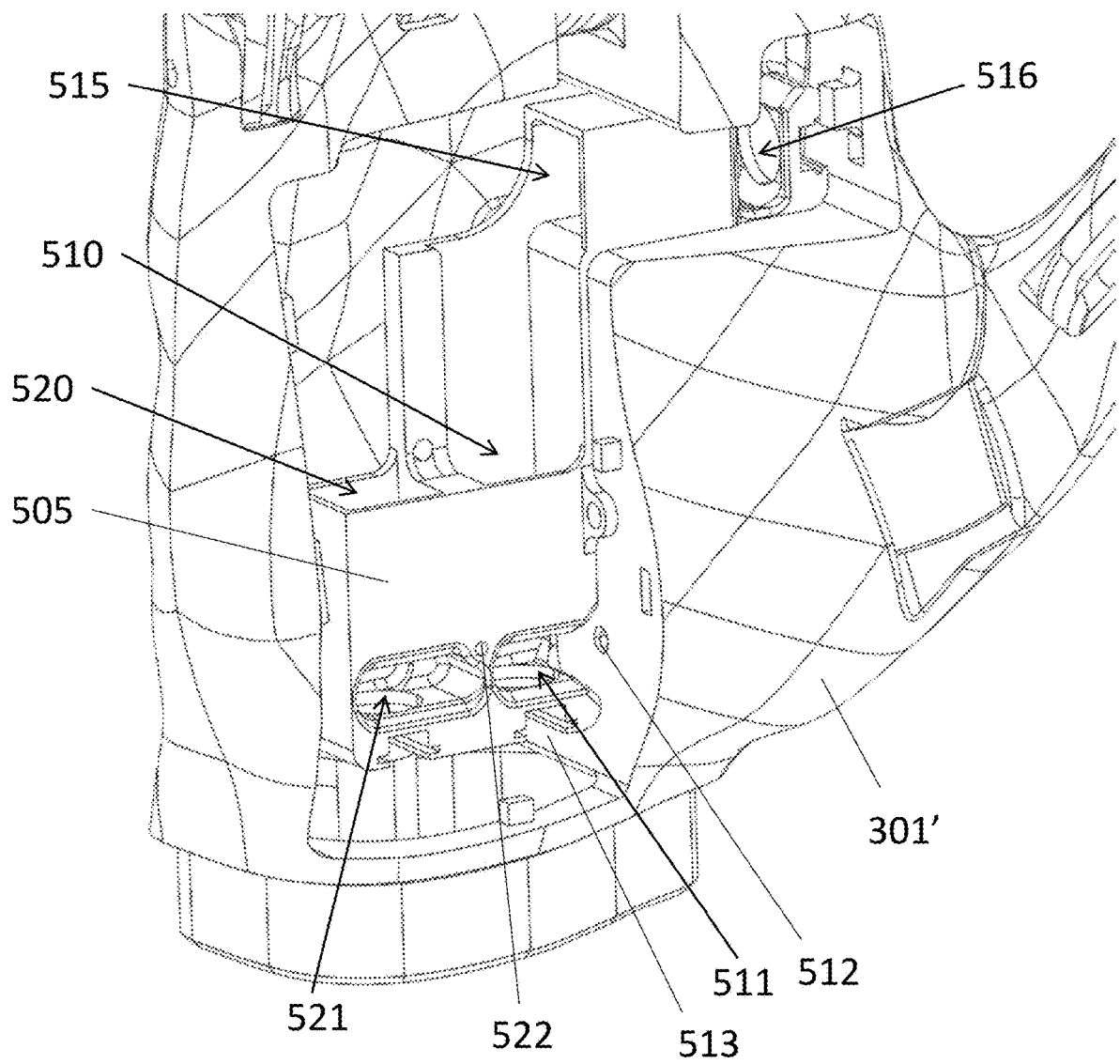
FIGS. 35-36 are enlarged perspective views of the prosthetic hand of FIG. 30 with the access panel removed.
Figure 36:
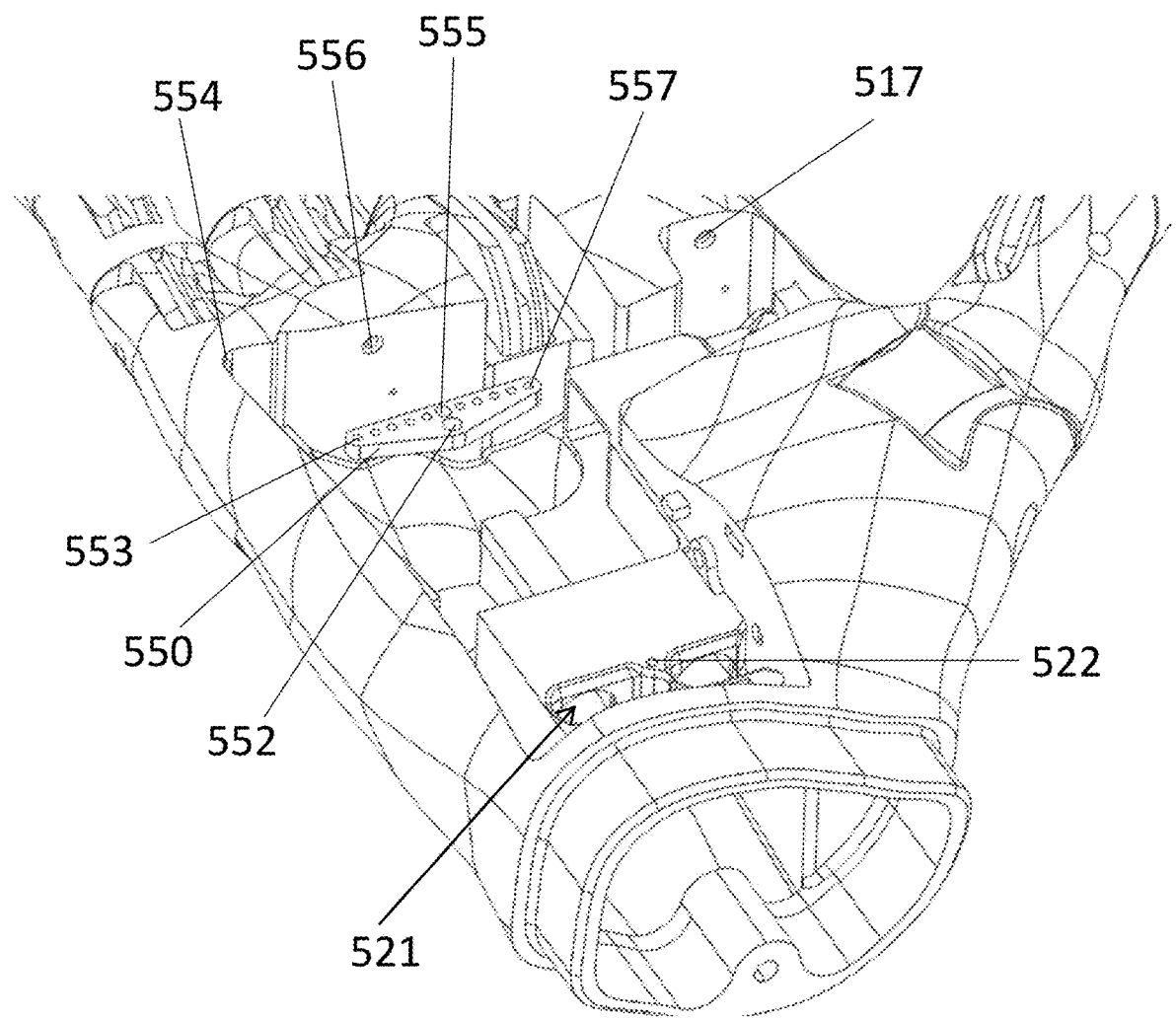

FIGS. 34-36 illustrate different views of prosthetic hand 300' with access panel 500 removed. It should be understood that FIGS. 34-36 do not illustrate motors, tendons, or other electrical components, which are instead shown in FIG. 36. Referring in particular to FIG. 35, the interior of palm 301' may include one or more receiving blocks or mounting members 505. In the illustrated embodiment, palm 301' includes a single mounting member 505 with three separate receiver cavities 510, 515, 520. Each receiver cavity 510, 515, 520 may function to receive and secure therein an actuator. However, it should be understood that multiple mounting members may be provided, each with a single (or more) receiver cavity, and more or fewer than three receiver cavities may be provided depending on the number of actuators that will be used with prosthetic hand 300'.

Figure 38:
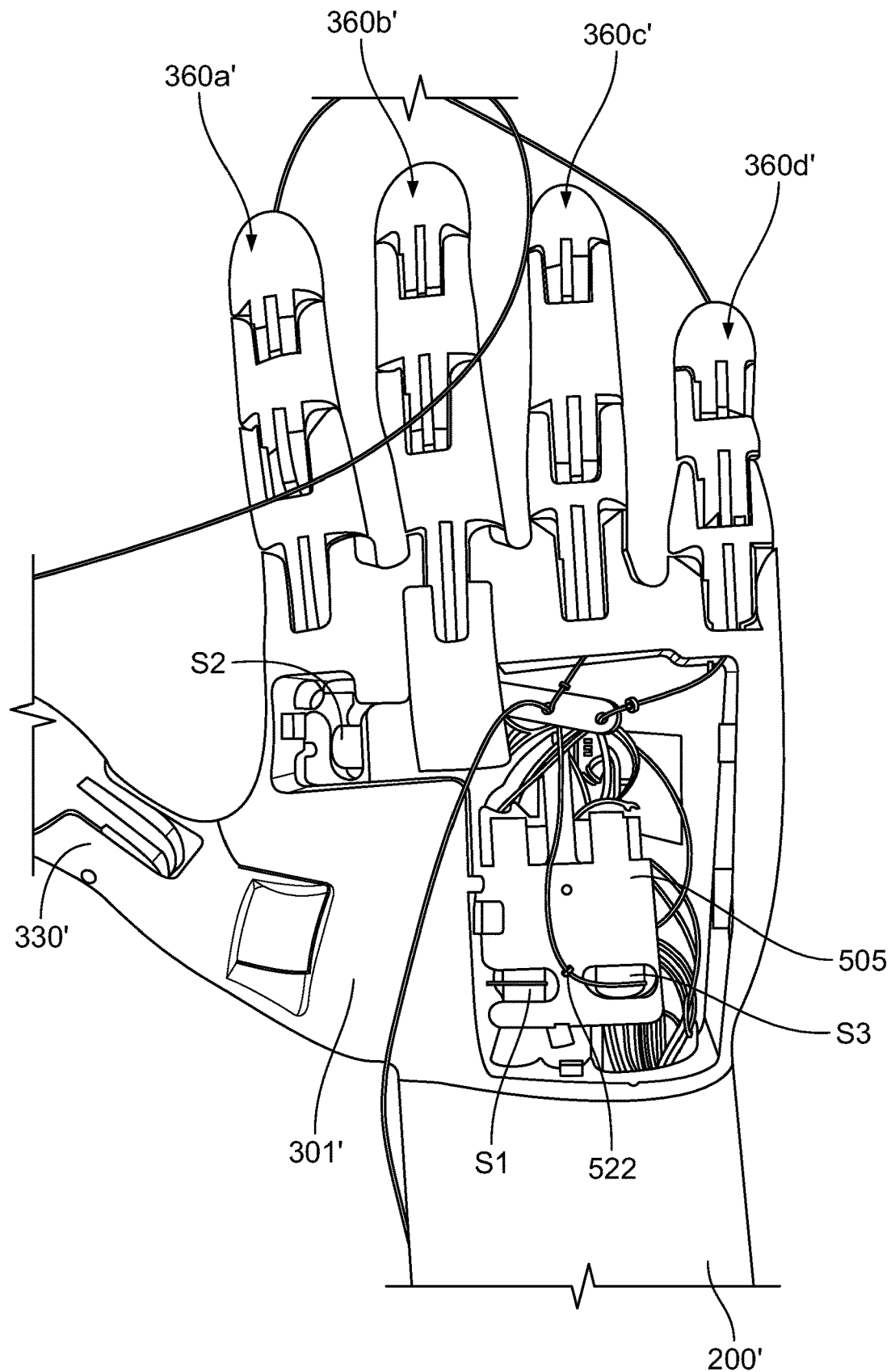
FIGS. 38-39 are pictures of a prosthetic hand similar to that shown in FIG. 30 with certain mechanical and electrical components in an assembled state.
Figure 39:
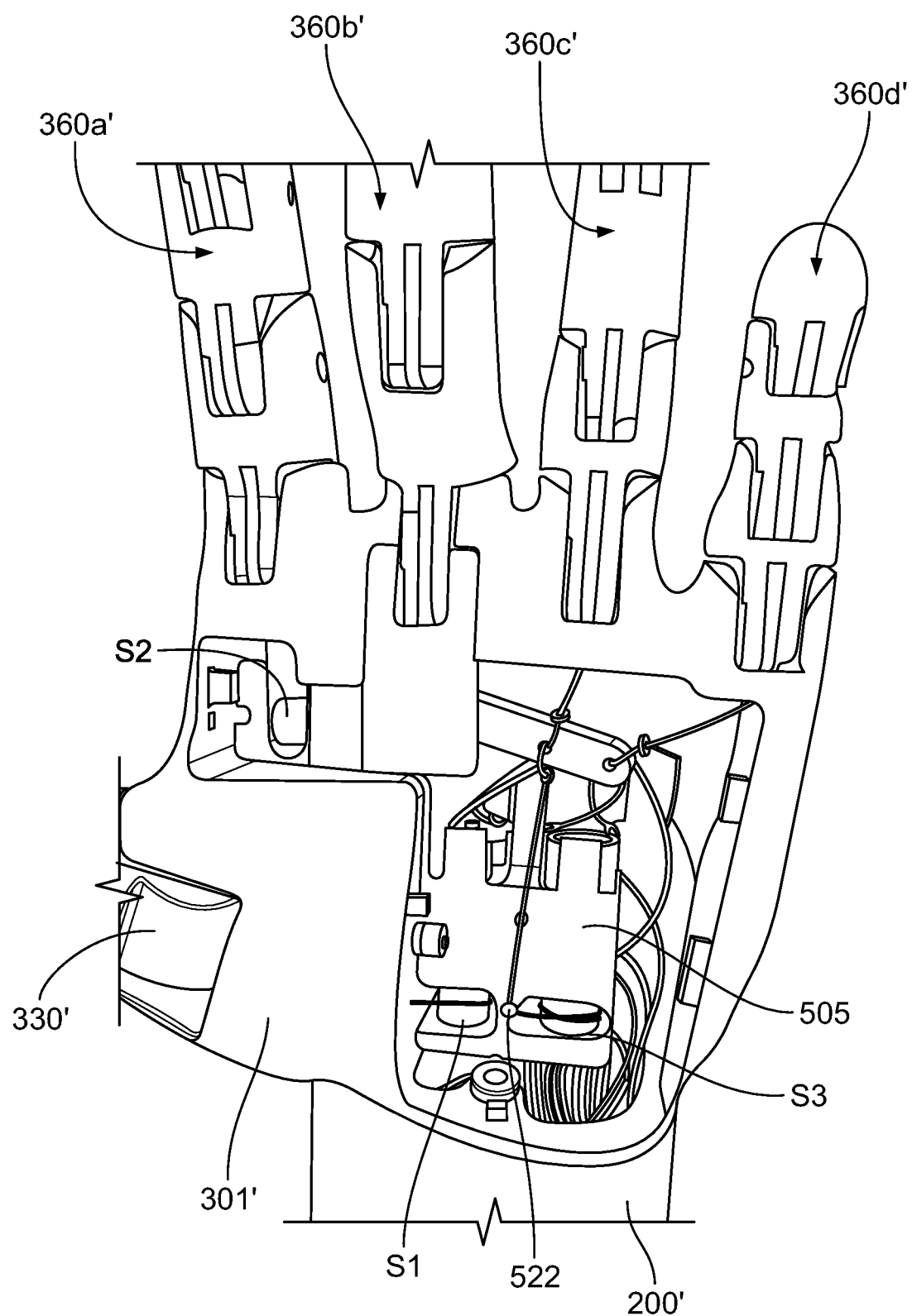

Receiver cavity 510 may receive an actuator for controlling the flexion of prosthetic thumb 330'. For example, a portion of the actuator may be received within cavity 510, with a portion of the actuator exposed via opening 511. A flexion tendon, which may take any suitable form, including the materials described in connection with the tendons above, may be spooled around a spindle portion of the actuator that is exposed via opening 511, with the actuator controlling the rotation of the spindle, and thus controlling flexion of the tendon. For example, the spindle may be positioned within opening 511 so that the tendon extends substantially tangentially to the spindle into an aperture 512. From there, the tendon may be routed through the joints of, and connected to the tip of, prosthetic thumb 330' in substantially the same way as described above for the flexion tendon of prosthetic thumb 330. As the actuator within receiver cavity 510 actuates, the spindle about which the tendon is wrapped may rotate, causing flexion of the prosthetic thumb 330' in substantially the same way as described for prosthetic thumb 300. The actuator may be any suitable type for precisely controlling flexion of the prosthetic thumb 330', including any of the actuators described above. For example, the actuators may be geared DC motors that utilize Hall Effect position feedback sensors. Further, it should be understood that, although upper extremity 10 was generally described to include linear actuators, other actuators that provide the desired flexion movement could be used for any of the embodiments described herein, whether or not considered "linear" actuators. Mounting member 505 and/or receiver cavity 510 may also include a slot 513 or other cavity to receive therein electronic components for use with the actuator. FIGS. 38-39 illustrate an example of prosthetic hand 300' (although it should be understood that FIGS. 38-39 illustrate a left hand, whereas FIGS. 33-36 illustrate a right hand) with spindle S1 positioned within opening 511 and a flexion tendon extending into the aperture 512 of prosthetic thumb 330'.

Referring again to FIG. 35, another actuator may be received within receiver cavity 515 to control flexion of prosthetic index finger 360a'. That actuator may be similar or identical to the actuator described above for prosthetic thumb 330'. One notable difference is that the actuator may be positioned within receiver cavity 515 in an orientation substantially orthogonal compared to the actuator received within receiver cavity 510. With this configuration, a spindle of the actuator may be exposed at opening 516 so that the flexion tendon extends substantially tangentially from the spindle and directly into an aperture 517, as best illustrated in FIG. 36, at the base of prosthetic index finger 360a'. The flexion tendon may be routed through the joints of, and connected to the tip of, prosthetic index finger 360a' in substantially the same way as described above for prosthetic index finger 360a, so that actuation of the actuator within receiver cavity 515 causes flexion of the prosthetic index finger 360a'. An example of a spindle S2 of an actuator within receiver cavity 515 is illustrated in FIGS. 38-39, which also illustrate the flexion tendon extending directly from the spindle into the aperture 517 at the base of prosthetic index finger 360a'. Receiver cavity 515 may also include a slot similar to slot 513 for receiving an electronic board or other electronic components.

Referring once again to FIG. 35, a third actuator may be received in receiver cavity 520 to control flexion of prosthetic middle finger 360b', prosthetic ring finger 360c', and prosthetic pinky finger 360d'. As with prosthetic hand 300, the flexion of these three fingers may all be controlled with a single actuator, although in other embodiments, if space allows, the flexion of each finger may be controlled by a dedicated actuator. Similar to receiver cavity 510, receiver cavity 520 may include an opening 521 through which a spindle of the actuator may be exposed. However, a number of differences may also be present with respect to this actuator. For example, whereas the spindles of the actuators that control the prosthetic thumb 330' and prosthetic index finger 360a' are generally positioned close to and in line with the flexion tendon on the spindle, opening 521 is positioned farther away from the three fingers it controls and may be offset from the point of connection of the flexion tendon. A loop or other guide member 522 may be provided near opening 521 so that the flexion tendon may extend from the spindle of the actuator within opening 521, and then in a direct line to its point of connection. This is best illustrated in FIGS. 38-39. Further, while prosthetic hand 300 was described as including three flexion tendons for the prosthetic fingers 360b-360d that were each coupled to a piston of a linear actuator, prosthetic hand 300' may instead include an adaptive grip bar 550. However, it should be understood that the adaptive grip bar 550, described in more detail, may be used with prosthetic hand 300, or in other embodiments, a system similar to the control of prosthetic fingers 360b-d in prosthetic hand 300 may be used with prosthetic hand 300'.

Adaptive grip bar 550 is best illustrated in FIGS. 36 and 38-39. Referring to FIG. 36, adaptive grip bar 550 is illustrated as suspended, although it will be understood that the suspension of the adaptive grip bar 550 is provided by its connection to various tendons. Referring to FIG. 36, adaptive grip bar may be wider than it is tall, and have a plurality of apertures to which tendons may be connected, for example by knotting ends of the tendons to the apertures.

Preferably, the adaptive grip bar 550 includes a base aperture 552 near its bottom at a left-to-right center of the bar. The tendon that runs from the spindle of the actuator positioned within opening 521, for example spindle S3 of FIGS. 38-39, may first pass to guide member 522, and then connect to base aperture 552. Preferably, the tendon is substantially vertically positioned between guide member 522 and aperture 552. Thus, as the actuator within receiver cavity 520 actuates, it pulls the tendon and thus pulls adaptive grip bar 550 downwards toward the proximal end of prosthetic hand 300'. Three separate flexion tendons may be coupled to the other apertures in adaptive grip bar 550. For example, a flexion tendon may have one end coupled to aperture 553 of adaptive grip bar 550, which may be positioned in vertical alignment with an aperture 554 in the base of prosthetic pinky finger 360d'. Similarly, another flexion tendon may have one end coupled to aperture 555 of adaptive grip bar 550, which may be positioned in vertical alignment with an aperture 556 of prosthetic ring finger 360c'. A third flexion tendon may have one end couple to aperture 557 of adaptive grip bar 550, which may be positioned in vertical alignment with a base of prosthetic middle finger 360b'. An aperture similar to apertures 554, 556 is not shown in connection with prosthetic middle finger 360b'. In some embodiments, such an aperture may be included in a similar fashion as shown with respect to prosthetic pinky finger 360d' and prosthetic ring finger 360c'. In other embodiments, such an aperture may be provided within access panel 500 at or near its points of coupling to prosthetic middle finger 360b'. Each of these three flexion tendons may be routed through the joints of, and coupled to the tips of, their respective prosthetic fingers 360b'-360d' in substantially the same way described above for the prosthetic flexion tendons of prosthetic fingers 360b-360d.

As the actuator received within receiver cavity 520 actuates, the tendon coupled to base aperture 552 pulls, causing the adaptive grip bar 550 to move toward the proximal end of prosthetic hand 300', which in turn pulls each of the three flexion tendons coupled to the adaptive grip bar 550, causing flexion of each of the three prosthetic fingers 360b'-360d. However, during flexion of those three prosthetic fingers, for example when gripping an object, there may come a point at which one finger, such as the prosthetic middle finger 360b', has essentially fully gripped the object, but another finger, such as the prosthetic pinky finger 360d', has not fully gripped the object. At this point, as the tendon coupled to base aperture 552 continues to pull on adaptive grip bar 550, the relative forces will cause the adaptive grip bar 550 to begin to pivot about base aperture 552, allowing the flexion tendon connected to the prosthetic pinky finger 360d' to continue to pull, while the flexion tendon connected to prosthetic middle finger 360b' does not pull or only minimally pulls. In other words, the adaptive grip bar 550 allows for the prosthetic middle finger 360b', the prosthetic ring finger 360c', and the prosthetic pinky finger 360d', to flex to different levels depending on the object gripped by the prosthetic hand 300', despite the fact that a single actuator is used to cause flexion in all three prosthetic fingers. As should be understood, the adaptive grip bar 550 acts as a "teeter totter" of sorts, pivoting based on the amount of, and relative positioning of, forces applied on the adaptive grip bar 550 by the three flexion tendons and the tendon connecting the adaptive grip bar 550 to the actuator.

The above description provides an explanation of how each of the prosthetic fingers 360a'-360d' and the prosthetic thumb 330' flex when actuated. Regarding extension, as noted above, a different embodiment may be used in prosthetic hand 300' than compared with prosthetic hand 300, although it should be understood that either method may be used in either prosthetic hand, depending on the particular desire. Typically, if prosthetic hand 300' includes most or all of the mechanical components of the prosthetic upper extremity 10, the amount of available space is reduced compared to if the mechanical components are provided within the larger prosthetic forearm 200'. Thus, while prosthetic forearm 200 includes biasing members in the form of various extension tendons coupled to compression springs to bias the fingers to the extended position, prosthetic hand 300' may use different biasing members that may require less space.

Figure 37:
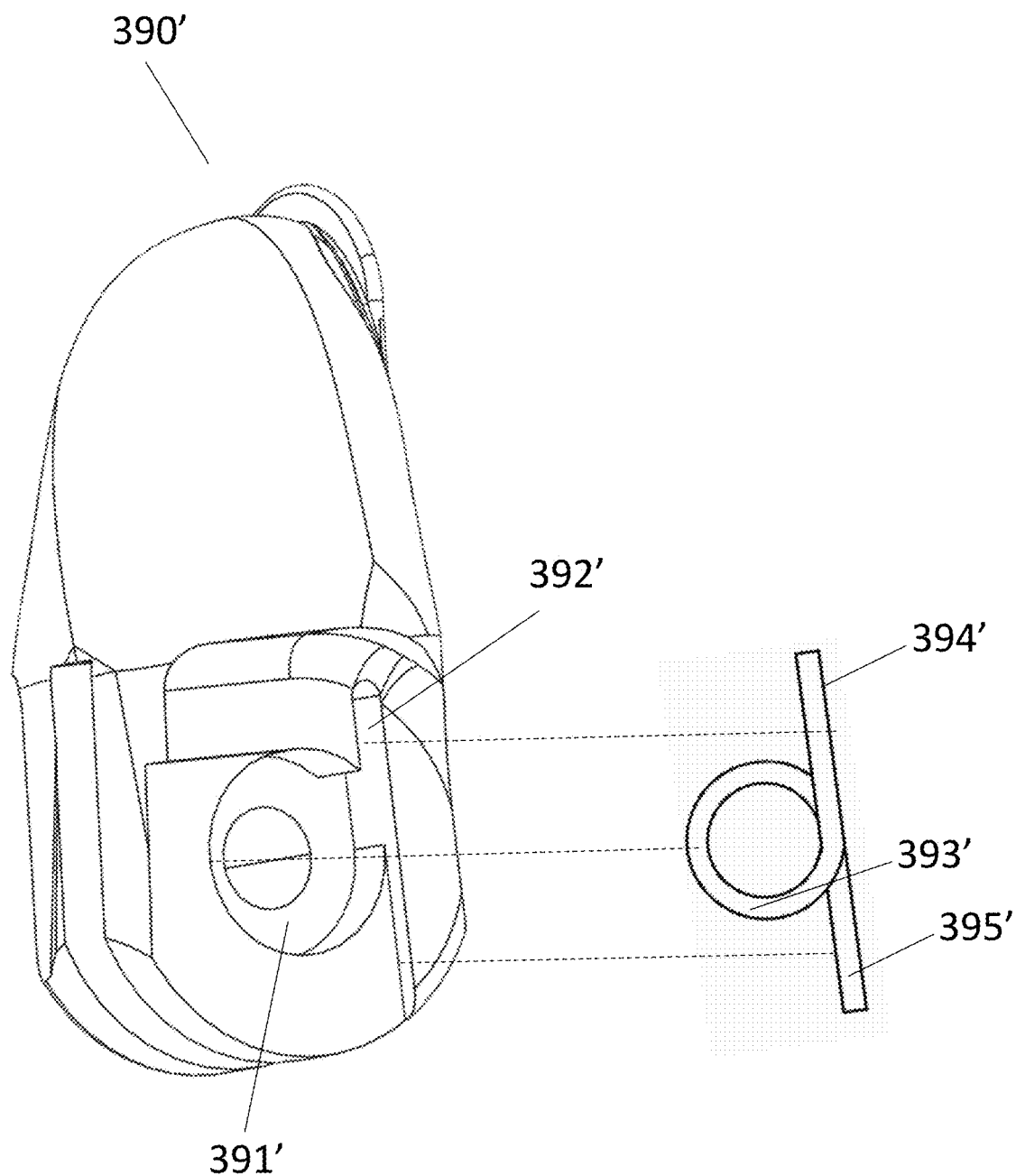
FIG. 37 illustrates a fingertip of one of the prosthetic fingers of a prosthetic hand.

FIG. 37 illustrates a fingertip 390' of one of the prosthetic fingers of prosthetic hand 300'. It should be understood that fingertip 390' is representative of the tip of each prosthetic finger, including prosthetic thumb 330'. Fingertip 390' may be similar or identical to fingertip 390 described above in all ways, with at least one exception. Finger 390' may include a recess 391' that is generally circular, and which opens to a substantially straight recess 392'. These recesses 391', 392' may be sized and shaped to receive a biasing member, for example a spring such as a torsion spring. Torsion springs are generally known, and an example torsion spring having a center portion 393' and two legs 394', 395' at about a 180 degree angle is illustrated. The center portion 393' of the torsion spring may be received within recess 391', and the legs 394', 395' of the torsion spring may be received in recess 392'. With this configuration, the legs 394', 395' of the torsion spring are at about 180 degrees with the relevant finger is fully extended. As the finger begins to flex, leg 395' of the torsion spring may be in contact with the adjacent joint, causing the angle between legs 394' and 395' to reduce as the finger flexes. The torsion spring thus will provide a counter biasing force that tends to extend the particular joint as the flexion forces from the flexion tendons are released. It should be understood that although only a single torsion spring for a single finger joint is illustrated, a similar torsion spring may be provided for each of the three joints in the prosthetic fingers 360a'-360d', as well as the flexion joint of the prosthetic thumb 330'. And it should be understood that each portion of each prosthetic finger may include a similar structure to receive or otherwise house a torsion spring, such that each joint is independently biased toward the extended condition in the absence of other applied forces. In FIG. 37, a single torsion spring is illustrated on one side of the fingertip 390'. It should be understood that a single torsion spring may be provided on either side of the fingertip 390', or in comes cases, it may be desirable to provide a torsion spring (or other similar biasing member) on each side of the fingertip 390. The same applies to each of the other portions of the fingers and the thumb.

Although sensors and related electric components described in connection with the first embodiment of prosthetic upper extremity 10 have not been described in great detail with respect to prosthetic forearm 200' and prosthetic hand 300', it should be understand that many or all of the same electric components (including batteries) and/or sensors may be used. For example, sensors in the socket (whether the socket is adapted for an above the elbow or below the elbow amputee) may be coupled to appropriate electronic controls within prosthetic hand 300', for example via cables or other wires extending through prosthetic forearm 200'. The mounting member 505 may also serve as a mount for all of the electronics and the batteries within palm 301'. For the sake of brevity, these components are not described here again.

Although an upper prosthetic extremity 10 that includes prosthetic arm 200 and prosthetic hand 300 may be effective for many uses, an upper prosthetic extremity 10 that includes prosthetic hand 300' may have particular benefits. For example, for an amputee missing a hand and an entire forearm, the desired prosthesis may be relatively large as an entire prosthetic forearm may be required. However, in other situations, space may be at more of a premium. For example, for an individual that has a significant amount of the native forearm remaining, a prosthesis would have a correspondingly smaller forearm portion. Thus, an upper extremity prosthesis that includes the entire prosthetic forearm 200 described above may not be possible or practical, and thus a relatively smaller prosthetic forearm may have less space to house mechanical and/or electrical components. Thus, housing these components in prosthetic hand 300' may allow for more versatility. In fact, by having the prosthetic hand 300' act as essentially a self-contained prosthesis, the remaining portions of the upper extremity prosthesis could be designed to fit essentially any patient. For example, for an amputee who has portions of the native forearm, a socket could be created in essentially the same manner described above for the forearm, and only the missing portion of the patient's forearm needs to be replicated, for example via additive manufacturing, and the prosthetic hand 300' would be coupled to that prosthetic forearm. Regardless of the particularities of the missing extremity, because all or mostly all of the functional components are positioned within prosthetic hand 300', the remainder of the prosthesis could easily be designed for the particular patient without significant concerns about how and where to house the functional components of the prosthesis.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An upper extremity prosthesis comprising:
a prosthetic hand including a prosthetic thumb having a base and a tip, a prosthetic index finger having a base and a tip, a prosthetic middle finger having a base and a tip, a prosthetic ring finger having a base and a tip, and a prosthetic pinky finger having a base and a tip;
first and second actuators operably coupled to the upper extremity prosthesis;
a first prosthetic flexion tendon having a first end operably coupled to the first actuator and a second end coupled to the tip of the prosthetic thumb;
a first biasing system operably coupled to the prosthetic thumb;
a second prosthetic flexion tendon having a first end operably coupled to the second actuator and a second end coupled to the tip of the prosthetic index finger;
a second biasing system operably coupled to the prosthetic index finger;
a third actuator operably coupled to the upper extremity prosthesis;
a third biasing system operably coupled to the prosthetic middle finger;
a fourth biasing system operably coupled to the prosthetic ring finger; and
a fifth biasing system operably coupled to the prosthetic pinky finger;
a third prosthetic flexion tendon having a first end operably coupled to the third actuator and a second end coupled to the tip of the prosthetic middle finger;
a fourth prosthetic flexion tendon having a first end operably coupled to the third actuator and a second end coupled to the tip of the prosthetic ring finger; and
a fifth prosthetic flexion tendon having a first end operably coupled to the third actuator and a second end coupled to the tip of the prosthetic pinky finger;
wherein upon actuation of the first actuator in a first direction, the first prosthetic flexion tendon causes the prosthetic thumb to flex, and upon actuation of the first actuator in a second direction opposite the first direction, the first biasing system causes the prosthetic thumb to extend; and
wherein upon actuation of the second actuator in the first direction, the second prosthetic flexion tendon causes the prosthetic index finger to flex, and upon actuation of the second actuator in the second direction, the second biasing system causes the prosthetic index finger to extend,
wherein upon actuation of the third actuator in the first direction, the third, fourth, and fifth prosthetic flexion tendons cause the prosthetic middle finger, prosthetic ring finger, and prosthetic pinky finger to flex, respectively, and upon actuation of the third actuator in the second direction, the third, fourth, and fifth biasing systems cause the prosthetic middle finger, prosthetic ring finger, and prosthetic pinky finger to extend, respectively,
the upper extremity prosthesis further including a coupling tendon having a first end operably coupled to the third actuator and a second end coupled to an adaptive grip bar at a coupling location, the third, fourth, and fifth prosthetic flexion tendons each having the respective first ends coupled to the adaptive grip bar, the adaptive grip bar being rotatable about the coupling location.

2. The prosthesis of claim 1, wherein the coupling tendon and the third, fourth, and fifth prosthetic flexion tendons together suspend the adaptive grip bar, so that forces applied on the adaptive grip bar by the coupling tendon may be unevenly applied to the third, fourth, and fifth prosthetic flexion tendons.

3. The prosthesis of claim 1, further comprising a prosthetic forearm coupled to the prosthetic hand.

4. The prosthesis of claim 3, further comprising a socket coupled to the prosthetic forearm, the socket adapted to interface with a residual limb of a user of the upper extremity prosthesis.

5. The prosthesis of claim 4, further comprising a force sensor coupled to the socket and adapted to provide information to a processor within the upper extremity prosthesis in response to a muscle contraction of the user, the processor adapted to actuate the first and second actuators based on the information.

6. The prosthesis of claim 4, further comprising an electromyography sensor coupled to the socket and adapted to provide information to a processor within the upper extremity prosthesis in response to a muscle contraction of the user, the processor adapted to actuate the first and second actuators based on the information.

7. The prosthesis of claim 4, further comprising a combined sensor coupled to the socket, the combined sensor including a force sensor and an electromyography sensor, the combined sensor adapted to provide information to a processor within the upper extremity prosthesis in response to a muscle contraction of the user, the processor adapted to actuate the first and second actuators based on the information.

8. The prosthesis of claim 1, wherein the prosthetic hand includes an internal volume accessible via an access cover.

9. The prosthesis of claim 8, wherein the first and second actuators are positioned within the interior volume of the prosthetic hand.

10. The prosthesis of claim 1, wherein the prosthetic index finger includes a middle portion positioned between the base and the tip of the prosthetic index finger.

11. The prosthesis of claim 10, wherein the tip of the prosthetic index finger is rotatable relative to the middle portion of the prosthetic index finger, the middle portion of the prosthetic index finger is rotatable relative to the base of the prosthetic index finger, and the base of the prosthetic index finger is rotatable relative to a palm of the prosthetic hand.

12. The prosthesis of claim 11, wherein upon actuation of the second actuator in the first direction, during a first flexion action the base of the prosthetic index finger rotates relative to the palm, during a second flexion action the middle portion of the prosthetic index finger rotates relative to the base of the prosthetic index finger, and during a third flexion action the tip of the prosthetic index finger rotates relative to the middle portion of the prosthetic index finger.

13. The prosthesis of claim 12, wherein upon actuation of the second actuator in the first direction, the first flexion action occurs prior to the second flexion action, and the second flexion action occurs prior to the third flexion action.

14. An upper extremity prosthesis comprising:
a prosthetic hand including a prosthetic thumb having a base and a tip, and a prosthetic index finger having a base and a tip;
first and second actuators operably coupled to the upper extremity prosthesis;
a first prosthetic flexion tendon having a first end operably coupled to the first actuator and a second end coupled to the tip of the prosthetic thumb;
a first biasing system operably coupled to the prosthetic thumb;
a second prosthetic flexion tendon having a first end operably coupled to the second actuator and a second end coupled to the tip of the prosthetic index finger;
a second biasing system operably coupled to the prosthetic index finger; and
a prosthetic index fingernail adapted to couple to the tip of the prosthetic index finger,
wherein upon actuation of the first actuator in a first direction, the first prosthetic flexion tendon causes the prosthetic thumb to flex, and upon actuation of the first actuator in a second direction opposite the first direction, the first biasing system causes the prosthetic thumb to extend;
wherein upon actuation of the second actuator in the first direction, the second prosthetic flexion tendon causes the prosthetic index finger to flex, and upon actuation of the second actuator in the second direction, the second biasing system causes the prosthetic index finger to extend; and
wherein in an assembled condition, the prosthetic index fingernail and the tip of the prosthetic index finger form a substantially closed outer boundary, and in an unassembled condition, the tip of the prosthetic index finger presents an opening to access an interior volume of the tip of the prosthetic index finger.

15. The prosthesis of claim 14, wherein in the assembled condition, the prosthetic index fingernail is magnetically coupled to the tip of the prosthetic index finger.

16. An upper extremity prosthesis comprising:
a prosthetic hand including a prosthetic thumb having a base and a tip, and a prosthetic index finger having a base and a tip, the base of the prosthetic thumb being coupled to the prosthetic hand via a pin, the prosthetic thumb being rotatable about the pin between a first rotational position and a second rotational position;
first and second actuators operably coupled to the upper extremity prosthesis;
a first prosthetic flexion tendon having a first end operably coupled to the first actuator and a second end coupled to the tip of the prosthetic thumb;
a first biasing system operably coupled to the prosthetic thumb;
a second prosthetic flexion tendon having a first end operably coupled to the second actuator and a second end coupled to the tip of the prosthetic index finger;
a second biasing system operably coupled to the prosthetic index finger; and
a locking mechanism that locks the prosthetic thumb in the first rotational position and in the second rotational position in the absence of rotational force being applied to the prosthetic thumb,
wherein upon actuation of the first actuator in a first direction, the first prosthetic flexion tendon causes the prosthetic thumb to flex, and upon actuation of the first actuator in a second direction opposite the first direction, the first biasing system causes the prosthetic thumb to extend; and
wherein upon actuation of the second actuator in the first direction, the second prosthetic flexion tendon causes the prosthetic index finger to flex, and upon actuation of the second actuator in the second direction, the second biasing system causes the prosthetic index finger to extend.

\* \* \* \* \*